US007927849B2

(12) United States Patent
Paloheimo et al.

(10) Patent No.: US 7,927,849 B2
(45) Date of Patent: Apr. 19, 2011

(54) LACCASE ENZYME AND USE THEREOF

(75) Inventors: Marja Paloheimo, Vantaa (FI); Leena Valtakari, Rajamaki (FI); Terhi Puranen, Nurmijarvi (FI); Kristiina Kruus, Espoo (FI); Jarno Kallio, Jarvenpaa (FI); Arja Mantyla, Helsinki (FI); Richard Fagerstrom, Espoo (FI); Pentti Ojapalo, Tuusula (FI); Jari Vehmaanpera, Klaukkala (FI)

(73) Assignee: AB Enzymes OY, Rajamaki (FI)

( * ) Notice: Subject to any disclaimer, the term of this patent is extended or adjusted under 35 U.S.C. 154(b) by 934 days.

(21) Appl. No.: 11/231,706

(22) Filed: Sep. 21, 2005

(65) Prior Publication Data

US 2006/0063246 A1    Mar. 23, 2006

Related U.S. Application Data

(60) Provisional application No. 60/611,819, filed on Sep. 21, 2004.

(30) Foreign Application Priority Data

Sep. 21, 2004 (FI) .................................... 20041220

(51) Int. Cl.
*C12N 9/00* (2006.01)
*C12N 9/02* (2006.01)
(52) U.S. Cl. .................. 435/183; 435/4; 435/6; 435/25; 435/69.1; 435/71.1; 435/189; 435/252.3; 435/320.1; 536/23.2
(58) Field of Classification Search .................. 435/183, 435/209, 69.1, 69.7; 510/320; 424/94.4; 536/23.2
See application file for complete search history.

(56) References Cited

U.S. PATENT DOCUMENTS

| | | | |
|---|---|---|---|
| 5,750,388 A | 5/1998 | Berka et al. | |
| 5,752,980 A | 5/1998 | Pedersen et al. | |
| 5,770,418 A | 6/1998 | Yaver et al. | |
| 5,843,745 A | 12/1998 | Berka et al. | |
| 5,981,243 A | 11/1999 | Berka et al. | |
| 5,985,818 A | 11/1999 | Svendsen et al. | |
| 5,998,353 A | 12/1999 | Pedersen et al. | |
| 6,573,086 B1 | 6/2003 | Emalfrab et al. | |
| 2005/0089980 A1* | 4/2005 | Kruus et al. .................... 435/189 |
| 2008/0248016 A1* | 10/2008 | Paloheimo et al. .......... 424/94.4 |

FOREIGN PATENT DOCUMENTS

| | | |
|---|---|---|
| DE | 19821263 | 11/1998 |
| EP | 0244234 | 11/1987 |
| EP | 0765394 | 10/2001 |
| WO | WO92/18683 | 10/1992 |
| WO | WO96/33836 | 12/1995 |
| WO | WO97/08325 | 3/1997 |
| WO | WO97/25468 | 7/1997 |
| WO | WO97/43384 | * 11/1997 |
| WO | WO98/27197 | 6/1998 |
| WO | WO98/46820 | 10/1998 |
| WO | WO01/92489 | 12/2001 |

OTHER PUBLICATIONS

Kiiskinen et al. (Purification and characterization of a novel laccase from the ascomycete Melanocarpus albomyces, Appl Microbiol Biotechnol (2002) 59:198-204).*
Aho, S.et al. 1991. Monoclonal antibocdies against core . . . Eur J. Biochem 2001: 643-649.
Altschul , S. F. et al. 1990. Basic Local Alignment Search Tool. J. Mol Biol 215: 403-410.
Edman P and Begg G. A 1967 A Protein Sequenator. European J. Biochem 1: 80-91.
Leonowic A and Grzywnowicz K. 1980 Quantitative estimation of laccase forms in.. Enzyme Microb. Technol. 3:55-58.
Gasteiger E. et al. 2003. ExPASy: the proteomics servers for in depth.. Nucleic Acids Research 31(13):3784-3788.
Joutsjoki V.V. et al. 1993. Tranformation of Trichoderma reesei . . . Curr Genet 24: 223-228.
Karhunen T. et al. 1993. High frequency one-step gene replacement . . . Mol Gen Genet. 241: 515-522.
Kiiskinen L-L. and Saloheimo M. 2004. Molecular Cloning and Expression . . . Appl. Env. Microb. 70(1): 137-144.
Laemmli U.K. 1970 Cleavage of Structureal proteins . . . Nature 227: 680-685.
Lowry OH et asl. 1951. Protein measuremtn with the folin phenol reagent. J. Biol CHem 193: 265-275.
Malardier L. et al. 1989 Cloning of the . . . Gene 78: 147-156.
Mueller M. and Shi C. 2000. Laccase for decorization of indigo . . . AATCC, 2000 International conference and exhibition.
Nielsen H. et al. 1997. Indentification of procaryotic and eucaryotic . . . Protein Engineering 10(1):1-6.
Nielsen H. and Krogh A. 1998. Predication of signal peptides and signal . . . In Proc. VI COnf of Intell. Systems for Mol. Biol. (ISMB 6) 122-130.
Niku-Paavola M-L. et al. 1988 Lignolytic enzymes of hte . . . Biochem J. 254: 877-884.
Paloheimo M. et al. 2003. High-Yield Production of . . . Applied and Envir. Mecrob. 69(12): 7073-7082.
Palonen H. et al. 2003 Purification , characterization . . . Enzyme and Microbial Technol. 33: 854-862.
Penttila M. et al. 1987. A versatile transformation system for the cellulolytic . . . Gene 61: 155-164.
Raeder U. and Broda P. 1985. Rapid preparation of DNA from filamentous fungi. Lett. in Appl. Microb. 1: 17-20.
Schlosser D et al. 1997. Patterns of lignolytic enzymes . . . App.l. Microb. Biotech. 47:412-418.

(Continued)

*Primary Examiner* — Ling-Siu Choi
*Assistant Examiner* — Bijan Ahvazi
(74) *Attorney, Agent, or Firm* — Dodds & Associates; Leea Susanne Somersalo; John Dodds

(57) ABSTRACT

The present invention relates to a novel laccase enzyme obtainable from the strains of genus *Thielavia*. The invention relates also to the nucleic acid sequence encoding the enzyme, a recombinant host into which the nucleic acid sequence has been introduced and a method for the production of the enzyme in a recombinant host. The enzyme of the invention is suitable for several applications, in particular for increasing the lightness of denim.

22 Claims, 23 Drawing Sheets

OTHER PUBLICATIONS

Sigillot, C. et al. 2004. NAtural and recombinant fungal laccases . . . Appl. Microbiol. Technol. 64: 346-352.

Paszcynski A. et al. 1985. Enzymatic Activities of an . . . FEMS Microbiol Lett. 29: 37-41.

Rice, P. et al. 2000. EMBOSS: The European Molecualr Biology . . . Trends in Genetics. 16: 276-277.

Stone K.L. et al. 1988. In Techniques in Protein CHemistry. 377-391. T.E. Hugli (ed.) Academic Press New York.

* cited by examiner 1. 2. 3. 4. 5. 6. 7.

```
Peptide 1
 1   2   3   4   5   6   7   8   9   10  11  12        13  14  15  16  17  18  19
 Y   Q   G   A   P   N   T   L   P   T   N   Q/I       G   L   P   V   P   N   H
TAC CAA GGA GCA CCA AAC ACA CTA CCA ACA AAC CAA/ATA   GGA CTA CCA GTA CCA AAC CAC
 T   G   C   C   C   T   C T C  C   C   T   G   C    C T C  C   C   C   T   T
         G   G   G       G   G  G   G               T  G   G   G   G   G
         T   T   T       T   T  T   T                  T   T   T   T   T Peptide 2
 1   2   3   4   5   6   7   8   9   10  11
 E   N   W   I   G   P   D   G   V   L   K
GAA AAC TGG ATA GGA CCA GAC GGA GTA CTA AAA
 G   T       C   C   C   T   C   C T C   G
             T   G   G       G   G   G
                 T   T       T   T   T Peptide 3
 1   2   3   4   5   6   7   8   9
(S)  L   F   L   A   V   G   Q   R
AGA CTA TTC CTA GCA GTA GGA CAA AGA
TCC T C  T T C   C   C   C   G C C
 G   G       G   G   G   G       G
 T   T       T   T   T   T       T
```

Fig. 5.

Ta lcc1 and the deduced amino acid sequence

```
   1  ggatccccgggtcagtctatataaggggctgagtgtccagctcttccatgcctttgattc
  61  tcttgaatcaccaggacactcgggcggcttcagtcttgcataactcgggtcttcccttcc
 121  tctcactgcttttcttcgctcagatatatttcaggcgacctcaaacagctcgccatcATG
   1                                                              M 181  AAGTCTTGGGCCGCCGCCGTGGCGCTCATGGTGGGCATTCTCAGCCCTCATGCTGCCGCC
   2  K  S  W  A  A  A  V  A  L  M  V  G  I  L  S  P  H  A  A  A 241  GCACCTCCTGCAAACCCGGTCCAGAGAGACATGCTCCAGGTCCTTGAGGCGAGACAGTCT
  22  A  P  P  A  N  P  V  Q  R  D  M  L  Q  V  L  E  A  R  Q  S 301  GGCCCGACTTGCAACACCCCGTCCAATCGTGCGTGCTGGACCAATGGTTTCGACATCAAC
  42  G  P  T  C  N  T  P  S  N  R  A  C  W  T  N  G  F  D  I  N 361  ACCGACTATGAAGTCAGCACTCCTAATACCGGACGTACTGTGGCCgtaagcttcccctcc
  62  T  D  Y  E  V  S  T  P  N  T  G  R  T  V  A  intron 1 (51 bp)

421  ctttaaggaggcagagctaggactaacaagcaccagTACCAACTTACCCTCACTGAGAAA
  77                                       Y  Q  L  T  L  T  E  K 481  GAGAACTGGATCGGTCCCGATGGCGTTCTCAAGAATGTGGTGATGTTGGTCAATGgtacg          Peptide 2
  85  E  N  W  I  G  P  D  G  V  L  K  N  V  V  M  L  V  N 541  ttgatgtccaattctgtataaagagaagaaacgtgctgatacgctcccttcgtctagACA
 104                 intron 2 (62 bp)                              K 601  AGATTATAGgtatgttgtcaaacccgctgtaaccccaaccgccaagacctggaggctcct
 105  I  I  G               intron 3 (91 bp)

661  cgcctggacgtgttgtacaatatgctgacctcgccgcaagGGCCAACCATCCGCGCGAAC
 108                                           P  T  I  R  A  N 721  TGGGGTGACAATATCGAAGTCACTGTCATCAACAATCTCAAAACCAATGGgtacgaccac
 114  W  G  D  N  I  E  V  T  V  I  N  N  L  K  T  N  G 781  ttgaatcatcccgggcctacccctaacacaaaatctcaacgtgcatccgatctgacgtat
      intron 4 (83 bp)

841  tatatccatctagTACCTCGATGCACTGGCATGGCCTTCGTCAGCTGGGTAACGTTTTCA          Cu-binding
 131                T  S  M  H  W  H  G  L  R  Q  L  G  N  V  F  N 901  ACGACGGTGCCAACGGCGTGACTGAGTGCCCAATCCCGCCCAAAGGAGGGCGCAAGACGT
 147  D  G  A  N  G  V  T  E  C  P  I  P  P  K  G  G  R  K  T  Y 961  ACAAGTTCCGTGCGACACAGTATGGCACCAGCTGGTATCACTCCCACTTCTCGGCCCAGT          Cu-binding
 167  K  F  R  A  T  Q  Y  G  T  S  W  Y  H  S  H  F  S  A  Q  Y 1021  ACGGCAACGGCGTGGTCGGCACCATCCAGATCGACGGCCCTGCCTCTCTGCCATATGACA
 187  G  N  G  V  V  G  T  I  Q  I  D  G  P  A  S  L  P  Y  D  I 1081  TTGATCTGGGCGTGTTCCCTCTCATGGACTACTACTACAGGTCGGCCGATGAGCTGGTGC
 207  D  L  G  V  F  P  L  M  D  Y  Y  Y  R  S  A  D  E  L  V  H 1141  ACTTCACCCAGAGCAACGGCGCCCCGCCAAGCGACAACGTCCTCTTCAATGGCACCGCCC
 227  F  T  Q  S  N  G  A  P  P  S  D  N  V  L  F  N  G  T  A  R 1201  GTCACCCTGAGACGGGGGCAGGCCAGTGGTACAACGTCACGCTGACTCCAGGCAAGCGAC
 247  H  P  E  T  G  A  G  Q  W  Y  N  V  T  L  T  P  G  K  R  H 1261  ACCGCCTGCGCATCATCAACACGTCGACCGACAACCACTTTCAGGTGTCGCTTGTCGGCC
 267  R  L  R  I  I  N  T  S  T  D  N  H  F  Q  V  S  L  V  G  H
```

Fig. 6A

| | | |
|---|---|---|
| 1321 | ACAACATGACCGTCATTGCCACCGACATGGTCCCCGTCAACGCCTTTACTGTCAGCAGCC | |
| 287 | N M T V I A T D M V P V N A F T V S S L | |
| 1381 | TATTCCTCGCCGTAGGCCAGCGATACGATGTCACCATCGACGCCAATAGCCCGGTGGGCA | Peptide 3 |
| 307 | P L A V G Q R Y D V T I D A N S P V G N | |
| 1441 | ACTACTGGTTCAACGTGACTTTCGGCGATGGGTTGTGCGGCTCCAGTAACAACAAATTCC | |
| 327 | Y W F N V T F G D G L C G S S N N K F P | |
| 1501 | CAGCCGCCATCTTCCGCTACCAGGGCGCCCCCGCTACGCTCCCGACGGATCAGGGTCTAC | Peptide 1 |
| 347 | A A I F R Y Q G A P A T L P T D Q G L P | |
| 1561 | CCGTGCCCAATCACATGTGTTTGGACAACCTGAACCTAACTCCTGTGGTGACACGGAGCG | |
| 367 | V P N H M C L D N L N L T P V V T R S A | |
| 1621 | CGCCCGTCAACAACTTTGTCAAGCGTCCGTCCAACACGCTGGGCGTCACTCTCGATATCG | |
| 387 | P V N N F V K R P S N T L G V T L D I G | |
| 1681 | GCGGCACGCCGCTCTTTGTGTGGAAGGTCAACGGCAGCGCCATCAACGTCGACTGGGGCA | |
| 407 | G T P L F V W K V N G S A I N V D W G K | |
| 1741 | AGCCGATCCTTGACTATGTCATGAGCGGCAACACGAGCTACCCGGTCAGCGATAACATTG | |
| 427 | P I L D Y V M S G N T S Y P V S D N I V | |
| 1801 | TGCAGGTGGACGCTGTTGACCAGgtacgcccctcttgaagcccctagcagttcacgctag | |
| 447 | Q V D A V D Q          intron 5 (79 bp) | |
| 1861 | tatacaatacaagtacatgctaacacttccctccctattcagTGGACTTACTGGCTGATC | |
| 454 |                                           W T Y W L I | |
| 1921 | GAGAACGACCCGACCAATCCCATTGTCAGCTTGCCGCACCCGATGCATCTGCACgtacgt | Cu-binding |
| 460 | E N D P T N P I V S L P H P M H L H | |
| 1981 | tcaaacctcccccacccccacttcatacaaaatatactgacaaatcgacagGGCCACG | |
| 478 |        intron 6 (59 bp)                         G H D | |
| 2041 | ACTTCCTCGTCCTGGGCCGATCACCCGACGAGCTCCCCAGCGCGGGGGTCCGTCACATCT | |
| 481 | F L V L G R S P D E L P S A G V R H I F | |
| 2101 | TTGACCCGGCCAAGGACCTGCCCCGGCTTAAGGGCAACAACCCCGTGCGGCGGGACGTGA | |
| 501 | D P A K D L P R L K G N N P V R R D V T | |
| 2161 | CGATGCTTCCGGCGGGCGGCTGGCTGCTGCTGGCGTTCAAGACGGACAACCCGGGCGCAT | |
| 521 | M L P A G G W L L L A F K T D N P G A W | |
| 2221 | GGCTGTTCCACTGCCACATTGCGTGGCACGTGTCGGGCGGCCTGTCGGTCGACTTCCTCG | Cu-binding |
| 541 | L F H C H I A W H V S G G L S V D F L E | |
| 2281 | AGCGGCCCAACGACCTTCGCACGCAGCTCAACAGCAACGCCAAGCGCGCCGACCGCGACG | |
| 561 | R P N D L R T Q L N S N A K R A D R D D | |
| 2341 | ACTTCAACCGCGTCTGCCGCGAGTGGAACGCCTACTGGCCTACCAACCCGTTCCCCAAGA | |
| 581 | F N R V C R E W N A Y W P T N P F P K I | |
| 2401 | TCGACTCGGGCTTGAGGCACCGGTTTGTTGAGGAGAGCGAGTGGATGGTTCGCTAAactg | |
| 601 | D S G L R H R F V E E S E W M V R * | |
| 2461 | cctggctgtgccaattgatttgatgggtacatgtacctgttggtgttactgttgacgagg | |
| 2521 | ctgtgtaagtaccatggcaaaggggtgttttcagggggtgctctggggtaattggcacagt | |
| 2581 | acatggaggggtctggggttgggtatacaaggcttgctgctccgttttttatctttttggct | |
| 2641 | tgattaagactttcttgtctgatgtacgagtcaggccgcc | |

Fig. 6B pALK1667 expression cassette (10.1 kb)

LACCASE ENZYME AND USE THEREOF

PRIORITY

This application claims priority of the U.S. provisional application No. 60/611,819 filed on Sep. 21, 2004 and incorporated herein by reference.

SEQUENCE DATA

This application contains sequence data provided on a computer readable diskette and as a paper version. The paper version of the sequence data is identical to the data provided on the diskette.

FIELD OF THE INVENTION

This invention relates to a novel laccase enzyme useful in many applications, particularly in denim treatment. This invention relates also to a nucleic acid encoding the enzyme, a vector, a host cell and a method for producing the enzyme as well as an enzyme preparation comprising the enzyme. Furthermore, this invention relates to methods for treating denim, methods for stain removal, methods for treating natural or man-made fibers or lignocellulosic fibres, methods for treating wool, methods for treating hair and methods for bleaching pulp and dye house effluents and methods for decolorizing dyes. This invention relates also to various uses and compositions, which can be used in the mentioned applications.

BACKGROUND OF THE INVENTION

Laccases (EC. 1.10.3.2 p-benzenediol: oxygen oxidoreductase) belong to a family of multi-copper oxidases. Laccases are widely distributed enzymes in higher plants, fungi, some insects and bacteria. They are characterized by low substrate specificity, oxidizing various substrates, including diphenols, polyphenols, different substituted phenols, diamines, aromatic amines, and even inorganic compounds like iodine. Laccases oxidize their substrates by a one-electron oxidation mechanism, and they use molecular oxygen as an electron acceptor. Among laccases the primary sequence, induction mechanism, physico-chemical (e.g. isoelectric point and carbohydrate content) and biochemical characteristics are variable. The copper binding sites of laccases are, however, strictly conserved.

Several laccase proteins and genes encoding these laccases have been previously isolated. WO 01/92498 describes a fungal laccase enzyme isolated from *Melanocarpus albomyces* strain. The enzyme having pH optimum within 5 to 8 and working at temperatures between 30 to 80° C. is well suited to industrial applications requiring high pH and temperature conditions whereas the majority of known fungal laccases function in an acidic pH range and are not very thermostable. The patent EP 0765394 B1 (corresponding U.S. Pat. No. 5,981,243) describes the cloning of a laccase gene from *Myceliophthora thermophila* and its expression in *Aspergillus*. The pH optimum of the laccase was 6.5 and the enzyme retained full activity 20 min in 60° C. U.S. Pat. No. 5,750,388 describes the cloning of a laccase gene from *Scytalidium thermophilum* and its expression in *Aspergillus*. The pH profiles of *Scytalidium* laccase activity has optimal pH of 7 and 4 for syringaldazine and ABTS oxidation, respectively. The laccase was more thermostable at neutral to alkaline pH than at acidic pH.

Laccases have many industrially potential applications, such as delignification of wood pulps, methods for treating lignin containing fibers, methods for treating wood fibers in order to functionalize them or glue the fibers, improval of the production of fuel ethanol from renewable raw materials, food applications (for example in baking or clarification of beer or wine), various bioremediative processes and textile applications, such as denim treatment, stain removal, treatment of various fibers for textile industry, methods for decolorizing dyes and methods for treating dye house effluents, or use in hair dyeing composition, in hard-surface cleaning or in detergent formulations.

"Stone washed" look or an abraded look has been denim producers' interest in recent years. Traditional stone washing with pumice stones reduces the strength of fabric and burdens the laundering apparatuses. Past years the trend has been towards enzymatic denim finishing processes. "Bleached look" of denim is normally obtained by means of sodium hypochlorite. So far this "chlorine bleaching" has been the most efficient bleaching method for denim dyed with Indigo, since almost all shades can be obtained. However, hypochlorite process is environmentally very harmful, it is difficult to control and it damages the fabric easily. It is also very inconvenient or even harmful method for the user, it cannot be used for Lycra containing products and antichlor treatment with several rinsing/washing steps is required. Intensive research has been underway for development of ecologically less harmful alternative for sodium hypochlorite, in particular laccases have been studied. So far the results with commercial laccase preparations cannot be compared to those obtained by "chlorine bleaching" as far as the effects and the looks are concerned. Heavy faded look has been very difficult or impossible to achieve without sodium hypochlorite.

WO 97/25468 describes the use of laccase in a method for providing to dyed denim an abraded look. The method comprises a cellulase treatment and simultaneous or subsequent treatment with a phenol oxidizing enzyme, such as laccase, and an enhancing agent, such as methylsyringate. *Trametes villosa* and *Myceliophthora thermophila* laccases are the examples of laccases in the patent publication.

Despite of the numerous publications describing laccases from various microorganisms, the prior art does not describe any laccase which could be used in denim treatment to replace the chemical bleaching agents. There is thus a need for novel laccase enzymes having more efficient oxidizing capacity, in particular more efficient oxidizing capacity of Indigo.

There is also a need for novel laccases, which would function more effectively and be more suitable for the various conditions in different applications.

SUMMARY OF THE INVENTION

It is an aim of the present invention to eliminate at least some of the problems associated with the prior art. In particular, it is an aim of this invention to provide a novel laccase enzyme with which it is possible to decrease the amount or avoid the use of chemical bleaching agents in denim treatment. By using the laccase enzyme of the present invention, it is possible to decrease or avoid the use of chemical bleaching agents, such as sodium hypochlorite.

This invention is based on the surprising finding that laccase enzyme of the present invention can increase the lightness of denim as much as, or above, the level obtained by sodium hypochlorite. The laccase treatment increases the lightness of denim in particular on the face side of denim, which is also the desired result of denim treatment.

One object of this invention is thus a laccase enzyme that under suitable conditions is capable of increasing the lightness of denim at least, or above, as many units as denim treated by sodium hypochlorite. The result obtained by laccase treatment of the present invention has been compared to bleaching result obtained with sodium hypochlorite at test conditions, which represent conventional sodium hypochlorite bleaching conditions.

More specifically, the laccase enzyme of this invention is characterized by what is stated in the characterizing part of claim 1.

This invention thus encompasses laccases, which are capable of increasing the lightness of denim on the face side of denim at least as many units as sodium hypochlorite under test conditions. Surprisingly, this effect can be achieved already when only desized denim is treated. When laccase treatment is made on desized and cellulase treated denim, the laccases of the present invention can increase lightness of denim at least 20%, preferably at least 60% more than sodium hypochlorite under test conditions.

One object of the present invention is a laccase enzyme that is capable, under suitable conditions, in a single treatment, to obtain lightness value ($L^*$), on the face side of denim, at least 47, preferably at least 50, when Indigo dyed denim with lightness value ($L^*$) on the face side of denim equal or lower than 32 after cellulase treatment is used for the laccase treatment.

One object of the present invention is a laccase enzyme that is capable in a single treatment and under suitable conditions to obtain increase of lightness value ($L^*$), on the face side of denim, at least 17 units, preferably at least 25 units, when Indigo dyed denim with lightness value ($L^*$) on the face side of denim equal or lower than 32 after cellulase treatment is used for laccase treatment.

One object of the present invention is also a laccase enzyme, which comprises the amino acid sequence SEQ ID NO: 12 or a sequence showing at least 74% identity to the sequence SEQ ID NO: 12 when the full-length sequences encoded by the corresponding genes are compared.

More specifically the laccase enzyme of this invention is characterized by what is stated in the characterizing part of claim 22.

The novel laccase of the present invention has high oxidizing activity towards various substrates. The enzyme is also capable of functioning in various conditions in different applications.

This invention encompasses enzymes, which have high oxidizing capacity of various substrates and are thus suitable for different applications. In particular, this invention relates to laccases having the specific activity of at least 800 nkat/mg on ABTS at pH 4.5 or at least 200 on syringaldazine at pH 5.5.

The enzyme is preferably obtainable from a microorganism, more preferably from a filamentous fungus, in particular from the genus *Thielavia*, more specifically from the species *Thielavia arenaria*. Advantageously, the enzyme is obtainable from the strain CBS 116071 deposited on 2 Sep. 2004 at Centraalbureau voor Schimmelcultures, Upsalalaan 8, 3584 CT, Utrecht, the Netherlands.

The laccase enzyme of the present invention functions at broad pH range. The enzyme functions at pH 3.5 to 8, preferably at pH 4 to 7.5 under suitable conditions. Most preferably the enzyme functions at pH 5 to 7. The enzyme functions also at broad temperature range. For example, in denim treatment the enzyme is effective at the temperature of 30 to 80° C., preferably at 50 to 70° C., most preferably at 60 to 70° C. The enzyme functions also at room temperature (18 to 30° C.), although with slower reaction rate than at higher temperatures.

One object of this invention is also a nucleic acid sequence encoding the enzyme of the present invention.

Further objects of this invention are a vector comprising the nucleic acid sequence of the invention and a host comprising the nucleic acid sequence or the vector, and a process for the production of a polypeptide having laccase activity.

One further object of the invention is a process for obtaining an enzyme preparation comprising the polypeptide or enzyme, which comprises the steps of culturing a host cell comprising the nucleic acid sequence encoding the enzyme of the invention or a vector comprising the nucleic acid sequence encoding the enzyme of the invention and recovering the polypeptide. Furthermore, an object of the invention is the enzyme preparation comprising the laccase enzyme of the invention.

One object of this invention is a method for treating denim, which comprises contacting denim in an aqueous medium with the laccase enzyme or enzyme preparation of the invention under suitable conditions for the function of the enzyme.

One object of this this invention is a method for removing stains, which comprises that material to be treated with the method is contacted with a laccase enzyme of the present invention under suitable conditions for the function of the enzyme.

This invention provides also a method of bleaching pulp, for treating fibers, a method for treating wool, a method for treating hair, a method for treating dye house effluents and a method for decolorizing dyes by using the laccase enzyme of the present invention.

Still further objects of this invention are uses of laccase enzyme of the present invention in various applications and compositions.

By using the laccase enzyme of this invention in denim bleaching it is possible to obtain many advantages. By using the laccase enzyme of this invention it is possible to decrease or fully avoid the environmentally harmful effects of sodium hypochlorite. If sodium hypochlorite is not used, no antichlor treatment is required. It is also possible to obtain various shades as by hypochlorite bleaching. Even a very faded look of denim can be obtained. One advantage of the laccase treatment by using the enzyme of the invention is that the treatment does not destroy the fabric. The laccase can also be used for treating Lycra containing products. In addition, the laccase treatment is also convenient for the user. Furthermore, the enzyme can function at a broad temperature and pH range. Also in other applications remarkable benefits can be obtained.

Other features, aspects and advantages of the present invention will become apparent from the following description and appended claims.

BRIEF DESCRIPTION OF THE DRAWINGS

FIG. 5. The tryptic peptide sequences obtained from the purified *Thielavia arenaria* wt TaLcc1 and the possible codons to encode the sequences.

FIGS. 6 A and B. The nucleotide sequence of the *Thielavia arenaria* ALKO4197 Talcc1 gene and the deduced amino acid sequence. The stop codon is shown by an asterisk below the sequence. The location of the putative introns and the consensus intron splicing signals (5' GTPuNGPy, 3' PyAG, internal NNCTPuAPy) are marked by using lowercase letters and by bolding, respectively. The putative signal peptide, analyzed by SignalP V2.0 program, and the mature C-terminal amino acid sequence (determined from the purified recombinant TaLcc1 protein) are underlined. The location of the tryptic peptide sequences obtained from the purified wt TaLcc1 are marked by dotted lines below the sequence. The conserved residues involved in copper binding are highlighted. The sites for putative N-glycosylation (N-X-S/T) are bolded.

SEQUENCE LISTING

Figure 1:
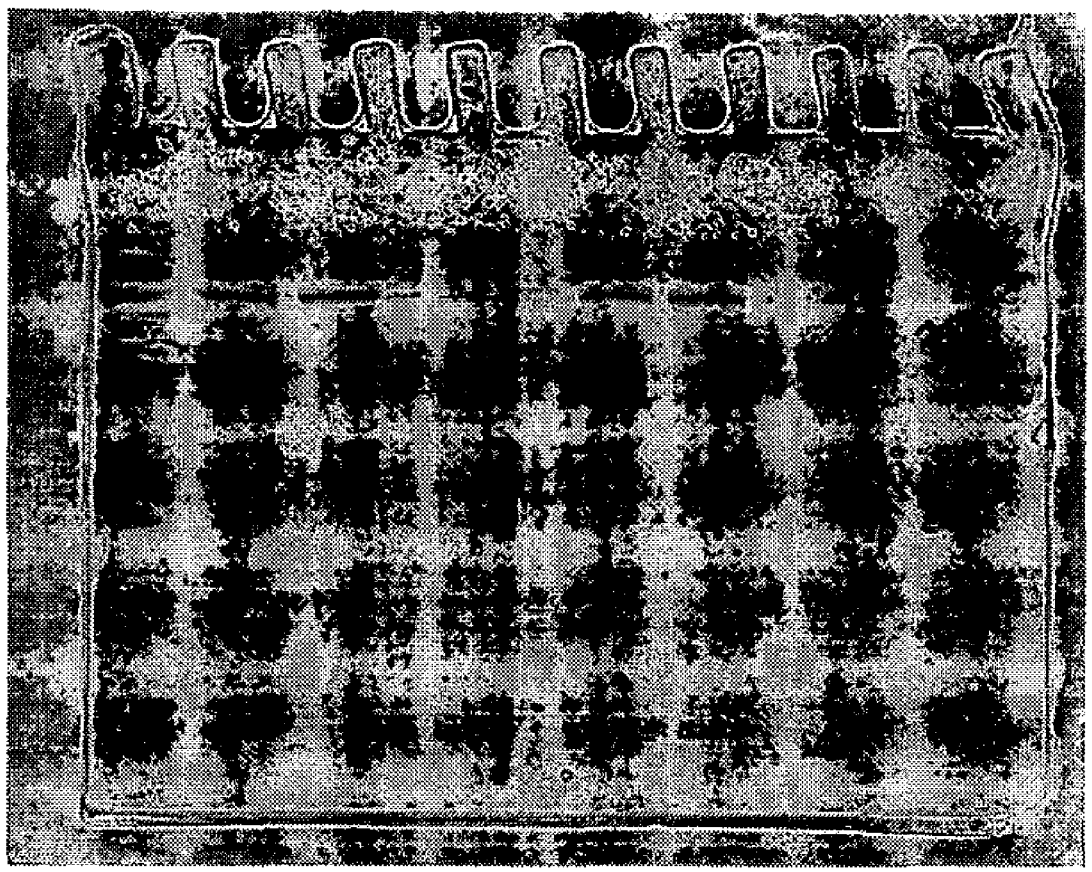
FIG. 1. SDS-PAGE (15%) showing the purification of *Thielavia* laccase (TaLcc1). Lanes: 1 MW marker (175, 83, 62, 47, 32.5, 25, 16.5, and 6.5 kDa), 2 culture supernatant, 3 fractions after DEAE Sepharose, 4-7 fractions after gel filtration, about 3-6 ug protein loaded on each lane. Proteins are stained with Coomassie Brilliant Blue.

SEQ ID NO: 1 Sequence of the Peptide 1, a tryptic peptide from *Thielavia arenaria* ALKO4197 TaLcc1 protein.
SEQ ID NO: 2 Sequence of the Peptide 2, a tryptic peptide from *Thielavia arenaria* ALKO4197 TaLcc1 protein.
SEQ ID NO: 3 Sequence of the Peptide 3, a tryptic peptide from *Thielavia arenaria* ALKO4197 TaLcc1 protein.
SEQ ID NO: 4 Sequence of the oligonucleotide primer POX26.
SEQ ID NO: 5 Sequence of the oligonucleotide primer POX27.
SEQ ID NO: 6 Sequence of the oligonucleotide primer POX28.
SEQ ID NO: 7 Sequence of the oligonucleotide primer POX29.
SEQ ID NO: 8 Sequence of the oligonucleotide primer POX30.
SEQ ID NO: 9 Sequence of the oligonucleotide primer POX31.
SEQ ID NO: 10 Sequence of the PCR fragment obtained using the primers POX27 and POX31.
SEQ ID NO: 11 Nucleotide sequence of the *Thielavia arenaria* ALKO4197 laccase 1 gene (TaLcc1).
SEQ ID NO: 12 Deduced amino acid sequence of the *Thielavia arenaria* ALKO4197 laccase 1 (TaLcc1).

Depositions

*Thielavia arenaria* ALKO4197 was deposited at the Centralbureau Voor Schimmelcultures at Upsalalaan 8, 3584 CT, Utrecht, the Netherlands on 2 Sep. 2004 and assigned accession number CBS 116071.

The *E. coli* strain RF5473 including the plasmid pALK1342 was deposited at the Deutsche Sammlung von Mikroorganismen und Zellkulturen GmbH (DSMZ), Mascheroder Weg 1 b, D-38124 Braunschweig, Germany on 7 Mar. 2003 and assigned accession number DSM 15484.

DETAILED DESCRIPTION

The present invention provides a laccase enzyme that is under suitable conditions, capable of increasing lightness of denim at least, or above, as many units as denim treated by chemical bleaching agent, in particular sodium hypochlorite.

By "the laccase of the present invention" or "the laccases of the present invention" is here meant the group of laccases as defined in the claims and described herein.

By "laccase enzyme" is in connection of this invention meant an enzyme classified as EC 1.10.3.2 by the enzyme classification. The laccase enzyme may originate from any organism including plants; preferably it may originate from microorganisms. It may originate from bacteria, for example from a genus selected from the group comprising *Bacillus*, *Azospirillum* and *Streptomyces*. Preferably the enzyme originates from fungi (including filamentous fungi and yeasts), for example from a genus selected from the group comprising *Thielavia*, *Chaetomium*, *Achaetomium*, *Aspergillus*, *Botrytis*, *Collybia*, *Fomes*, *Humicola*, *Hypocrea*, *Lentinus*, *Melanocarpus*, *Myceliophthora*, *Neurospora*, *Phlebia*, *Pleurotus*, *Podospora*, *Polyporus*, *Rhizoctonia*, *Scytalidium*, *Pycnoporus*, *Trametes* and *Trichoderma*.

According to a preferred embodiment of the invention the laccase of the present invention is obtainable from genus *Thielavia*, more preferably from *Thielavia arenaria*. According to a most preferred embodiment of the invention the enzyme is obtainable from a strain deposited at Centraalbureau voor Schimmelcultures under number CBS 116071.

The origin of the laccase of the present invention is not restricted to genus *Thielavia* or to the species *T. arenaria*. By using the description provided herein, a person skilled in the art can find and isolate laccase of the present invention from other genera of fungi, from other microorganisms and also from higher organisms, such as plants.

Laccase of the present invention can be isolated from any organism producing laccase. Preferably the laccase enzyme of the present invention is isolated from a microbial source. Organisms capable of producing laccase can be screened, the activity on various substrates can be determined, and the enzyme characterized. For example, the pH and temperature ranges where the enzyme functions, pH and temperature optima, and enzyme stability at various temperatures, can be determined. Alternatively, genes encoding laccases in various organisms can be isolated and the amino acid sequences encoded by the genes can be compared with the amino acid sequence of the laccase isolated and characterized in the Examples here. This includes direct cloning from environmental samples.

"Bleached look" means the effects, which are obtained on denim fabric in the prior art by means of bleaching chemicals, e.g. sodium hypochlorite. So far the "chlorine bleaching" has been the most effective bleaching method for denim dyed with Indigo since almost all shades have been obtained with it. If a "white bleaching" effect has been desirable, the bleaching has been carried out 2 to 3 times one after the other in different treatment baths, or by using high concentrations of hypochlorite. Bleaching with glucose, sulphinic acid derivatives or laccases have been suggested for denim treatment to replace sodium hypochlorite. However, in the prior art, with none of them the same effects have been obtained as with hypochlorite.

To "increase the lightness" of denim fabric, according to the prior art, treatment with various bleaching chemicals or enzymes is carried out. Bleaching is often done after treatment with cellulases or pumice stones, or both.

The "desizing" process is normally the first wet treatment of jeans and means the removal of starch or other sizing agents applied usually to the warp yarns to prevent damage during the weaving process. Alpha-amylases are used to remove starch-based size for improved and uniform wet processing. After desizing the jeans are normally rinsed with water.

The term "abraded" means here the appearance of denim fabric when it has been treated by cellulase enzymes or stone washed, or both. As a result of uneven dye removal there are contrasts between dyed areas and areas from which dye has been removed. Synonymous expressions are "stone washed look" or "worn look". The cellulase treatment may be done using neutral or acid cellulases or both. If a fabric is not cellulase treated or stone washed, the appearance of the fabric is said to be "dull", since the fashionable contrasts would be missing.

By "increasing lightness" of denim is here meant a visible and measurable increase in the lightness of denim fabric. The increase of lightness is measured as lightness unit L* of the fabric after laccase treatment minus lightness unit L* before laccase treatment. By "increasing lightness" of denim is meant in particular increasing lightness of denim on the face side of denim. The increase can be measured for example by measuring the colour as reflectance values with a spectrofotometer using L*a*b* color space coordinates as described in Examples 7-10.

The laccase enzyme of the present invention is capable, by single treatment, in suitable conditions, of increasing lightness of the face side of denim at least, or above, as many units as denim treated by sodium hypochlorite. The laccase treatment is made under conditions suitable for the function of the enzyme. The result of laccase treatment is compared with the result obtained with sodium hypochlorite under conventional bleaching conditions. As test conditions can be chosen the following bleaching conditions: fabric is treated in the presence of 25 ml/l of 10% sodium hypochlorite (NaOCl) solution, at the temperature 40° C., at pH above 10.5, the treatment time being 15 min. The liquor ratio is about 1:15. The treatment can be carried out in equipments normally used for wet processes in textile industry, such as washing machines. The exact test conditions are described in Example 10. After bleaching the remaining hypochlorite is removed e.g. by treatment with sodium metabisulphite or sodium thiosulphate, followed by several rinsing/washing steps.

Compared to the result obtained under the mentioned sodium hypochlorite test conditions, the laccase enzyme of the present invention increases in suitable conditions, by single treatment, the lightness of desized denim of the face side of denim at least as many units as sodium hypochlorite. By "desized" is here meant "only desized", not cellulase treated. If laccase treatment is made on desized and cellulase treated denim, the increase of lightness is typically 20 to 70%, preferably 40 to 115% more than denim treated under test conditions by sodium hypochlorite.

With the laccase of the present invention it is possible, in a single treatment and under suitable conditions, to obtain lightness value (L*), on the face side of denim, from 47 to 50 or even higher, when Indigo dyed, cellulase treated denim with lightness value (L*) on the face side of denim lower than 32 is used.

With the laccase of the present invention it is possible, in a single treatment and under suitable conditions, to obtain increase of lightness value (L*), on the face side of denim, from 17 to 25 units or even higher, when Indigo dyed, cellulase treated denim with lightness value (L*) on the face side of denim lower than 32 is used.

By treating denim fabric with the laccase of the present invention it is possible to obtain a bleaching effect akin to what is obtained with sodium hypochlorite. If more whitish effect is desired, higher dosages can be used or the enzyme treatment can be repeated or combined with other bleaching methods. The laccase treatment of the present invention can be combined also with any other bleaching treatment, with one or more chemical bleaching treatments or with one or more other enzyme treatments having capability of increasing lightness of denim.

By "mediators" are here meant additives, which are often needed for enhancing the effect of laccases. Many of the prior art laccases do not function or do not function effectively in the absence of mediators. Also the laccase originating here from *Thielavia* functions more effectively in the presence of mediators. Suitable mediators include, for example methylsyringate, acetosyringon, ethylsyringate, butylsyringate and laurylsyringate, propionic acid-phenothiazine (PPT) 2,2'azinobis-3-ethylbenzthiazole-6-sulphonate (ABTS), 2,2,6,6-tetramethyl-1-piperidinyloxy (Tempo), 1-hydroxybenzotriazole (HBT), violuric acid, N-hydroxy-acetanilide (NHA). The mediator may be used in the range 0.1 to 100 mg/g or 0.1 to 100 mg/l, preferably 1 to 10 mg/g or 1 to 10 mg/l of the treated material depending on the application and on the mediator.

With the laccase enzyme of the present invention any kind of denim fabric can be treated. Advantageously the denim is Indigo dyed denim. Denim can also be treated with derivatives of Indigo or denim dyed with Indigo together with some other dye, for example indigo-dyed denim with sulphur bottom. The denim fabric may be cellulase treated or stone washed, or both, or the denim fabric may be treated by laccase of the present invention already after desizing.

According to a preferred embodiment of this invention denim treatment by the laccase of the present invention is carried out at the temperature of 30 to 80° C., preferably at the temperature of 50 to 70° C., more preferably at the temperature of 60 to 70° C. The pH during the treatment may be in the range from pH 3.5 to 8, preferably from pH 4 to 7.5, most preferably from pH 5 to 7. The treatment may be carried out in 15 minutes to 2 hours, preferably in 30 minutes to 90 minutes, more preferably in 30 minutes to 60 minutes. The dosage used in the treatment can be 2 to 500 nkat, more preferably 20 to 200, most preferably 20 to 100 nkat/g fabric.

The denim treatment according to the invention comprises generally the following steps:
    desized or optionally desized and cellulase treated denim is contacted in aqueous medium with an effective amount of laccase enzyme under suitable conditions for the function of the enzyme; and
    one or more rinses with water are carried out.

The laccase treatment is preferably carried out on cellulase treated denim. Laccase treatment is followed by one or more rinses with hot or cold water optionally with detergents. Enzyme inactivation is usually not needed after laccase treatment since it does not reduce the strength of fabric, but if needed it can be carried out by methods well known to a person skilled in the art. The treatment is typically carried out in equipment normally used for wet processes in textile industry, such as industrial machines used for washing, cellulase treatment, dyeing or finishing.

By "denim" is in connection of this invention meant denim fabric, usually denim jeans.

Performance of the laccase preparation of the present invention in denim bleaching was exemplified at different pH-values as described in the Example 7. Recombinant laccase preparation produced using *Thrichoderma* as a host was tested for its ability to bleach denim and compared to a commercial laccase preparation DeniLite II Base from Novozymes.

Figure 8:
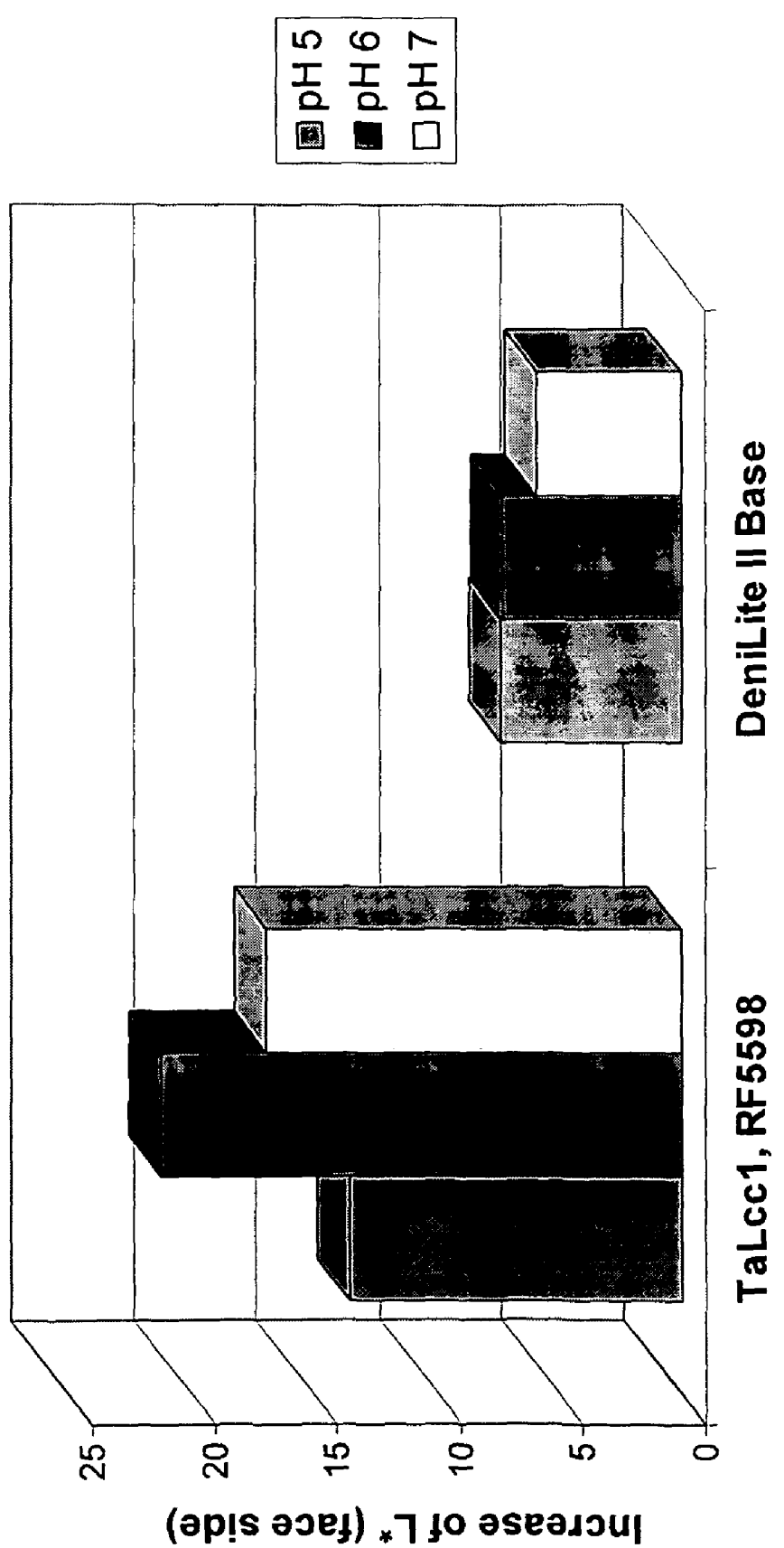
FIG. 8. The performance of TaLcc1 laccase preparation in denim bleaching at different pH values compared to DeniLite II Base. The enzyme dosage was 200 nkat/g and mediator dosage 10 mg/g on the weight of the fabric.

The laccase of the present invention was superior in decolorisation of indigo dye of denim compared to the prior art laccase at all pH values from 5 to 7, pH 6 being the optimum as can be seen in Table 10 and in FIG. 8. Only the laccase preparation of the present invention was capable of achieving a strongly bleached look with the highest lightness value. In addition, the abraded look obtained by cellulase treatment was maintained. The increase of lightness and the decrease of blueness on the reverse side of denim was also the highest with denim treated with the laccase preparation of the invention with the mediator.

The ability of the laccase of the present invention to bleach denim at different temperatures was tested and compared to the prior art laccase as described in Example 8.

Figure 9:
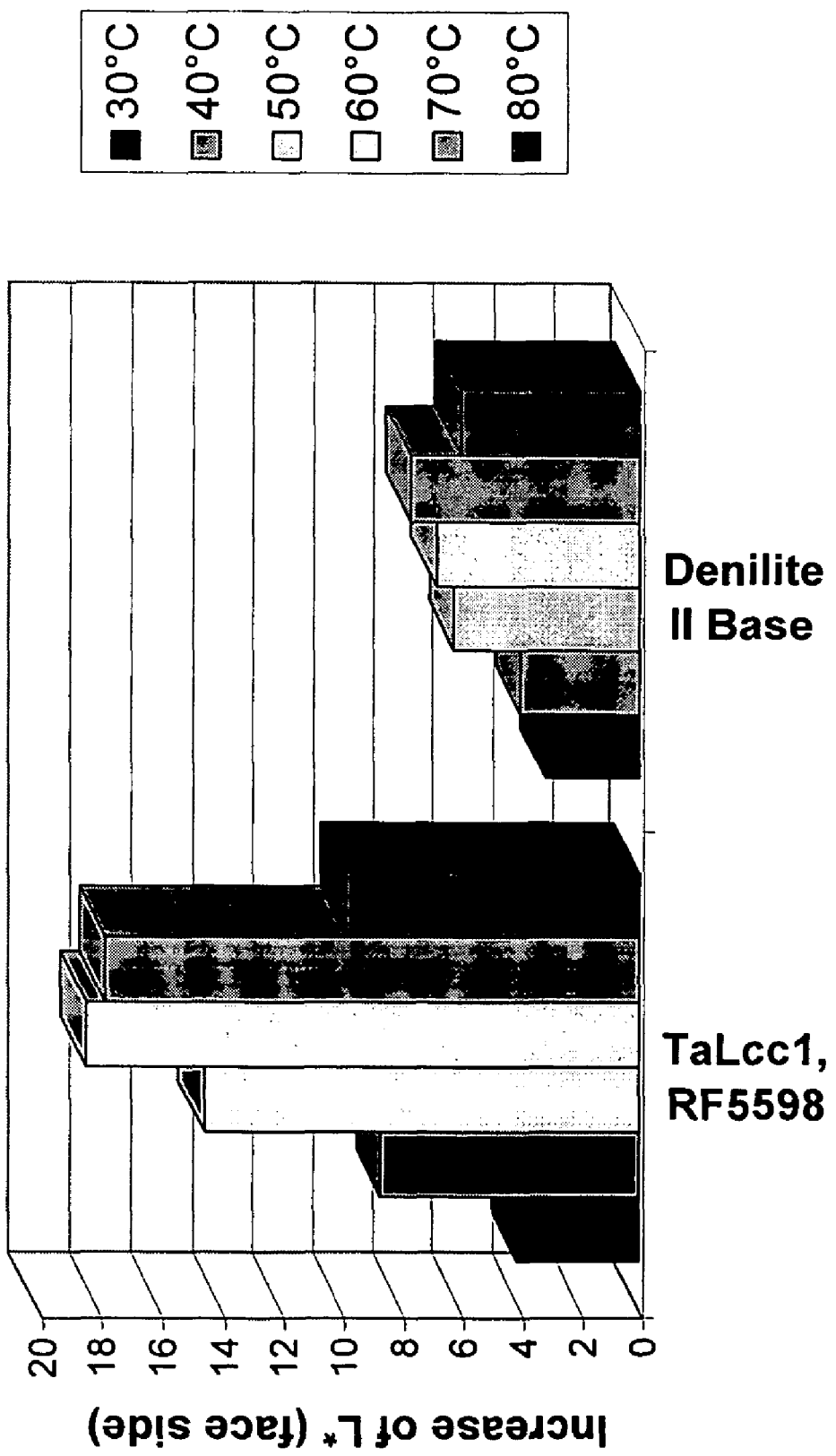
FIG. 9. Performance of TaLcc1 laccase preparation in denim bleaching at different temperatures compared to DeniLite II Base. The enzyme dosage was 200 nkat/g and mediator dosage 10 mg/g on the weight of the fabric.

The laccase preparation of the present invention was superior in bleaching of denim (higher increase of lightness) compared to the prior art laccase at 30 to 80° C. as can be seen in Table 12 and in FIG. 9. The temperature 60 to 70° C. was the most optimal for the laccase of the present invention and the look of the denim fabric was strongly faded.

Effect of enzyme dosage on bleaching of denim was studied with laccase-mediator system as is described in Example 9. Cellulase treated denim jeans were treated with recombinant laccase product from *Trichoderma* strain and the prior art laccase using different laccase dosages. The increase of the dosage from 20 to 100 nkat/g of fabric greatly improved the bleaching with the enzyme of the present invention. Increasing the time from 30 min to 60 min further improved the performance of the laccase of the present invention as can be seen in Table 14 and in FIG. 10.

Bleaching of denim with laccase-mediator system was compared to bleaching with hypochlorite as is described in Example 10. Different types of denim were treated with the laccase of the present invention and the prior art laccase and the results obtained were compared to hypochlorite bleaching. Denim samples washed with cellulase after desizing to different abrasion levels or only desized samples were used in the test. The laccase of the present invention was superior compared to the prior art laccase and chlorine bleaching with all cellulase treated denim samples of each type as can be seen in Tables 18-20 and in FIGS. 11 A to D. With fabrics that had only been desized the bleaching effect (increase of L* on the face side of denim) obtained with *Thielavia* laccase preparation was equal or better than with the sodium hypochlorite and at least 100% better than with the prior art laccase (Denilite II Base). With the laccase of the present invention it was possible to achieve a very strong bleaching effect that is normally obtained only with the use of high amounts of sodium hypochlorite.

Microorganisms that produce the laccase of the present invention can be isolated from nature or they can be screened from already isolated and identified strains of culture collections by using screening methods that are well known for a person skilled in the art. Screening can be carried out by studying the production of the enzyme either on a solid culture on plate cultivations or in a liquid culture medium by measuring the enzyme activity. Suitable substrates for measuring the activity include ABTS, di-methoxyphenol (DMP), guaiacol, and syringaldazine. Fungi can be screened for their ability to produce laccases for example by the methods referred in Example 1 with indicators, such as Remazol Brilliant Blue R-478, tannic acid, and guaiacol. Suitable laccases can be isolated and the genes encoding them can be cloned also from higher organisms, such as plants.

This invention relates to enzymes which have high oxidizing capacity of various substrates and is thus suitable for different applications. In particular, this invention relates to enzymes having the specific activity of at least 800 nkat/mg, more preferably at least 900 nkat/mg on ABTS at pH 4.5. When syringaldazine is used as subtrate the specific activity is at least 200, preferably at least 300 nkat/mg at pH 5.5. When guaiacol is used as substrate the specific activity of the enzyme is at least 40 nkat/mg, preferably at least 60 nkat/mg at pH 5.5.

Microorganism strains, which are found as a result of screening, can be cultivated on a suitable medium, and the formation of laccase in the culture solution or plate can be observed. After a sufficient amount of an interesting laccase has been produced, the enzyme can be purified and its properties can be more thoroughly characterized.

The produced laccase enzymes can be purified by using conventional methods of enzyme chemistry, such as salt precipitation, ultrafiltration, ion exchange chromatography, and hydrophobic interaction chromatography. Purification can be monitored by protein determination, enzyme activity assays and by SDS polyacrylamide gel electrophoresis. The enzyme activity of the purified enzyme at various temperatures and pH values can be determined; similarly, the molecular weight and the isoelectric point can be determined.

The purified enzyme refers to an enzyme preparation, which has no other proteins or very low amount of other proteins in addition to the laccase protein. The purity of the obtained laccase that is essentially free from other proteins is ≧90%.

The purification of a preferred laccase of the present invention has been exemplified in Example 1. Concentrated culture filtrate was loaded on Q Sepharose FF column, proteins were eluted with an increasing salt gradient and laccase active fractions were loaded on Sephacryl S100 gel filtration resin. Purification was followed by activity assays and by SDS-PAGE. In order to obtain high purity samples an additional Resource Q anion exchange step was included. Naturally, it is possible to separate the enzyme of the present invention by using other known purification methods instead, or in addition to the methods described here.

The isoelectric point of the laccase can be determined with isoelectric focusing and bands containing laccase activity can be visualized by staining the gel with ABTS, for example, as described in Example 2.

Determination of laccase activity at various temperatures can be carried out by the ABTS method, as described in Example 1 in accordance with the method developed by Niku-Paavola et al. (1988) or by other methods described in literature.

The pH optimum of the laccase can be determined in a suitable substrate in a suitable buffer at different pH values by following the activity.

The thermal stability can be determined by incubating an enzyme sample at various temperatures in a suitable buffer at a certain pH. The residual activity of the enzyme at each temperature can be defined by the ABTS method, for example.

Specific activities of the purified laccase can be determined towards different laccase substrates, such as ABTS, di-metoxy-phenol (DMP), syringaldazine, and guaiacol.

The effect of various inhibitors on laccase activity can be determined by measuring the oxygen consumption during the enzyme reaction with ABTS, for example, in sealed and filled containers with oxygen electrode or following the enzyme activity by spectroscopic means in the presence of an inhibitor.

The N-terminus of the protein as well as the internal peptides can be sequenced according to Edman degradation chemistry [Edman P. and Begg G. (1967)] as described in Example 2 or by other methods described in the literature.

The molecular weight of the purified laccase enzyme isolated from *Thielavia arenaria* RF5597 was approximately 80 kDa. The purified laccase showed multiple bands in isoelectric focusing at pIs 5.5, 5.9, 6.4, 6.8, and 6.9.

The pH optimum for the purified laccase was 5.5, determined on guaiacol, and the enzyme showed substantially high activity still at pH 7. The enzyme functions at pH range from 3.5 to 8, preferably from 4 to 7.5 and most preferably at 5 to 7. The accurary of the measurement is ±0.5.

The first pH range (pH 3.5 to 8) means that 20% or more of the maximal activity is within this range, the second pH range (pH 4 to 7) means that 40% or more of the acitivity is within this range. The third region (pH 5 to 7) means that 80% or more of the activity is within this range.

The half life of the laccase was 26 hr at 50° C. and 5.5 at 60° C. in the assay conditions.

The temperature optimum of the laccase in the denim bleaching application was 60° C. The enzyme functions at the temperatures 18 to 80° C., although effectively at temperatures 30 to 80° C., more preferably at temperatures 50 to 70° C., most preferably at the temperatures 60 to 70° C.

The specific activity of the enzyme was the highest on ABTS, 1020 nkat/mg of protein at pH 4.5. The specific acitivity on DMS was 260, on syringaldazin 490 and on guaiacol 63 nkat/mg at pH 5.5.

The laccase which shows advantageous properties may be either produced by the original or recombinant host by a method comprising cultivating under suitable conditions a host into which a DNA sequence encoding said laccase and sequences needed for expressing said enzyme, has been introduced, and optionally isolating the enzyme. The production host can be any organism capable of expressing the laccase. Preferably the host is a microbial cell, more preferably a fungus. Most preferably the host is a filamentous fungus. Preferably the recombinant host is modified to express and secrete laccase as its main activity or one of its main activities. The spent culture medium of the production host can be used as such, or the host cells may be removed, and/or it may be concentrated, filtrated or fractionated. It may also be dried.

Suitable expression and production host systems are for example the production system developed for the fungus host *Trichoderma* (EP 244 234), or *Aspergillus* production system, such as *A. oryzae* or *A. niger* (WO 9708325 and WO 9533386, U.S. Pat. Nos. 5,843,745, 5,770,418), or the production system developed for *Fusarium*, such as *F. oxysporum* (Malardier et al., 1989) or for *Chrysosporium* (U.S. Pat. No. 6,573,086). Suitable production systems developed for bacteria are a production system developed for *Bacillus*, for example *B. subtilis* or for *E. coli*, or for actinomycete *Streptomyces*. Suitable production systems developed for yeasts are systems developed for *Saccharomyces*, *Shizosaccharomyces* or *Pichia pastoris*. Production systems in some other microbes or in mammalian cell are also possible.

Preferred hosts for producing laccase enzyme of the present invention are in particular strains from genus *Trichoderma* or *Aspergillus*.

Within the scope of protection are also vectors which can be used when the nucleic acid sequence encoding the chosen laccase are introduced into a host and sequences facilitating the expression and secretion of the laccase encoding sequence, such as promoters and signal sequences.

Standard molecular biology methods can be used in the cloning of the laccase enzyme i.e. in the isolation and enzyme treatments of DNA, in *E. coli* transformations, etc. The basic methods used are described in the standard molecular biology handbooks, e.g. Sambrook et al. (1989) and Sambrook and Russell (2001).

Genomic library prepared from the chosen host organism was screened with probes prepared by PCR. The sequences of the oligonucleotide primers used in the PCR reactions based on the amino acid sequences of the peptides obtained from the purified laccase enzyme produced by the natural host and on the concensus sequences of fungal laccases. The DNA products obtained were characterized by sequencing and by performing Southern blot hybridizations to the genomic *Thielavia* DNA digested with several restriction enzymes.

The full-length *Thielavia* laccase gene was included in the plasmids pALK1607, pALK1341 and pALK1342. The *E. coli* strain RF5473 including the plasmid pALK1342 was deposited to the DSMZ collection (DSM 15484). The deduced amino acid sequence of the laccase was analyzed from the DNA sequence.

The *Thielavia* laccase Talcc1 sequence (SEQ ID NO: 11) and the deduced amino acid sequence (SEQ ID NO: 12) are shown in FIG. 6. The length of the gene was 2279 bp (including the stop codon). The deduced protein sequence consisted of 617 amino acids including a predicted signal sequence of 21 amino acids and a "tail" sequence of 13 amino acids (starting after the sequence DSGL). The peptides purified from the wild type laccase were all found from the deduced amino acid sequence indicating that the gene cloned encodes the laccase purified from the recombinant host. The predicted molecular mass was 64456 Da for the mature polypeptide and the predicted pI was 6.31 (amino acids 22-604, signal sequence and the C-terminal tail removed). The deduced amino acid sequence included nine putative N-glycosylation sites. The homologies to the published laccase sequences were searched using the BLAST program, version 2.2.9 at NCBI (National Center for Biotechnology Information) (Altschul et al., 1990). The highest homologies were found to the laccases from *Melanocarpus albomyces, Podospora anserina* and *Neurospora crassa* (EMBL accession numbers CAE00180.1, LAC2_PODAN, XP_323881.1). The TaLcc1 sequence was aligned with the sequences with identity above 50% in the BLAST search and with the laccase sequences from *Myceliophthora thermophila* (EP 0765394 B1, corresponding U.S. Pat. No. 5,981,243) and *Scytalidium thermophilum* (U.S. Pat. No. 5,570,388). The highest identity, 73.1%, was found with *Melanocarpus albomyces* laccase.

By the term "identity" is here meant the identity between two amino acid sequences compared to each other from the first amino acid encoded by the corresponding gene to the last amino acid. The identity of the full-length sequences is measured by using Needleman-Wunsch global alignment program at EMBOSS (European Molecular Biology Open Software Suite; Rice et al., 2000) program package, version 2.9.0, with the following parameters: EMBLOSUM62, Gap penalty 10.0, Extend penalty 0.5.

Within the scope of the present invention are enzymes or polypeptides which comprise amino acid sequences which have laccase activity and which show at least 74% identity to the amino acid sequence SEQ ID NO: 12. Preferred enzymes comprise amino acid sequences which show at least 76%, more preferably at least 78%, even more preferably at least 80% identity. Still more preferable the amino acid sequences show at least 85%, more preferably at least 90%, most preferably at least 95% identity to the amino acid sequence SEQ ID NO: 12.

Within the scope of the present invention are also enzymes and truncated polypeptides as defined above, but which lack signal sequence or tail or both. The signal sequence or the tail or both may be cut for example during posttranslational phases of the production or in the spent culture medium or during the storage of the culture medium or enzyme preparation. In addition, a propeptide from the protein may be cleaved by the host. The truncation can also be achieved e.g. by shortening the gene encoding the polypeptide prior to transforming it to the production host.

The laccase according to the invention can be produced to the culture medium of its natural host or a recombinant host, from where it can be isolated and purified by using known methods of protein chemistry. If the culture medium contains a sufficiently high amount of laccase but no other detrimental proteins, it is possible to use the culture solution as such by simply separating the cells. When so desired, the culture solution can be concentrated, filtrated, fractionated and/or purified. It may also be dried. It is preferable to use, in various applications, an enzyme preparation containing an increased amount of laccase. Such an enzyme preparation can be prepared by producing the increased amount of laccase enzyme in the culture medium of the production host by means of gene technology or by optimising the cultivation conditions. The increased amount refers to an amount of laccase enzyme, which exceeds the amount of laccase enzyme naturally produced by the natural host.

According to a preferred embodiment of the invention *Thielavia* laccase can be produced in a filamentous fungus host, preferably in a *Trichoderma* host. The production is described in more detail in Example 4. The purified recombinant laccase was characterized in terms of pH optimum, thermal stability, and pI, which clearly indicated that the recombinant laccase has similar properties as the wild type *Thielavia* laccase.

The production of laccase can also be improved by optimising the culture conditions and the culture medium of a wild or a recombinant strain. The carbon/nitrogen ratio can be optimised to be the best for the production of enzyme. The growing conditions, pH, temperature, mixing and air supply can be optimised to be the best possible for the enzyme production in question. In fermentation, inducers of laccase production, such as veratryl alcohol, xylidine, or lignin can also be used. The way and the time of adding the inducers, as well as their concentration can be optimised.

The term "enzyme preparation" denotes here to any enzyme product, which contains at least one laccase enzyme. Thus, such an enzyme preparation may be a spent culture medium or filtrate containing one or more laccases or one or more laccases and other enzymes, an isolated laccase enzyme or a mixture of one or more laccase enzymes or a mixture of one or more laccase enzymes and one or more other enzymes. In addition to the laccase activity, such a preparation may contain additives, such as mediators, stabilizers, buffers, preservatives, surfactants and/or culture medium components. Preferred additives are such, which are commonly used in enzyme preparations intended for the application, where the enzyme preparation is used. The enzyme preparation may be in the form of liquid, powder or granulate.

By "spent culture medium" is here meant the culture medium of the host comprising the produced enzymes. Preferably the host cells are separated from the said medium after the production.

The enzyme preparation may comprise in addition to laccase, one or more other enzymes, which may be for example amylases, cellulases and/or peroxidases. Alternatively, before, during or after the laccase treatment of the present invention, another enzyme treatment may be carried out. The enzyme treatment may comprise, for example, one or more amylase treatments, one or more cellulase treatments and/or one or more peroxidase treatments. Which other enzymes are included to the enzyme preparation or are used in the enzyme treatment, depends on the application.

The enzyme preparation may comprise one or more laccase enzymes of the present invention or other laccase enzymes together with one or more laccase enzymes of the present invention. For example, laccase enzymes having different properties may be combined to make the enzyme preparation more useful for different conditions.

The laccase enzyme of the present invention can be used in stain removal under similar conditions as in denim bleaching.

According to a preferred embodiment of this invention stain removal is carried out at the temperature of 30 to 80° C., preferably at the temperature of 50 to 70° C., more preferably at the temperature of 60 to 70° C. The pH during the treatment can be from pH 3.5 to 8, preferably from pH 4 to 7.5, most preferably from pH 5 to 7. The treatment may be carried out in 15 minutes to 2 hours, preferably in 30 minutes to 90 minutes, more preferably in 30 minutes to 60 minutes. The dosage used in the treatment can be 0.2 to 2000 nkat/g, preferably 1 to 500 nkat/g, more preferably from 2 to 200 nkat/g on the weight of fabric.

The laccase of the present invention and DeniLite II Base laccase preparations were tested for their ability to remove stains as is described in Example 11. In the tests artificially soiled test cloths for grass soiling and for tea soiling were used with or without the mediator. The dosages of the enzyme were 20 and 200 nkat/g of fabric and the test was run at 40, 50 or 60° C. and pH 6 for 60 min.

Figure 12A:
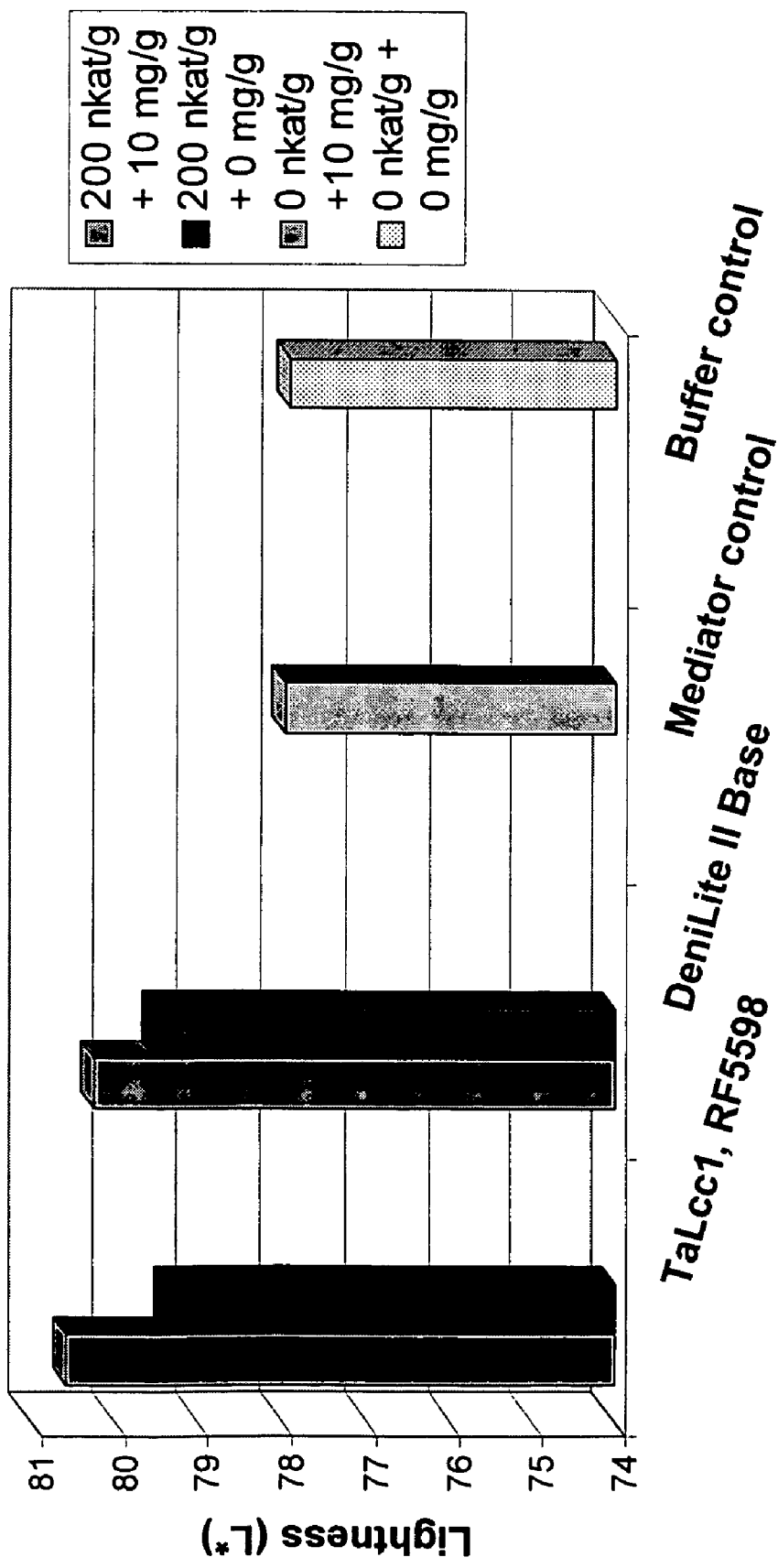
FIGS. 12 A and B. Effect of TaLcc1 laccase preparation on grass soiling at 60° C. compared to DeniLite II Base. The treatment was performed at pH 6 for 60 min. A. Lightness values, B. a* values (−a* is the green direction, +a* is the red direction).
Figure 12B:
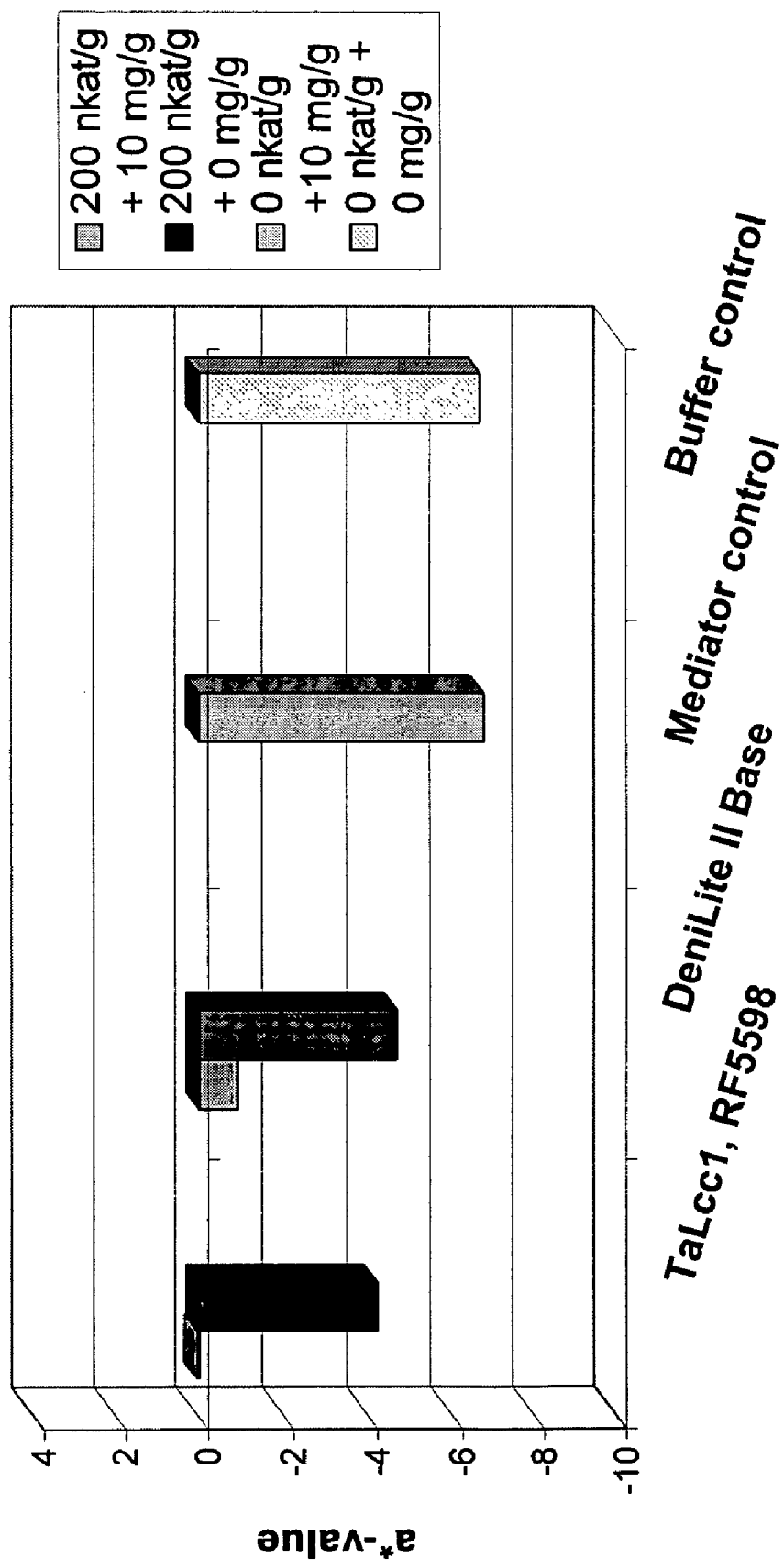

The laccase preparation of the present invention was more effective in removal of grass soiling with the mediator at 60° C. compared to the prior art laccase as can be seen in Table 21 and in FIGS. 12 A and B. The laccase of the present invention was also better at 40° C. as can be seen in Table 22 and in FIGS. 14 A and B. Mediator was needed to obtain the desired effect.

Figure 13A:
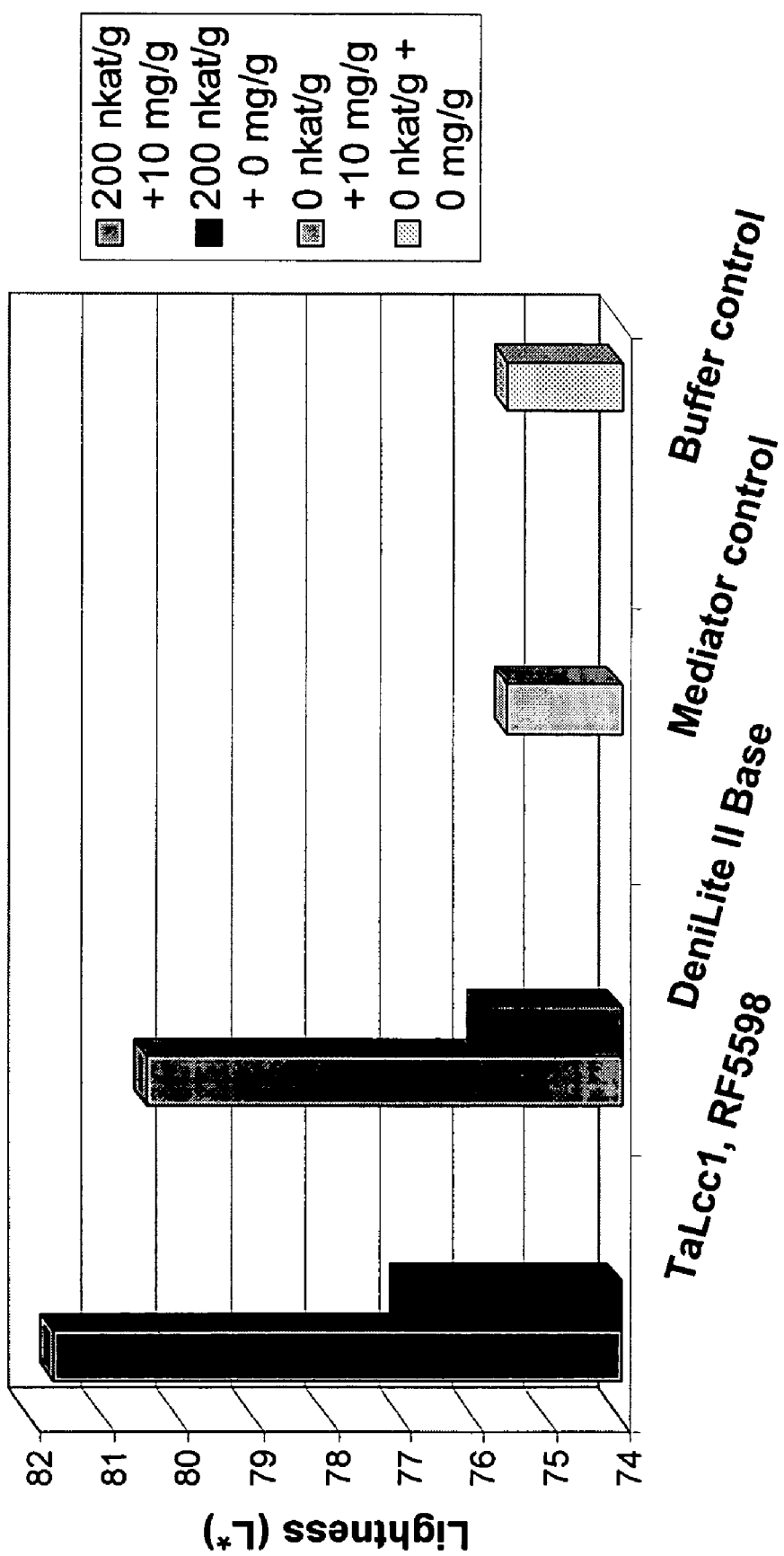
FIGS. 13 A and B. Effect of TaLcc1 laccase preparation on tea soiling at 60° C. compared to DeniLite II Base. The treatment was performed at pH 6 for 60 min. A. Lightness values, B. a* values (−a* is the green direction, +a* is the red direction).
Figure 13B:
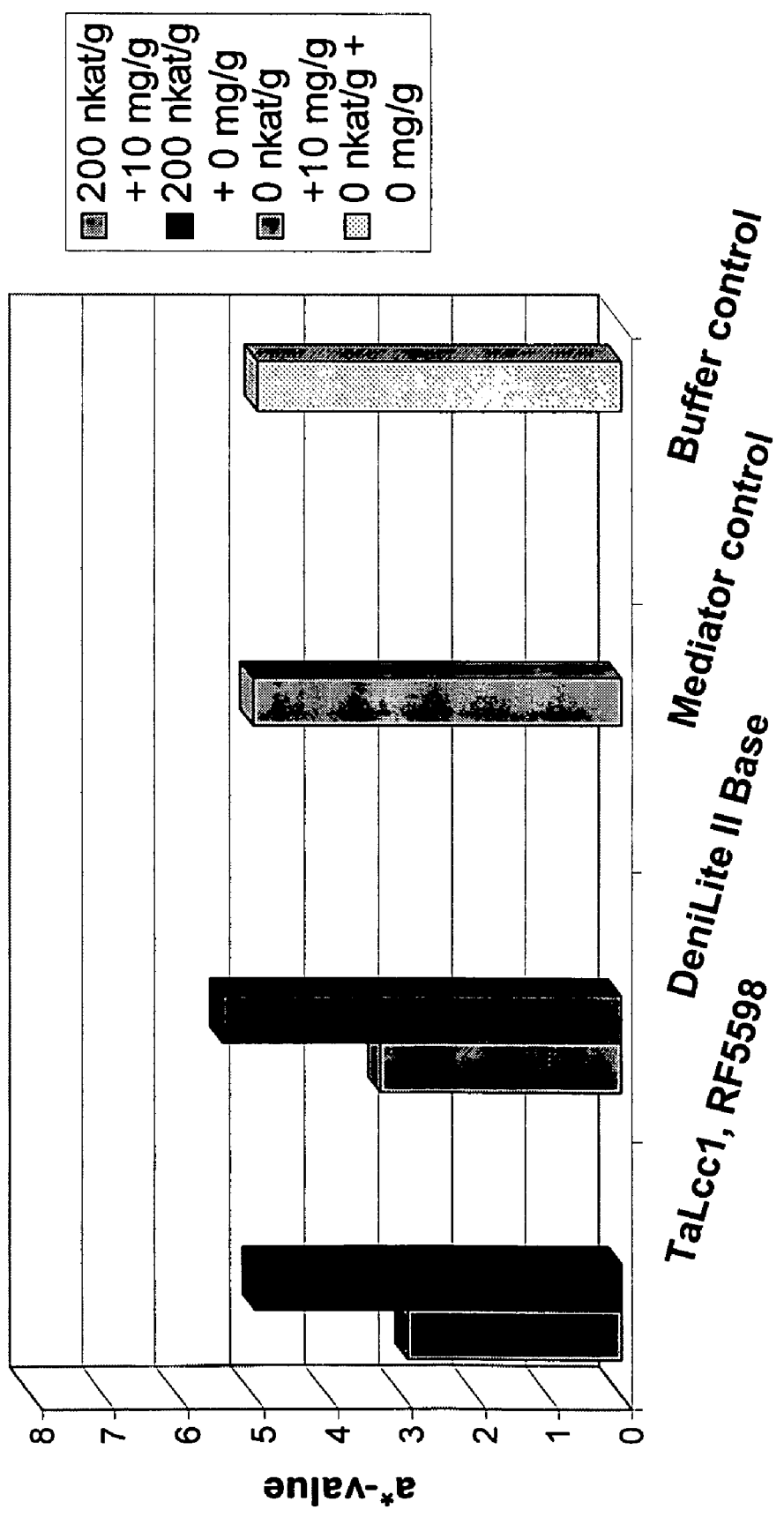
Figure 15A:
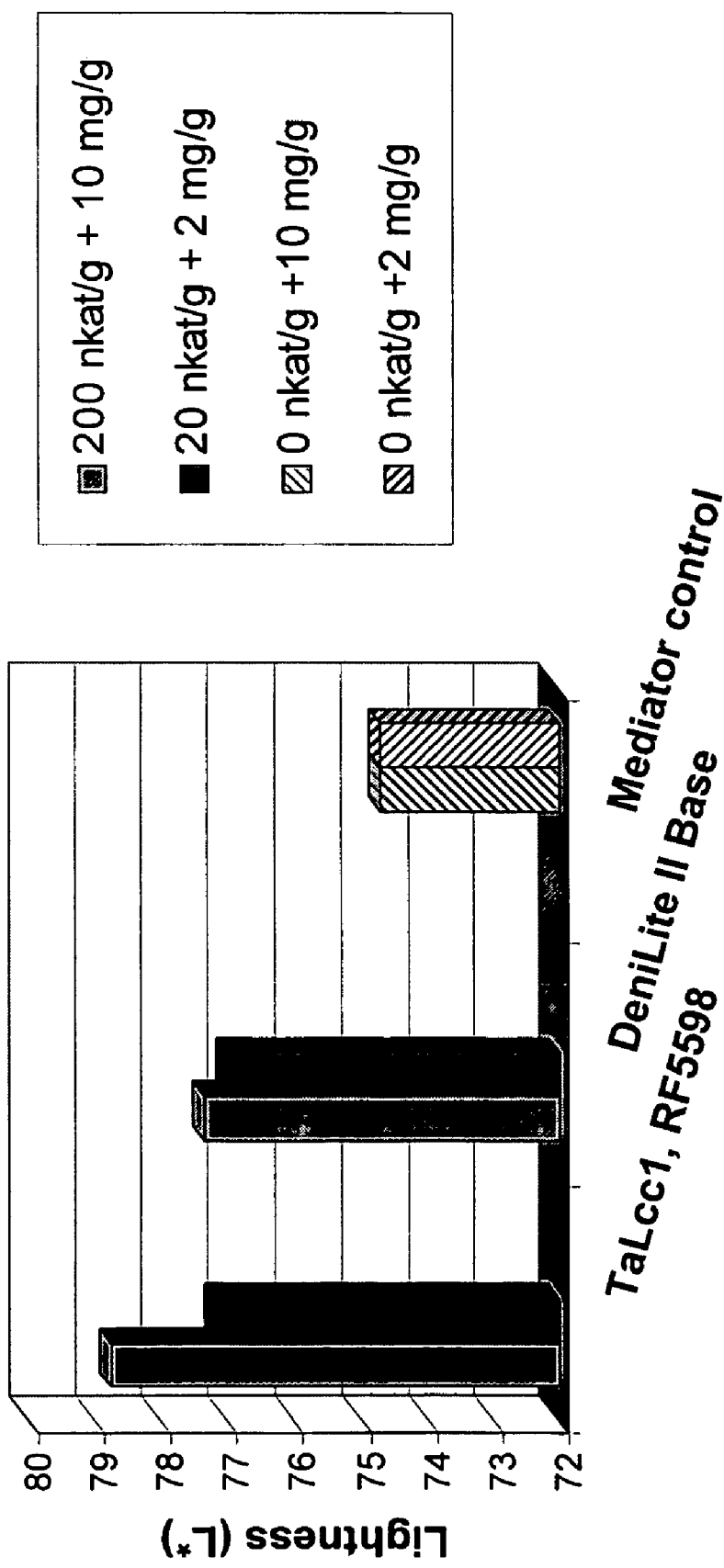
FIGS. 15 A and B. Effect of TaLcc1 laccase preparation on tea soiling at 40° C. with different dosages. The treatment was performed at pH 6 for 60 min. DeniLite II Base and mediator controls were used for comparison. A. Lightness values. B. a* values (−a* is the green direction, +a* is the red direction).
Figure 15B:
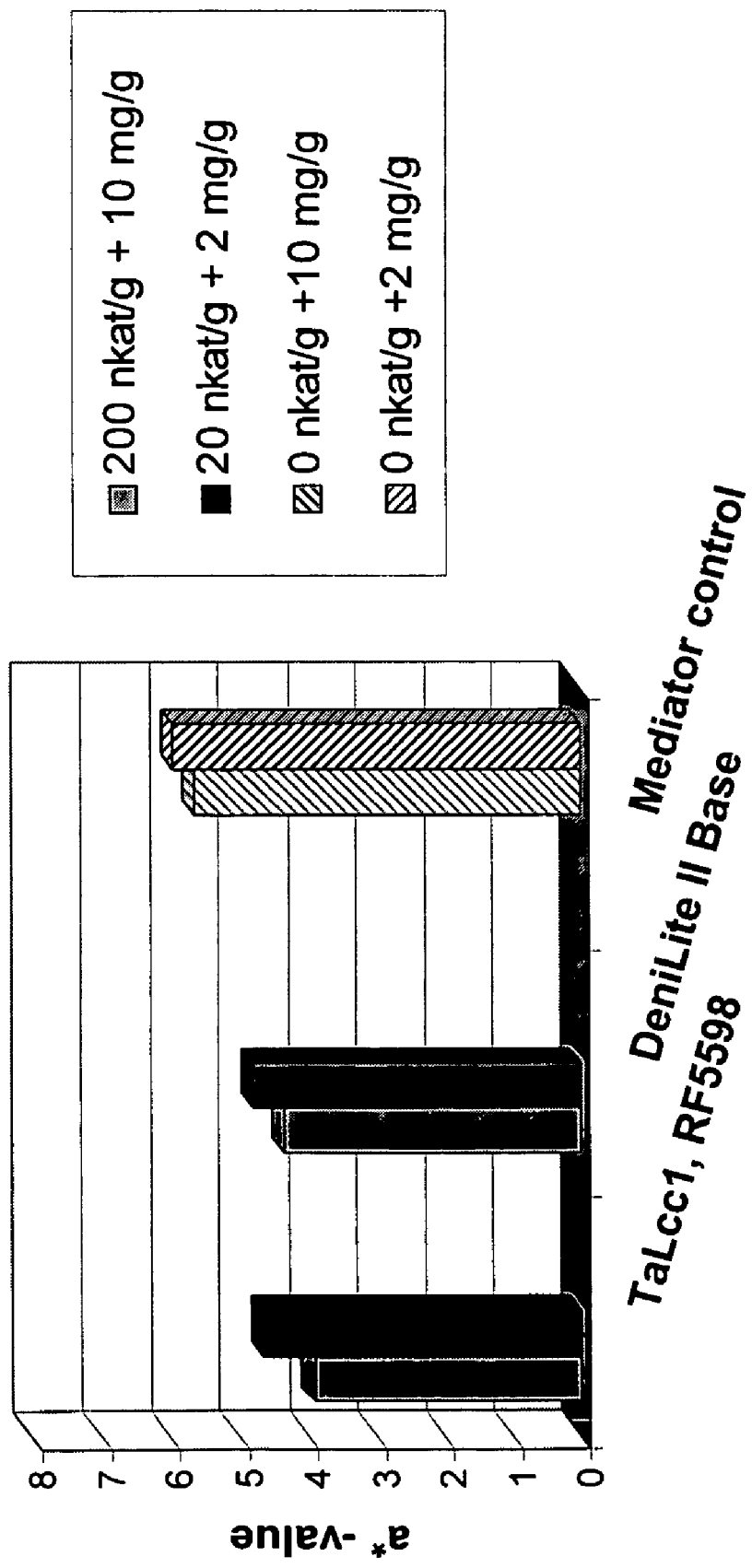

The laccase of the present invention was also the more efficient in removal of tea stain with the mediator at 60° C. and slightly better even at 40° C. especially with higher dosage as can be seen in Tables 21 and 22 and in FIGS. 13 A and B and in FIGS. 15 A and B. Mediator was needed to obtain the desired effect.

Figure 14A:
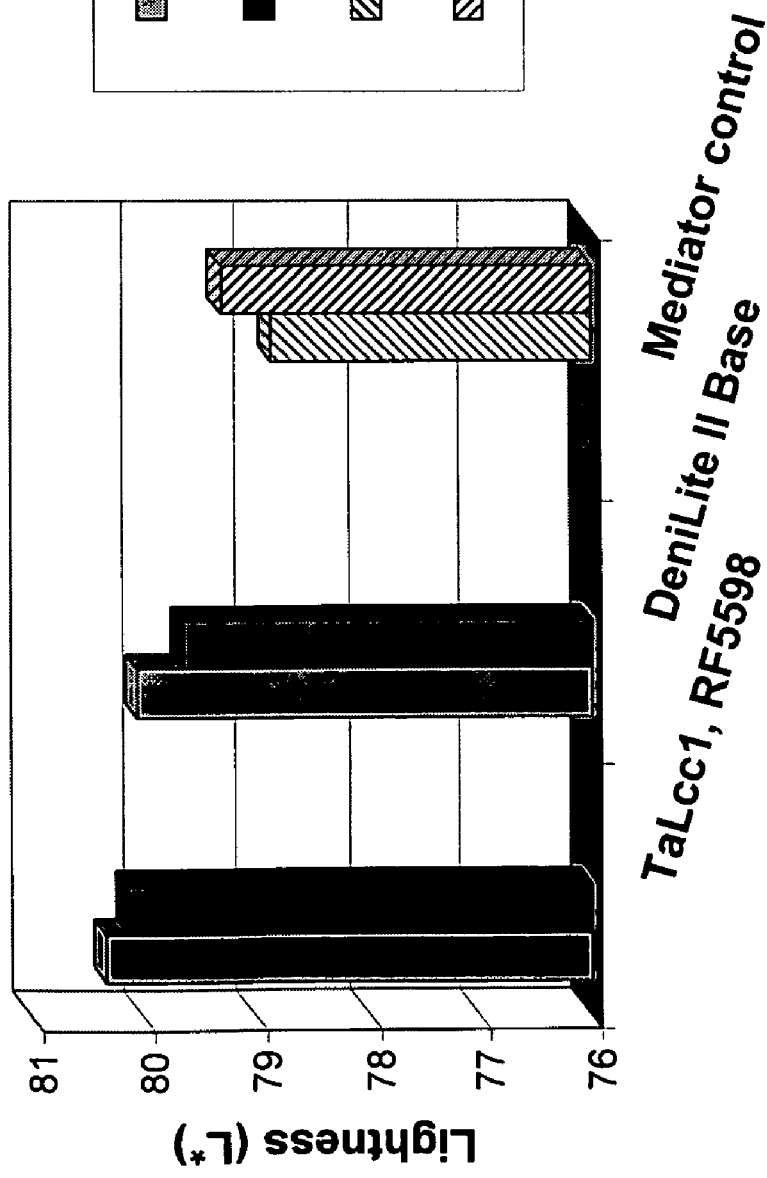
FIGS. 14 A and B. Effect of TaLcc1 laccase preparation on grass soiling at 40° C. with different dosages. The treatment was performed at pH 6 for 60 min. DeniLite II Base and mediator controls were used for comparison. A. Lightness values. B. a* values (−a* is the green direction, +a* is the red direction).
Figure 14B:
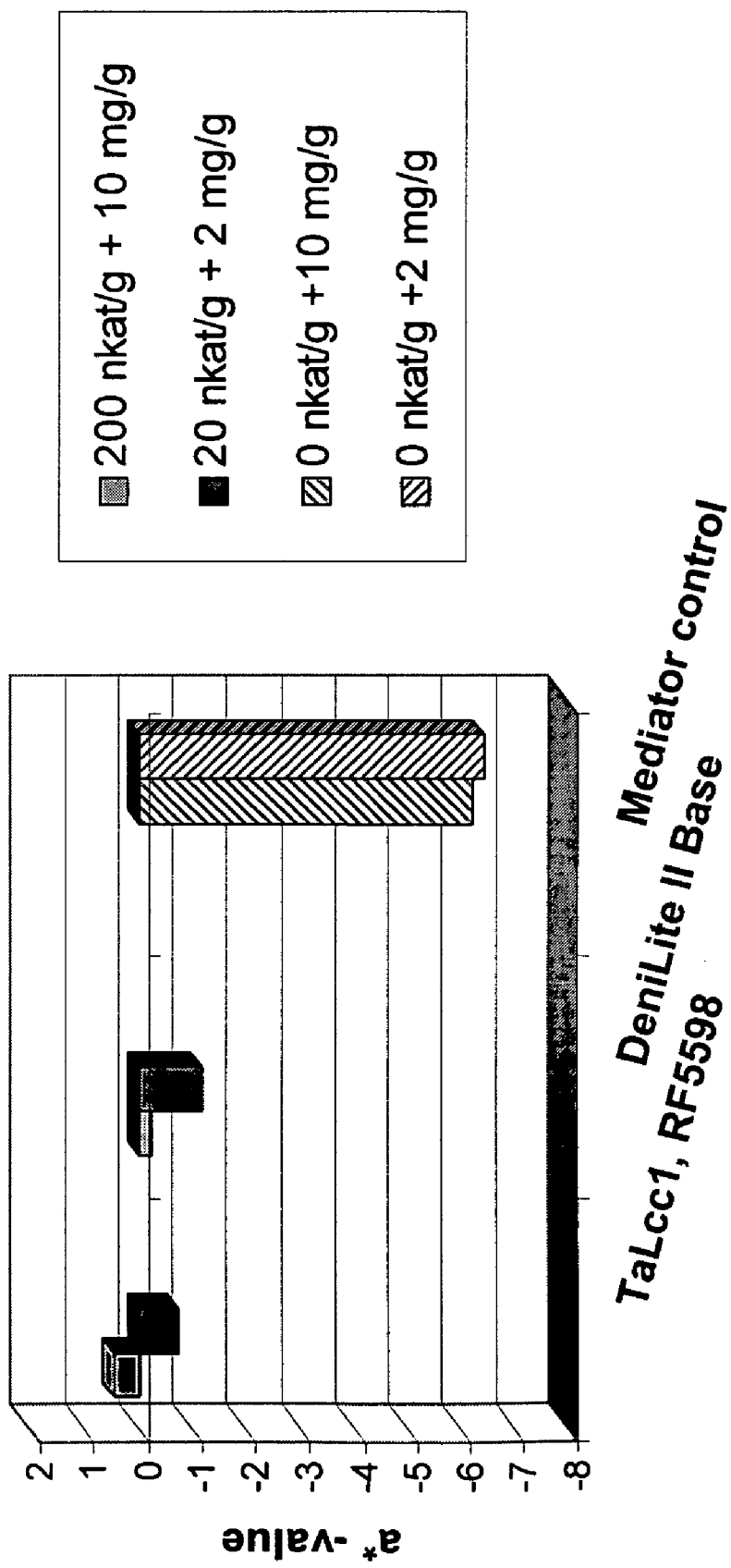

The laccase of the present invention was also more efficient in removal of tea stain with the mediator at 60° C. and slightly better even at 40° C. especially with higher dosage as can be seen in Table 22 and in FIG. 14. Mediator was needed to obtain the desired effect.

The laccase enzyme of the present invention can be used also in decolorization of dyes. Dye-house effluents, for example cannot be discharged to natural waters without removing the dyes and/or decolorizing them. The decolorization can be carried out under similar conditions as used in denim bleaching. Suitable dosage of the enzyme and treatment time depends on the amount of the dye to be decolorized and the treatment conditions.

According to a preferred embodiment of this invention decolorization of dyes is carried out at the temperature of 30 to 80° C., preferably at the temperature of 50 to 70° C., more preferably at the temperature of 60 to 70° C. The pH during the treatment can be from pH 3.5 to 8, preferably from pH 4 to 7.5, most preferably from 5 to 7. The enzyme dosages and treatment times can be tested and chosen to be most suitable for the application. As guidance the dosages of 0.2 to 2000 nkat/l of the treatment solution can be used. The treatment time is preferably 15 min to 24 hours, more preferably 30 minutes to 12 hours. If the treatment is carried out at lower temperature, for example 18 to 30° C. the treatment time may be longer.

As described in Example 12 the laccase of the present invention was tested for its ability to decolourize different dyes in the presence or absence of a mediator. The shake flasks were incubated at 50° C. for ca. 30, 90 and 150 minutes. The laccase was able to decolorize Indigocarmine, Remazol Brilliant Blue and Cibacron Brilliant Red 3B-P to great extend as can be seen in Table 23.

Since the laccase of the present invention have high oxidizing capacity of various substrates, it is well suited for many industrial applications. Such applications are for example the manufacture of fibre products and applications of forest industry, applications in the cosmetic industry and in the industry preparing personal care and other applications. In these applications, the temperature and pH are on the area where the laccase of the present invention function. The dosage and treatment time can be chosen depending on the application and material to be treated.

Mediators may be needed as additives to enhance the effect of the laccases of the present invention. In addition, it is essential that enough oxygen is brought to the reaction. If needed, oxygen can be added either by bringing air or oxygen or air enriched with oxygen to the reaction mixture.

The laccase of the present invention is suitable for use in the textile industry, for treating man-made or natural fibers or their combinations. The enzyme is suitable for treating cellulosic fibers as well as proteinaceous fibers, such as wool.

The laccase of the present invention is suitable for use in the forest industry. Lignin-containing fibres can be brought into contact with the laccase. Due to the laccase treatment, the strength properties of the fibres improve, which can be utilised, for example, in the manufacture of fibre boards, in wood composites, in paper or cardboard product and composites, which are made of mechanically ground lignin-containing fibres. Wood fibers can be treated with laccases of the present invention also to functionize them or glue the fibers.

The laccase of the present invention is also well suited to depolymerization of various compounds. By using the laccase of the present invention lignin in kraft pulp can be depolymerised thereby producing a pulp with lower lignin content. Laccase can thus be used for bleaching of pulp to decrease the use of bleaching chemicals. As a result of the better bleachability of the pulp after laccase treatment, there is a reduction of the subsequent consumption of bleaching chemicals, which when chlorine containing chemicals are used, leads to a reduced formation of environmentally undesired organochlorine compounds.

The laccase of the present invention can be used also for polymering compounds, such as lignin, to produce high molecular weight compounds.

Because of the high oxidizing capacity of the enzyme it can be used for oxidizing of dyes or dye precursors or chromophoric compounds in cosmetic industry or in industry preparing products for personal care. The oxidation of the dyes leads to decolorization of the compounds. This effect can be used for example in hair dyeing or when whitening teeth. To carry out hair dyeing dye precursors or modifiers are usually needed.

The laccase according to the invention can also be used to improve the runnability of paper machines. The laccase can be used to improve the runnability of paper machines by polymerising compounds originating from lignin and extractives and by decreasing the detrimental growth of microbes in the paper machine.

Further possible applications where laccase enzymes of the present invention can be used are methods for improving doughs in baking applications, methods for clarifying beer and wine, use in improval of the production of fuel ethanol from renewable raw materials and use in various bioremediative processes as well as use in hard-surface cleaning or in detergent formulations.

In general, in the mentioned applications the treatment temperature is preferably 30 to 80° C., more preferably 50 to 70° C., although reactions can be carried out also in lower temperatures, such as at temperatures 18 to 30° C. The pH may be 3.5 to 8, preferably 5 to 7. The treatment time may be 15 min to 24 hours, preferably 30 min to 2 hours. The dosage may be 0.1 to 2000, preferably 1 to 1000, more preferably 2 to 200 nkat/g or l of the material to be treated. A suitable amount of a suitable mediator may be added.

Compositions for the mentioned applications comprise the enzyme or enzyme preparation of the present invention in an effective amount and optionally additives suitable for the application in question. Compositions for textile industry may comprise for example a suitable amount of surface active agents, buffers stabilizers and preservatives, compositions for forest industry may comprise for example a suitable amount of buffers, stabilizers and preservatives. In all compositions should be avoided substances harmful for environment and for human (or animal) use. In particular compositions for cosmetic industry and industry for personal care products should not contain harmful effects on skin or as ingested.

The present invention provides composition for the treatment of denim comprising a laccase enzyme or an enzyme preparation according to the invention. The present invention provides also a composition for the removal of stain, a composition for the bleaching of pulp, a composition for the treating of fibre for textile industry, a composition for the treating of fibre for forest industry, a composition for the treating of wool, a composition for the treating of hair, a composition for the treating of dye house effluent, and a composition for the decolorizing of dyes comprising a laccase enzyme or an enzyme preparation according to the invention.

The following examples are intended for illustration of the present invention and should not be interpreted as limiting the present invention in any way.

EXAMPLE 1

Production and Purification of the *Thielavia* Laccase

Production of the *Thielavia* Laccase

Various strains from the culture collection of Roal Oy were screened for their ability to produce laccases with indicators Remazol Brilliant Blue R-478, tannic acid, and guaiacol as described in Kiiskinen et al. (2004). *Thielavia arenaria* ALKO4197 showed positive reactions on guaiacol and Remazol Brilliant Blue R-478.

*Thielavia* fungus was maintained on PD agar (Difco) at +4° C. The inoculation and production medium contained: 25 g/l glucose (AnalaR), 27.5 g/l Bacto yeast extract (Difco), 0.5 mg/ml Indulin AT (Sigma), 0.04 l/l mineral solution (1.0 g/l $CaCl_2.2H_2O$ (Riedel-de Haën), 1.0 g/l $FeSO_4.7H_2O$ (Riedel-de Haën), 0.1 g/l $ZnSO_4.7H_2O$ (Merck), 0.16 g/l $CuSO_4.5H_2O$ (Merck), 1.0 g/l $Na_2EDTA$ (Riedel-de Haën)). Glucose was sterilized separately and combined aseptically to the medium.

The microbe was cultivated in 50 or 200 ml volume on a rotary shaker (200 rpm) at temperature of 37° C. The medium was inoculated with 5 or 20 ml of well-grown mycelia. The laccase activity was followed up to eight days and the highest laccase activity (about 20 nkat/ml) was reached after six days of cultivation. Six parallel cultivations were made. Cells were removed from the fermentation broth by centrifugation (10 000 g for 10 min, at +4° C.) and the culture filtrate was further purified.

Purification of the *Thielavia* Laccase

Concentrated culture filtrate was first loaded on Q Sepharose FF column, which was pre equilibrated with 10 mM Tris HCL, pH 8.5. Proteins were eluted with an increasing salt gradient (0-500 mM $Na_2SO_4$ in the equilibrating buffer). Laccase active fractions were pooled and loaded on Sephacryl S100 gel filtration resin, which was equilibrated with 20 mM Tris-buffer, pH 7.0, containing 200 mM NaCl. Purification was followed by SDS-PAGE stained with Coomassie brilliant Blue. Laccase positive fractions were pooled and concentrated. Salts were removed and buffer changed to 20 mM Tris buffer, pH 7.0. In order to obtain high purity samples an additional Resource Q anion exchange step was included. The sample was loaded onto a Resource Q column, which was equilibrated with 10 mM Tris HCl pH 8.5. Proteins were eluted with a linear 1-300 mM $Na_2SO_4$ salt gradient. FIG. 1. shows the purification of the laccase.

Enzyme Activity Assay

The laccase activity from the culture supernatant was measured using ABTS as substrate. The activity assay was carried out in accordance with the method developed by Niku-Paavola et al. (1988). The sample was diluted with 0.025 M succinate buffer, pH 4.5. First 0.350 ml of ABTS solution (11 g/l) was added to 1.15 ml of the dilution, and the reaction was followed for 2 minutes at a wavelength of 436 nm. The activity is expressed as nano katals.

Determination of Protein Contents

The protein contents were determined by the DC Protein Assay kit of Bio-Rad, based on a method developed by Lowry et al. (1951). The assays were carried out according to the supplier's instructions, and the intensity of the colour formed in the reaction was measured on a wavelength of 750 nm using the Perkin Elmer Lambda 20 spectrophotometer. A standard curve was defined using bovine serum albumin in concentrations of 0.25-1.25 g/l (BSA, Bio-Rad).

EXAMPLE 2

Characterization of the Purified *Thielavia arenaria* Laccase, wt TaLcc1

Molecular Weight and pI

Molecular weight of the *Thielavia arenaria* laccase (wt TaLcc1) was determined on SDS-PAGE according to Laemmli (1970). The gels used in the SDS-PAGE analysis were ready-made 12% Tris HCl gels (BioRad). Protein bands were visualized by staining with Coomassie Brilliant Blue (R 350; Pharmacia) and compared with molecular weight markers (Prestained Protein Marker Broad Range #7708S; New England BioLabs, Beverly, Mass.). The molecular weight of the *Thielavia areanaria* laccase was approximately 80 kDa. The isoelectric point of the laccase was determined with isoelectric focusing within the pH range of 3-9 (Pharmalyte IEF, Pharmacia) on a LKB 2117 Multiphor II Electrophoresis System (LKB Pharmacia, Bromma, Sweden) according to the manufacturer's instructions. Bands containing laccase activity were visualized by staining the gel with 2 mM ABTS in 25 mM succinate buffer (pH 4.5) and proteins by Coomassie Blue staining. The purified *Thielavia* laccase showed multiple bands in isoelectric focusing at pIs 5.5, 5.9, 6.4, 6.8, and 6.9.

pH Optimum

Figure 2:
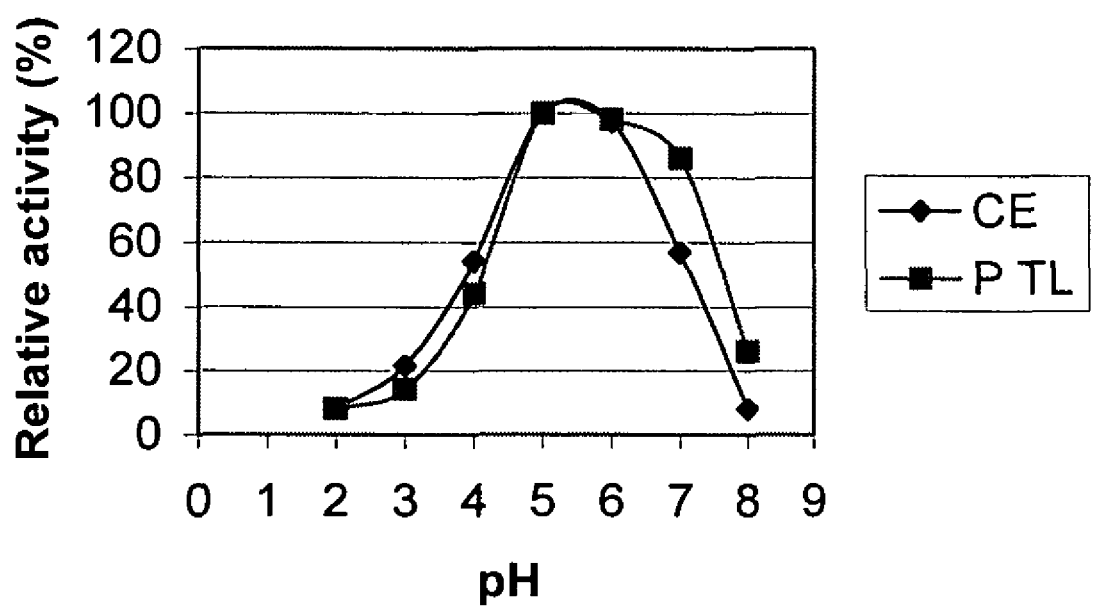
FIG. 2. pH optima of the purified *Thielavia* laccase (P TL) and the crude enzyme (CE) determined on guaiacol.

The pH-optimum of the *Thielavia arenaria* laccase was determined in the universal McIlvaine buffer within a pH range of 2.0-8.0 using guaiacol as substrate. The pH optima determined for the purified and crude *Thielavia* laccase are shown in FIG. 2. As shown in FIG. 2 the pH optimum for *Thielavia* laccase is at 5.5, the enzyme shows substantially high activity still at pH 7, above which the activity starts to drop.

Thermal Stability

Figure 3:
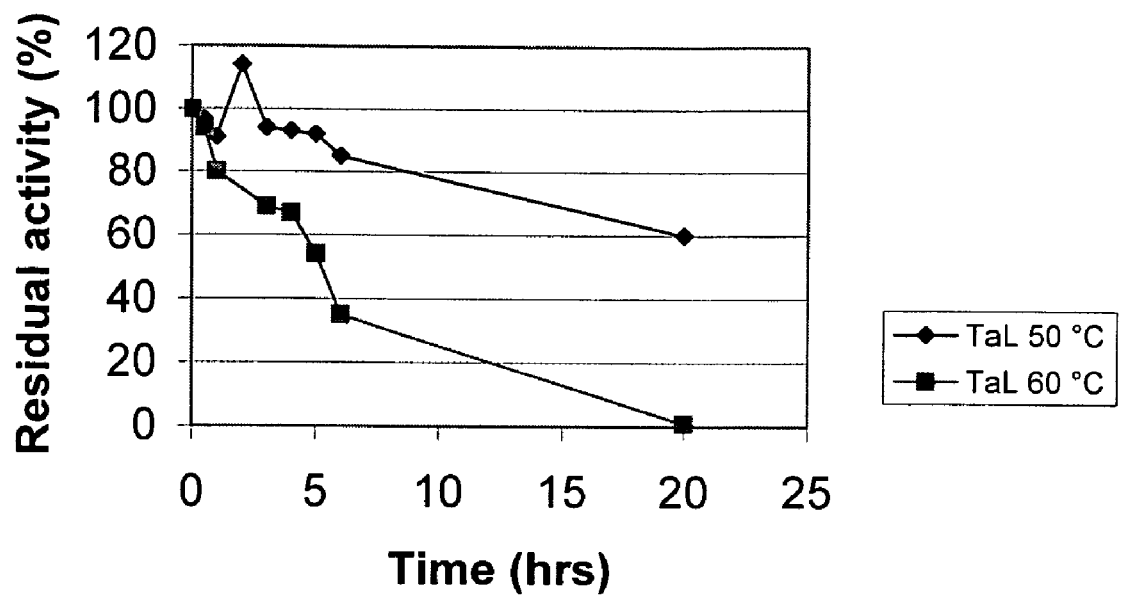
FIG. 3. Thermal stability of the wild type *Thielavia* laccase (TaL) at 50 and 60° C.

Thermal stability of the laccase was determined by incubating the enzyme solution (0.3 g $l^{-1}$) in 60 mM citrate buffer (pH 6). The residual enzyme activities were measured on ABTS. As shown from the results the half lives of the laccase were 26 and 5.5 hrs at 50, and 60° C., respectively (FIG. 3).

Specific Activity

Specific activities of the purified *Thielavia* laccase were determined towards different laccase substrates. The activities were determined towards ABTS (Niku-Paavola et al., 1988), di-metoxy-phenol (DMP) (Schlosser et al., 1997), syringaldazine (Paszczynski et al., 1985), and guaiacol (Leonowicz & Grzywnowicz, 1981). For ABTS the activity measurements were carried out in 25 mM succinate buffer pH 4.5 at 25° C. and for other substrates in 25 mM MES buffer, pH 5.5. Results are shown in Table 1.

TABLE 1

Specific activities of the purified *Thielavia* wild type laccase (wt TaLcc1).

| Substrate | Wt TaLcc1 nkat/mg |
|---|---|
| ABTS | 1020 |
| DMP | 260 |
| syringaldazin | 490 |
| Guaiacol | 63 |

Inhibition of the Laccase

The effect of various inhibitors on laccase activity was determined by measuring the oxygen consumption during the enzyme reaction with ABTS in sealed and fully filled Erlenmeyer flasks with an Orion Research 081010 oxygen electrode (Software: SensorLink™ PCM800; Orion, Espoo, Finland). The oxygen consumption rates were measured from solutions containing suitable amout of the laccase, 2 mM ABTS, and various inhibitors in different concentrations, in 25 mM succinate buffer (pH 4.5) in a 30 ml reaction volume.

TABLE 2

Inhibition of the *Thielavia* wild type laccase.

| Compound | Concentration | Inhibition(%) wt TaLcc1 |
|---|---|---|
| EDTA | 10 mM | 0 |
| NaN3 | 0.5 mM | 99 |
| KCN | 0.1 mM | 65 |
| NaCl | 0.1 mM | 35 |
| NaCl | 1 mM | 42 |

N-Terminal and Internal Amino Acid Sequencing

The N-terminus of the protein as well as the internal peptides were sequenced according to Edman degradation chemistry (Edman and Begg, 1967) using PE Biosystems Procise Sequencer. For peptide preparation, the lyophilized protein was reduced with dithiotreitol, carboxymethylated with iodoacetamide and cleaved with sequencing grade trypsin (Promega) at enzyme/substrate mass ratios 1:100 for 12 hours at 37 C in 0.1 M ammoniumbicarbonate, pH 8.3 (Stone et al., 1988). Generated peptides were separated by reversed-phase high performance liquid chromatography (RP-HPLC, Vydac C-18 column) with a linear acetonitrile gradient (0-60% acetonitrile in 0.1% trifluoroacetic acid). The internal peptide sequences are shown in Table 3. The N-terminus of the protein could not be obtained, because it was presumably blocked.

TABLE 3

Internal peptide sequences determined from *Thielavia*-laccase (ALKO4197). The N-terminus of the protein was presumably blocked.

| Peptide | Sequence | SEQ ID NO | Comments |
|---|---|---|---|
| Pept. 1 | YQGAPNTLPTNQGLPVPNH | SEQ ID NO: 1 | An equal Ile signal can also be seen in the 12th cycle |
| Pept. 2 | ENWIGPDGVLK | SEQ ID NO: 2 | |
| Pept. 3 | (S)LFLAVGQR | SEQ ID NO: 3 | (S) result unsure |

EXAMPLE 3

Cloning of the *Thielavia arenaria* ALKO4197 Gene Encoding TaLcc1

Standard molecular biology methods were used in the isolation and enzyme treatments of DNA (plasmids, DNA fragments), in *E. coli* transformations, etc. The basic methods used are described in the standard molecular biology handbooks, e.g. Sambrook et al. (1989) and Sambrook and Russell (2001).

The genomic library of *Thielavia arenaria* ALKO4197 was made to Lambda DASH®II vector (Stratagene, USA) according to the instructions from the supplier. The chromosomal DNA, isolated by the method of Raeder and Broda (1985), was partially digested with Sau3A. The digested DNA was size-fractionated in an agarose gel after which the fragments of the chosen size (9-23 kb) were isolated, dephosphorylated and ligated to the BamHI digested lambda vector arms. The ligation mixture was packaged using the Gigapack III XL packaging extracts according to the manufacturer's instructions (Stratagene, USA). The titer of the genomic library was $1.2 \times 10^6$ pfu/ml and that of the amplified library was $1.1 \times 10^{10}$ pfu/ml.

The probe used for screening of the gene bank was amplified by PCR using the *Thielavia* ALKO4197 genomic DNA as a template. First, several primers (degenerate oligos) were planned (Table 4, SEQ ID NO: 4-9) and tested in PCR reactions. The sequences of the primers based on the amino acid sequences of the peptides obtained from the purified TaLcc1 (FIG. 5). The combinations of the primers in the PCR reactions were chosen according to the location of the peptide homologues in the published laccase sequences. The PCR reaction mixtures contained 50 mM Tris-HCl, pH 9.0, 15 mM $(NH_4)_2SO_4$, 0.1% Triton X-100, 5% DMSO, 3 mM $MgCl_2$, 0.2 mM dNTPs, 5 μM each primer and 2 units of Dynazyme EXT DNA polymerase (Finnzymes, Finland) and approximately 5 μg of genomic DNA. The conditions for the PCR reactions were the following: 5 min initial denaturation at 95° C., followed by 30 cycles of 1 min at 95° C., 1 min annealing at 50° C., 2 min extension at 72° C. and a final extension at 72° C. for 10 min. The most specific result and DNA products having the expected sizes (calculated from the published fungal laccase sequences) were obtained from the PCR reactions performed with the primer combinations POX27/POX31 and POX28/POX31. The DNA fragments were isolated from these two reactions and they were cloned to pCR® Blunt-TOPO® vector (Invitrogen, USA). The DNA products were characterized by sequencing and by performing Southern blot hybridizations to the genomic *Thielavia* DNA digested with several restriction enzymes. The hybridization patterns obtained with the two fragments were identical in stringent washing conditions. The deduced amino acid sequences of both the fragments contained sequences having homology to several published laccase sequences (BLAST program, version 2.2.9 at NCBI, National Center for Biotechnology Information; Altschul et al., 1990).

The 1 kb fragment obtained from the PCR reaction by using the primers POX27 and POX31 was chosen as a probe for screening the gene bank. The sequence of this fragment included the region of the gene that had been amplified by using the primers POX28 and POX31. Also, the deduced amino acid sequence included the sequence of the internal TaLcc1 Peptide 3 (Example 2, FIG. 5). The pCR® Blunt-TOPO® vector containing the PCR fragment was named as pALK1550.

TABLE 4

The oligonucleotides (SEQ ID NOs: 4-9) synthesized as PCR primers to amplify a probe for screening the Talcc1 gene from the genomic library. Oligo, oligonucleotide; Oligo location, the amino acids of the peptide used in planning of the oligonucleotide sequence.

| Oligo | Length (nts) | Degeneracy[a] | Sequence[b] | Peptide[c] | Oligo loc. |
|---|---|---|---|---|---|
| POX26 | 26 | 8 | GAGAACTGGATCGGYCCCGAYGGYGT (s) | TaLcc1 2 | 1-9 |
| POX27 | 17 | 48 | GARAAYTGGATHGGXCC (s) | TaLcc1 2 | 1-6 |
| POX28 | 20 | 16 | CTCTTCCTCGCYGTSGGYCA (s) | TaLcc1 3 | 2-8 |
| POX29 | 20 | 16 | TGRCCSACRGCGAGGAAGAG (as) | TaLcc1 3 | 2-8 |
| POX30 | 20 | 8 | TACCAGGGYGCYCCSAACAC (s) | TaLcc1 1 | 1-7 |
| POX31 | 20 | 8 | GTGTTSGGRGCRCCCTGGTA (as)[d] | TaLcc1 1 | 1-7 |

[a]To reduce degeneracy, some codons were chosen according to fungal preference.
[b]D = A or G or T, H = A or C or T, R = A or G, S = C or G, W = A or T, X = I (inositol) or C, Y = T or C; "s" in the parenthesis = sense strand, "as" in the parenthesis = antisense strand.
[c]The peptide sequences are included in FIG. 5.
[d]The codon usage was chosen according to the preference in the xylanase genes xyn11A, xyn11B and xyn11C isolated from C. thermophilum ALKO4265 (EMBL AJ508931-508933).

The insert from the plasmid pALK1550 was labeled by using digoxigenin according to the supplier's instructions (Roche, Germany). About $1.8 \times 10^5$ plaques from the amplified genomic library were screened. The hybridization temperature for the filters was 68° C. and the filters were washed 2×5 min at RT using 2×SSC-0.1% SDS followed by 2×15 min at 68° C. using 0.1×SSC-0.1% SDS. Several positive plaques were obtained. Some of the positive plaques were giving a strong hybridization but, in addition, there was an amount of plaques hybridizing more weakly to the probe. Five of the strongly hybridizing plaques were purified (F1-F5) and the phage DNAs were isolated. A Southern blot analysis of the phage DNAs revealed that the clones F1, F2 and F3 all included an about 3 kb XhoI and about 7 kb BamHI fragments hybridizing to the probe. These fragments, and in addition a 6.1 kb SacII and 3.8 kb SpeI fragments, were isolated from the clone F1. The fragments were ligated to pBluescript II KS+ or SK+ vector (Stratagene, USA) and the plasmids obtained were named as pALK1606 (XhoI fragment), pALK1607 (BamHI fragment), pALK1341 (SacII fragment) and pALK1342 (SpeI fragment). The gene encoding the TaLcc1 was sequenced from these clones and from the shorter subclones isolated from pALK1607. The full-length Talcc1 gene was included in the plasmids pALK1607, pALK1341 and pALK1342. The E. coli strain RF5473 including the plasmid pALK1342 was deposited to the DSM collection (DSM 15484).

The Talcc1 sequence (SEQ ID NO: 11) and the deduced amino acid sequence (SEQ ID NO: 12) are shown in FIG. 6. The length of the gene is 2279 bp (including the stop codon). Six introns were found having lengths of 51, 62, 91, 83, 79 and 59 bps. The deduced protein sequence consists of 617 amino acids including a predicted signal sequence of 21 amino acids (SignalP V2.0; Nielsen et al., 1997 and Nielsen and Krogh, 1998) and a "tail" sequence of 13 amino acids (starting after the sequence DSGL). The peptides purified from the wt TaLcc1 were all found from the deduced amino acid sequence indicating that the gene cloned encodes the laccase purified from ALKO4197. The predicted molecular mass was 64456 Da for the mature polypeptide and the predicted pI was 6.31 (amino acids 22-604, signal sequence and the C-terminal tail removed). These predictions were made using the Compute pI/MW tool at ExPASy server (Gasteiger et al., 2003). The deduced amino acid sequence included nine putative N-glycosylation sites. The homologies to the published laccase sequences were searched using the BLAST program, version 2.2.9 at NCBI (National Center for Biotechnology Information) (Altschul et al., 1990). The highest homologies were found to the laccases from *Melanocarpus albomyces, Podospora anserina* and *Neurospora crassa* (EMBL accession numbers CAE00180.1, LAC2_PODAN, XP_323881.1). The TaLcc1 sequence was aligned with these three laccase sequences, with the other sequences from the NCBI database having over 50% identity to TaLcc1 in the BLAST search, and with the laccase sequences from *Myceliophthora thermophila* and *Scytalidium thermophilum*, found from the patent database (EP0765394 B1/U.S. Pat. Nos. 5,981,243 and 5,750,388, respectively). The identity values obtained by using Needleman-Wunsch global alignment (EMBLOSUM62, Gap penalty 10.0, Extend penalty 0.5; EMBOSS program package, version 2.9.0) are shown in Table 5.

TABLE 5

The identity values (%) obtained from Needleman-Wunsch global alignment of the deduced laccase amino acid sequences.

|  | TaLcc1 | Mal | Mth | Pan | Sth | Ncr LAC1 | Ncr XP | Ncr KSNCLO | Ncr LAC2 | Cpa | Ggr |
|---|---|---|---|---|---|---|---|---|---|---|---|
| TaLcc1 | 100.0 | 73.1 | 68.3 | 66.7 | 62.6 | 60.7 | 60.7 | 60.6 | 60.4 | 57.5 | 51.0 |
| MaL |  | 100.0 | 73.1 | 68.0 | 66.0 | 62.1 | 62.1 | 61.9 | 61.6 | 56.6 | 48.9 |
| Mth |  |  | 100.0 | 67.1 | 64.0 | 59.8 | 60.0 | 59.8 | 59.4 | 56.7 | 49.7 |
| Pan |  |  |  | 100.0 | 59.8 | 61.4 | 61.4 | 61.4 | 61.2 | 55.3 | 49.3 |
| Sth |  |  |  |  | 100.0 | 57.6 | 57.8 | 57.6 | 57.5 | 54.7 | 49.8 |
| Ncr LAC1 |  |  |  |  |  | 100.0 | 99.5 | 99.7 | 97.7 | 54.2 | 46.5 |
| Ncr XP |  |  |  |  |  |  | 100.0 | 99.8 | 98.2 | 54.2 | 46.6 |
| Ncr KSNCLO |  |  |  |  |  |  |  | 100.0 | 98.1 | 54.1 | 46.4 |

TABLE 5-continued

The identity values (%) obtained from Needleman-Wunsch global alignment of
the deduced laccase amino acid sequences.

|  | TaLcc1 | Mal | Mth | Pan | Sth | Ncr LAC1 | Ncr XP | Ncr KSNCLO | Ncr LAC2 | Cpa | Ggr |
|---|---|---|---|---|---|---|---|---|---|---|---|
| Ncr LAC2 |  |  |  |  |  |  |  |  | 100.0 | 54.7 | 46.6 |
| Cpa |  |  |  |  |  |  |  |  |  | 100.0 | 46.3 |
| Ggr |  |  |  |  |  |  |  |  |  |  | 100.0 |

The full-length amino acid sequences including the signal peptides were aligned. Matrix: EMBLOSUM62, Gap penalty 10.0, Extend penalty 0.5.
MaL *Melanocarpus albomyces* CAE001810,
Mth *Myceliophthora thermophila* laccase from EP 0765394 B1,
Pan *Podospora anserina* LAC2_PODAN,
Sth *Scytalidium thermophilum* laccase from U.S. Pat. No. 5,750,388,
Ncr LAC1 *Neurospora crassa* LAC1_NEUCR,
Ncr XP *N. crassa* XP_323881,
Ncr KSNCLO *N. crassa* KSNCLO,
Ncr LAC2 *N. crassa* LAC2_NEUCR,
Cpa *Cryphonectria parasitica* LAC1_CRYPA,
Ggr *Gaeumannomyces graminis* var *tritici* Lac3 CAD100749.

EXAMPLE 4

Production of the Recombinant TaLcc1 in *Trichoderma reesei*

Figure 7:
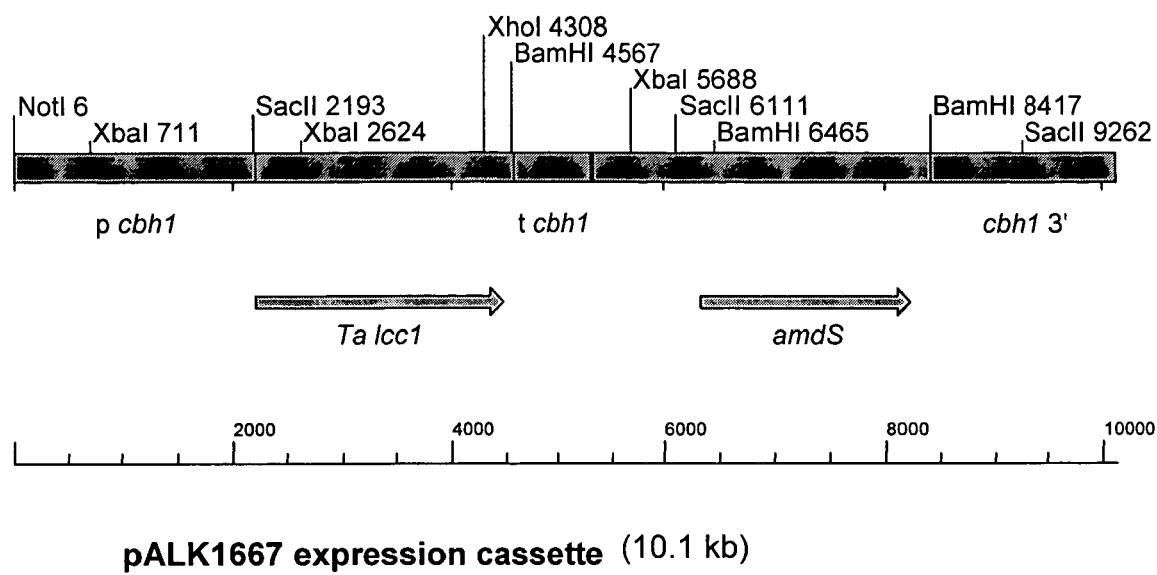
FIG. 7. The expression cassette pALK1667 used in the transformation of *Trichoderma reesei* protoplasts for producing the recombinant TaLcc1. The laccase gene was under the control of the cbh1 (cel7A) promoter (p cbh1) and termination of transcription was ensured by using the cbh1 terminator sequence (t cbh1). The amdS gene was included as a transformation marker and the cbh1 3'-flanking region, together with the cbh1 promoter, was used to enable targeting of the expression cassette into the cbh1 locus by homologous recombination.

The expression plasmid pALK1667 was constructed for production of recombinant TaLcc1 in *Trichoderma reesei*. The Talcc1 gene with its own signal sequence was exactly fused to the *T. reesei* cbh1 (cel7A) promoter by PCR. The cbh1 promoter, cbh1 terminator, amdS marker and the cbh1 3' flanking region included were as described in Paloheimo et al. (2003). The Talcc1 gene fragment was excised from its 3'-end by NcoI. This cleavage left 80 bp of the Talcc1 terminator in the construct, prior to the cbh1 terminator sequence. The 10.1 kb linear expression cassette (FIG. 7) was isolated from the vector backbone after EcoRI digestion and was transformed to *T. reesei* A47 protoplasts. The transformations were performed as in Penttilä et al. (1987) with the modifications described in Karhunen et al. (1993). The transformants were purified on selection plates through single conidia prior to sporulating them on PD.

The laccase production of the transformants was analysed from the culture supernatants of the shake flask cultivations (50 ml). The transformants were grown for 7 days in a complex lactose-based cellulase-inducing medium (Joutsjoki et al. 1993) buffered with 5% KH$_2$PO$_4$ and supplemented with 0.1 mM CuSO$_4$ at pH 6.0. The laccase activity was assayed using ABTS as a substrate as described in Example 1. The possible targeting of the expression cassette to the cbh1 locus was screened as a CBHI-negative phenotype by dot blot (Minifold I-SRC 96; Schleicher & Schuell, Dassel, Germany) or by Western blot. The detection of the CBHI protein was performed using the monoclonal antibodies CI-258 or CI-261 (Aho et al., 1991) and the ProtoBlot Western blot AP system (Promega). The genotypes of the chosen transformants were confirmed by using Southern blots in which several genomic digests were included and the respective expression cassette was used as a probe.

The chosen CBHI-negative transformants RF5597 and RF5598 were fermented to obtain material for purification of the recombinant TaLcc1 (Example 5) and for the application tests (Examples 7-12).

EXAMPLE 5

Purification of TaLcc1 of *Thielavia* (ALKO4197) Expressed in *T. reesei*

Figure 4:
FIG. 4. Purification of the recombinant TaLcc1, SDS-PAGE (12.5%), Lanes: 1 MW marker (175, 83, 62, 47.5, 32.5, 25, 16.5 kDa) 2. culture supernatant, 3. fractions after DEAE Sepharose, 4. fractions after Resource Q 5-9. fractions after gel filtration.

TaLcc1 is the multiple pI isoform laccase i.e. the enzyme shows 6-7 distinct bands in isoelectric focusing and subsequent active staining within the pH range of 5.5-6.9. The buffer of culture supernatant was first changed to 5 mM Tris-HCl buffer, pH 8.5 with Sephadex G25 resin. The sample was loaded onto a pre equilibrated DEAE Sephadex FF column. Proteins were eluted with a linear Na$_2$SO$_4$ salt gradient (0-350 mM). Laccase positive fractions from DEAE Sepharose were pooled and the buffer changed to 5 mM Tris-HCl buffer, pH 8.5 with Pharmacia PD 10 columns. The sample was loaded on a pre equilibrated Resource Q column. Proteins were eluted with an increasing linear Na$_2$SO$_4$ (0-200 mM). Laccase positive fractions eluted within 5-40 mM Na2SO4 salt concentration. The final purification step was carried out with gel filtration. The laccase positive fractions from Resource Q were pooled and concentrated with ContraSep MWCO 10 kDa. The sample was loaded on a pre equilibrated Sephacryl S-100 gel filtration column. The buffer used in the gel filtration was 100 mM Tris-HCl, pH 7.3, containing 150 mM NaCl. The SDS-PAGE showing the purification of the recombinant TaLcc1 laccase is shown in FIG. 4.

EXAMPLE 6

Characterization of the Recombinant TaLcc1 Laccase

The purified recombinant *Thielavia arenaria* TaLcc1 was characterized in terms of pH optimum, thermal stability, and pI as described in Example 2. The molecular weight was determined by MALDI-TOF mass spectrometry on a Ultraflex™ time-of-flight instrument (BrukerDaltonics, Germany) as previously described (Palonen et al., 2003). The redox potential of TaLcc1 was also determined with a combined Pt-AgCl/KCl microelectrode at pH 5.0 according to Sigoillot et al (2004)

The characterization results are collected to Table 6.

TABLE 6

Summary of the characteristics of the recombinant *Thielavia arenaria* TaLcc1 (rTaLcc1) and the wild type TaLcc1 (wt TaLcc) laccases.

| Laccase | pH optimum on guaiacol | T½ (60° C.) (hrs) | pI | Number of pI isoforms | MW (MALDI-TOF) | $E^0$ mV |
|---|---|---|---|---|---|---|
| rTaLcc1 | 6.0 | 5 | 5.5-6.9 | 6-7 | 71 890 | 560 |
| wt TaLcc | 6.0 | 5.5 | 5.5-6.9 | 6-7 | Nd | nd | nd = not determined.

The inhibition effect of different compounds on the activity of the recombinant TaLcc1 laccase was determined as described in Example 2. Results are shown in Table 7.

TABLE 7

Inhibition of the recombinant *Thielavia arenaria* TaLcc1 laccase (rTaLcc1) activity by various compounds.

| | | Inhibition (%) of laccase | |
|---|---|---|---|
| Compound | Concentr. (mM) | wtTaLcc | rTaLcc1 |
| EDTA | 10 | 0 | 5 |
| NaN$_3$ | 0.5 | 99 | 95 |
| KCN | 0.1 | 65 | 60 |
| KCN | 1 | Nd | 90 |
| NaCl | 0.1 | 35 | 0 |
| NaCl | 1 | 42 | 0 |

Inhibition was tested by oxygen consumption measurements in standard condition using ABTS as substrate (Example 2). As a comparison the inhibition results of the wild type *Thielavia arenaria* laccase (wtTaLcc) are also shown.
nd = not determined.

Specific activities of the purified TaLcc1 were determined towards ABTS, dimetoxy phenol (DMP), syringaldazine, and guaiacol as described in Example 2. The ABTS activity measurements were carried out in 25 mM succinate buffer pH 4.5 at 25° C., and the other activities in 25 mM MES buffer, pH 5.5. The results are shown in Table 8.

TABLE 8

Specific activities of recombinant TaLcc1 (rTaLcc1) compared to the specific activities of the wild type enzyme (wtTaLcc).

| Substrate | Spec. act. wtTaLcc (nkat/mg) | Spec. act. rTaLcc1 (nkat/mg) |
|---|---|---|
| ABTS | 1020 | 910 |
| DMP | 260 | 285 |
| Syringaldazine | 490 | 340 |
| Guaiacol | 63 | 61 |

The biochemical data presented here clearly indicates that the recombinant TaLcc1 is the same protein as the wild type *Thielavia* laccase purified from the culture supernatant.

Kinetic Parameters of *Thielavia* and *Melanocarpus* Laccases

The kinetic parameters, Michaelis-Menthen constant $K_m$, turn-over number $k_{cat}$ and the specificity constant ($k_{cat}/K_m$) were determined on ABTS and 2,6-dimethoxy phenol (DMP), and syringaldatzin. The measurements on ABTS were done in 25 mM succinate buffer, pH 4.5. On syringaldazin and DMP 40 mM MES buffer, pH 6 and 25 mM succinate buffer. All activity assays were carried out at 25° C. Kinetic parameters were estimated by a nonlinear regression curve fit. The results are shown in Table 9. The values were compared to those of *Melanocarpus albomyces* MaL, laccase.

TABLE 9

Kinetic parameters of recombinant TaLcc1 determined on ABTS, syringaldazin, and DMP.

| | TaLcc1 | MaL |
|---|---|---|
| ABTS | | |
| $K_m$ (µM) | 75 | 270 |
| $k_{cat}$ (min$^{-1}$) | 4130 | 4690 |
| $k_{cat}/K_m$ (M$^{-1}$min$^{-1}$) | $5.51 * 10^7$ | $1.8 * 10^7$ |
| DMP | | |
| $K_m$ (µM) | 17 | 5 |
| $k_{cat}$ (min$^{-1}$) | 4030 | 4160 |
| $k_{cat}/K_m$ (M$^{-1}$min$^{-1}$) | $2.37 * 10^8$ | $8.1 * 10^8$ |
| Syringaldazin | | |
| $K_m$ (µM) | 4.3 | 1.3 |
| $k_{cat}$ (min$^{-1}$) | 1940 | 4710 |
| $k_{cat}/K_m$ (M$^{-1}$min$^{-1}$) | $4.51 * 10^8$ | $3.6 * 10^9$ |

As a comparison the values of a well-known laccase from *Melanocarpus albomyces* MaL are also shown.

EXAMPLE 7

Performance of the TaLcc1 Laccase Preparation in Denim Bleaching at Different pH-Values Recombinant TaLcc1 laccase preparations produced using *Thrichoderma* as a host were used in all the application tests, in Examples 7-12. The TaLcc1 preparation (derived from the strain RF5598) was tested for its ability to bleach denim and compared to a commercial laccase preparation DeniLite II Base from Novozymes.

Lee Cooper jeans (Hamilton, 111-1060-55522-65, MASI Company Oy, Finland, former name M.A.S.I. jeans Oy) that were made of ring spun yarn in warp and open-end yarn in weft and were previously desized and treated with neutral ECOSTONE® cellulase were used as a test material. Laccase treatments were performed in LP-2 Launder Ometer as follows. About 10 g of denim swatches (15×14 cm) were loaded into 1.2 liter containers containing 200 ml Mc Ilvaine's citrate phosphate buffer pH 5, 6 or 7 and the containers were temperated. Enzyme with or without the mediator (methyl syringate, DeniLite II Assist, Novozymes) was added. Enzyme was dosed 200 nkat/g and the mediator 10 mg/g on the weight of fabric. The enzyme activity was measured with ABTS substrate as in Example 1 but using citrate phosphate buffer in all examples 7-12. The Launder Ometer was run at 50° C. for 30 min and after that the temperature in Launder was raised to 80° C. for 10 min. The swatches were rinsed carefully with warm water, dried half-dry in a tumbler and after that air dried.

The bleaching effect was evaluated by measuring the colour as reflectance values with the Minolta Spectrophotometer CM 1000 (Minolta Co.) using L*a*b* color space coordinates (illuminant D65/2°). The colour from both sides of the swatches was measured before and after the laccase treatment. Each measurement was the average of several, at least ten, measurements.

Table 10 and FIG. 8 clearly show that TaLcc1 laccase was superior in decolorization of indigo dye of denim compared to the commercial DeniLite II Base at all pH values from 5 to 7, pH 6 being the optimum. Only the TaLcc1 preparation was capable in achieving a strongly bleached look with the highest lightness value. The increase of lightness and the decrease of blueness on the reverse side of denim was also the highest with denim treated with TaLcc1 laccase preparation and the mediator. Without the mediator the laccases did not have a notable effect on denim. (Table 11). Bleaching tests performed with TaLcc1 laccase later showed that the enzyme works well at broad pH range (4-8).

TABLE 10

Colour measurements of the face side of denim treated with laccase preparations and the mediator in Launder at pH 5-7.

| Prep. | Enzyme nkat/g | Mediator mg/g | Conditions | Before laccase Treatment L* | b* | After laccase Treatment L* | B* | Increase of L* |
|---|---|---|---|---|---|---|---|---|
| TaLcc1 | 200 | 10 | 30 min, 50° C., pH 5 | 28.52 | −18.46 | 42.04 | −14.78 | 13.52 |
| DeniLite | 200 | 10 | 30 min, 50° C., pH 5 | 28.41 | −18.70 | 35.70 | −17.59 | 7.29 |
| TaLcc1 | 200 | 10 | 30 min, 50° C., pH 6 | 27.78 | −18.49 | 48.97 | −12.36 | 21.19 |
| DeniLite | 200 | 10 | 30 min, 50° C., pH 6 | 26.98 | −18.67 | 34.16 | −17.82 | 7.18 |
| TaLcc1 | 200 | 10 | 30 min, 50° C., pH 7 | 27.79 | −19.00 | 44.71 | −14.43 | 16.92 |
| DeniLite | 200 | 10 | 30 min, 50° C., pH 7 | 28.67 | −18.99 | 34.51 | −17.75 | 5.84 |

L* indicates lightness,
−b* is the blue direction,
+b* is the yellow direction.

TABLE 11

Colour measurements of the face side of denim treated with laccase preparations without the mediator or mediator only in Launder at pH 5-7.

| Prep. | Enzyme nkat/g | Mediator mg/g | Conditions | Before laccase Treatment L* | b* | After laccase Treatment L* | B* | Increase of L* |
|---|---|---|---|---|---|---|---|---|
| TaLcc1 | 200 | 0 | 30 min, 50° C., pH 5 | 28.08 | −18.41 | 28.22 | −18.35 | 0.14 |
| DeniLite | 200 | 0 | 30 min, 50° C., pH 5 | 29.18 | −18.55 | 29.30 | −18.34 | 0.12 |
| Mediator | 0 | 10 | 30 min, 50° C., pH 5 | 29.85 | −18.58 | 29.90 | −18.15 | 0.05 |
| TaLcc1 | 200 | 0 | 30 min, 50° C., pH 6 | 28.77 | −18.77 | 29.58 | −18.38 | 0.82 |
| DeniLite | 200 | 0 | 30 min, 50° C., pH 6 | 28.55 | −18.48 | 28.77 | −18.52 | 0.22 |
| Mediator | 0 | 10 | 30 min, 50° C., pH 6 | 28.68 | −18.40 | 28.90 | −18.37 | 0.22 |
| TaLcc1 | 200 | 0 | 30 min, 50° C., pH 7 | 27.43 | −18.93 | 27.80 | −18.50 | 0.37 |
| DeniLite | 200 | 0 | 30 min, 50° C., pH 7 | 27.82 | −18.93 | 29.78 | −18.31 | 1.96 |
| Mediator | 0 | 10 | 30 min, 50° C., pH 7 | 29.00 | −18.94 | 30.06 | −18.46 | 1.06 |

L* indicates lightness,
−b* is the blue direction,
+b* is the yellow direction.

EXAMPLE 8

Performance of TaLcc1 Laccase Preparation in Denim Bleaching at Different Temperatures The ability of the TaLcc1 enzyme preparation derived from the strain RF5598 (Example 7) to bleach denim at different temperatures was tested and compared to the commercial laccase preparation DeniLite II Base from Novozymes.

The test system and denim were as in Example 7, except that the conditions during the laccase and mediator treatment in Launder were 30 min, pH 6 and temperature 30-80° C. Also, the enzyme was inactivated by an alkaline treatment instead of raising the temperature in Launder as follows. After removing swatches from the containers they were soaked in warm water containing NaOH (pH 11.5) for 10 min and rinsed carefully with warm water. The swatches were dried half-dry in a tumbler and after that air dried. The bleaching effect was evaluated by measuring the colour as reflectance values as in Example 7.

Table 12 and FIG. 9 show that TaLcc1 laccase was superior in bleaching of denim (higher increase of lightness) compared to DeniLite II Base at 40-80° C. The temperature 60-70° C. was the most optimal for TaLcc1 and the look of the denim fabric was strongly faded. The DeniLite II Base was capable only for moderate decolorization of indigo.

TABLE 12

Colour measurements of the face side of denim treated with laccases and the mediator in Launder at different temperatures.

| Prep. | Enzyme nkat/g | Mediator mg/g | Conditions | Before laccase Treatment L* | b* | After laccase Treatment L* | B* | Increase of L* |
|---|---|---|---|---|---|---|---|---|
| TaLcc1 | 200 | 10 | 30 min, 30° C., pH 6 | 29.58 | −18.82 | 33.68 | −19.17 | 4.10 |
| DeniLite | 200 | 10 | 30 min, 30° C., pH 6 | 29.56 | −18.60 | 32.73 | −18.77 | 3.17 |

TABLE 12-continued

Colour measurements of the face side of denim treated with laccases and the mediator in Launder at different temperatures.

| Prep. | Enzyme nkat/g | Mediator mg/g | Conditions | Before laccase Treatment L* | b* | After laccase Treatment L* | B* | Increase of L* |
|---|---|---|---|---|---|---|---|---|
| TaLcc1 | 200 | 10 | 30 min, 40° C., pH 6 | 28.81 | −19.03 | 37.49 | −18.64 | 8.68 |
| DeniLite | 200 | 10 | 30 min, 40° C., pH 6 | 28.87 | −18.90 | 32.94 | −19.14 | 4.07 |
| TaLcc1 | 200 | 10 | 30 min, 50° C., pH 6 | 28.40 | −18.88 | 42.99 | −17.06 | 14.59 |
| DeniLite | 200 | 10 | 30 min, 50° C., pH 6 | 28.41 | −19.10 | 34.67 | −19.07 | 6.26 |
| TaLcc1 | 200 | 10 | 30 min, 60° C., pH 6 | 29.14 | −19.03 | 47.56 | −14.55 | 18.42 |
| DeniLite | 200 | 10 | 30 min, 60° C., pH 6 | 29.06 | −18.99 | 35.92 | −18.33 | 6.86 |
| TaLcc1 | 200 | 10 | 30 min, 70° C., pH 6 | 29.09 | −19.03 | 46.94 | −13.82 | 17.85 |
| DeniLite | 200 | 10 | 30 min, 70° C., pH 6 | 29.05 | −19.15 | 36.72 | −17.35 | 7.67 |
| TaLcc1 | 200 | 10 | 30 min 80° C., pH 6 | 29.39 | −19.01 | 39.24 | −15.74 | 9.85 |
| TaLcc1 | 200 | 0 | 30 min, 80° C., pH 6 | 29.63 | −19.16 | 30.27 | −18.62 | 0.64 |
| DeniLite | 200 | 10 | 30 min, 80° C., pH 6 | 29.28 | −18.97 | 35.33 | −17.02 | 6.05 |
| DeniLite | 200 | 0 | 30 min, 80° C., pH 6 | 29.81 | −18.74 | 31.69 | −18.19 | 1.88 |

L* indicates lightness,
−b* is the blue direction,
+b* is the yellow direction.

EXAMPLE 9

Effect of Enzyme Dosage in Bleaching of Denim with Laccase-Mediator System

Lee Cooper Jeans previously washed with ECOSTONE® cellulases (Example 7) were treated with a TaLcc1 laccase product from *Trichoderma* strain RF5598 and DeniLite Base from Novozymes using different laccase dosages. The laccase treatments were performed with Electrolux's Wascator FOM 71 CLS washer extractor under optimal conditions for each enzyme, shown in Table 13. Methyl syringate (Example 7) was used as a mediator. Laccase was inactivated after draining by raising the pH above 11 by NaOH (10 min, 60° C.) and rinsing 3 times. The fabrics were dried in a tumbler.

TABLE 13

The process parameters used in the bleaching test with TaLcc1 and DeniLite II Base laccase preparations with different dosages.

| Process parameter | TaLcc1 laccase | DeniLite II Base laccase |
|---|---|---|
| Denim load | 1.5 kg | 1.5 kg |
| Water | 15 l | 15 l |
| Buffer/pH control | 37.5 g Na$_2$HPO$_4$*2H$_2$0 14.7 g citric acid | Acetic acid |
| pH | 6 | 5-5.5 |
| Time | 30 min or 60 min | 30 min |
| Temperature | 60° C. | 60° C. |

TABLE 13-continued

The process parameters used in the bleaching test with TaLcc1 and DeniLite II Base laccase preparations with different dosages.

| Process parameter | TaLcc1 laccase | DeniLite II Base laccase |
|---|---|---|
| Enzyme dosage | 20 or 100 nkat/g fabric | 20 or 100 nkat/g fabric |
| Mediator Dosage | 1 or 5 mg/g fabric | 1 or 5 mg/g fabric |

Figure 10:
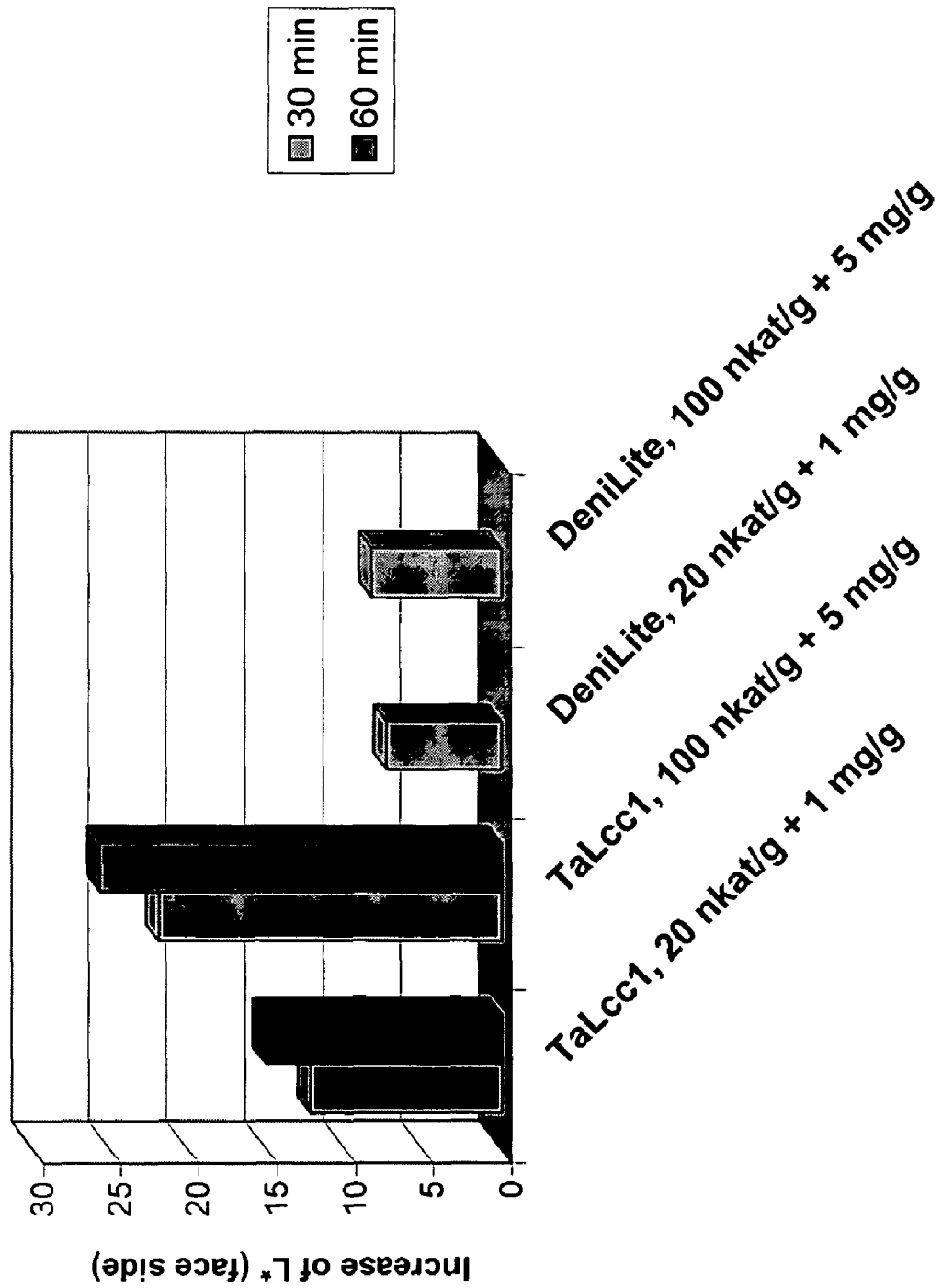
FIG. 10. The effect of enzyme dosage on bleaching of denim using TaLcc1 laccase preparation. The bleaching was performed as described in Example 9. DeniLite II Base was used for comparison.
Figure 11A:
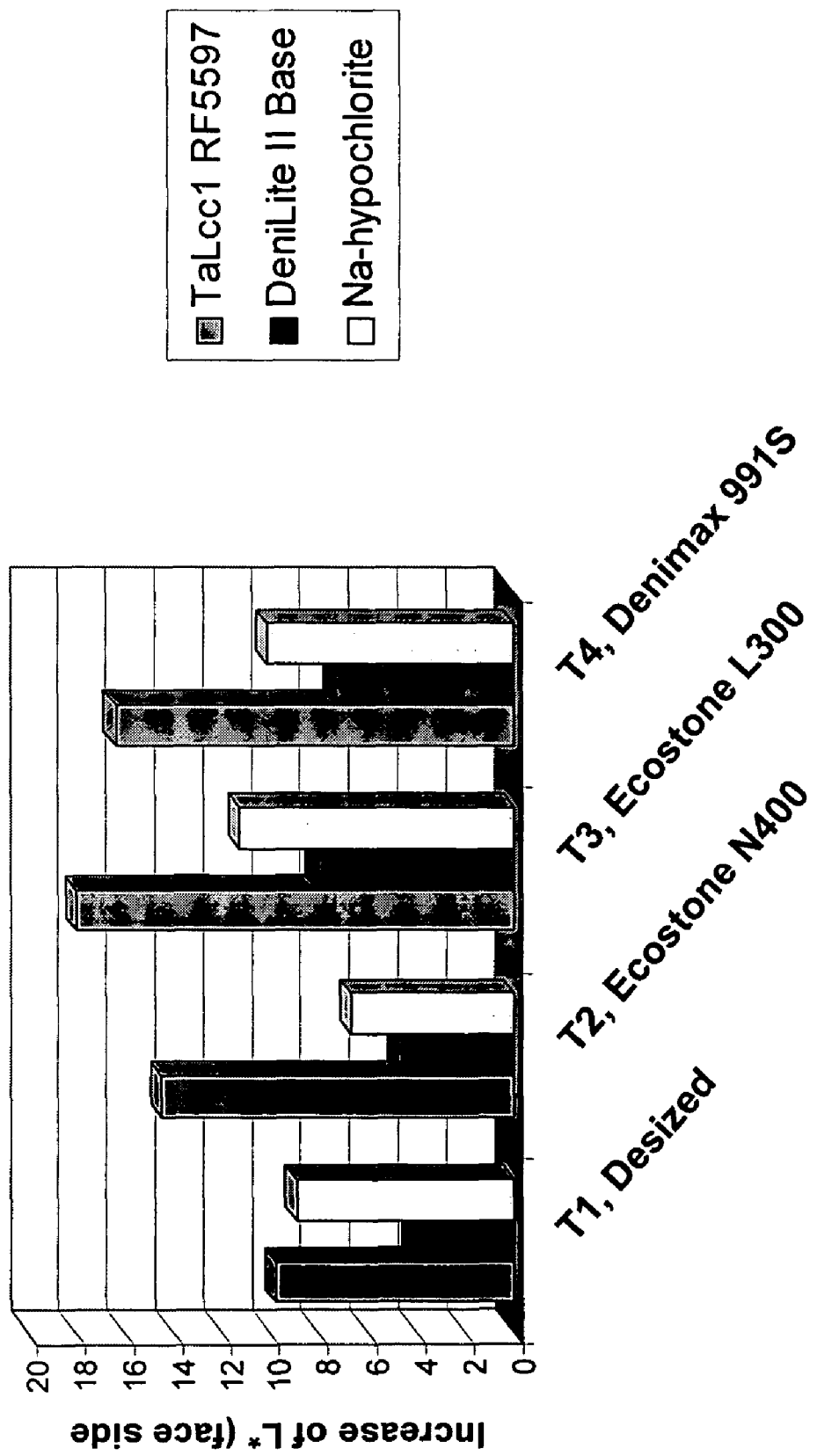
FIG. 11 A-D. Bleaching of different types of denim with TaLcc1 laccase compared to bleaching with hypochlorite or DeniLite II Base. The bleaching was performed as described in Example 10. A. The results on bleaching Tincan Jeans, B. Lee Cooper Jeans, C. Warrick Jeans, D. English Jeans.
Figure 11B:
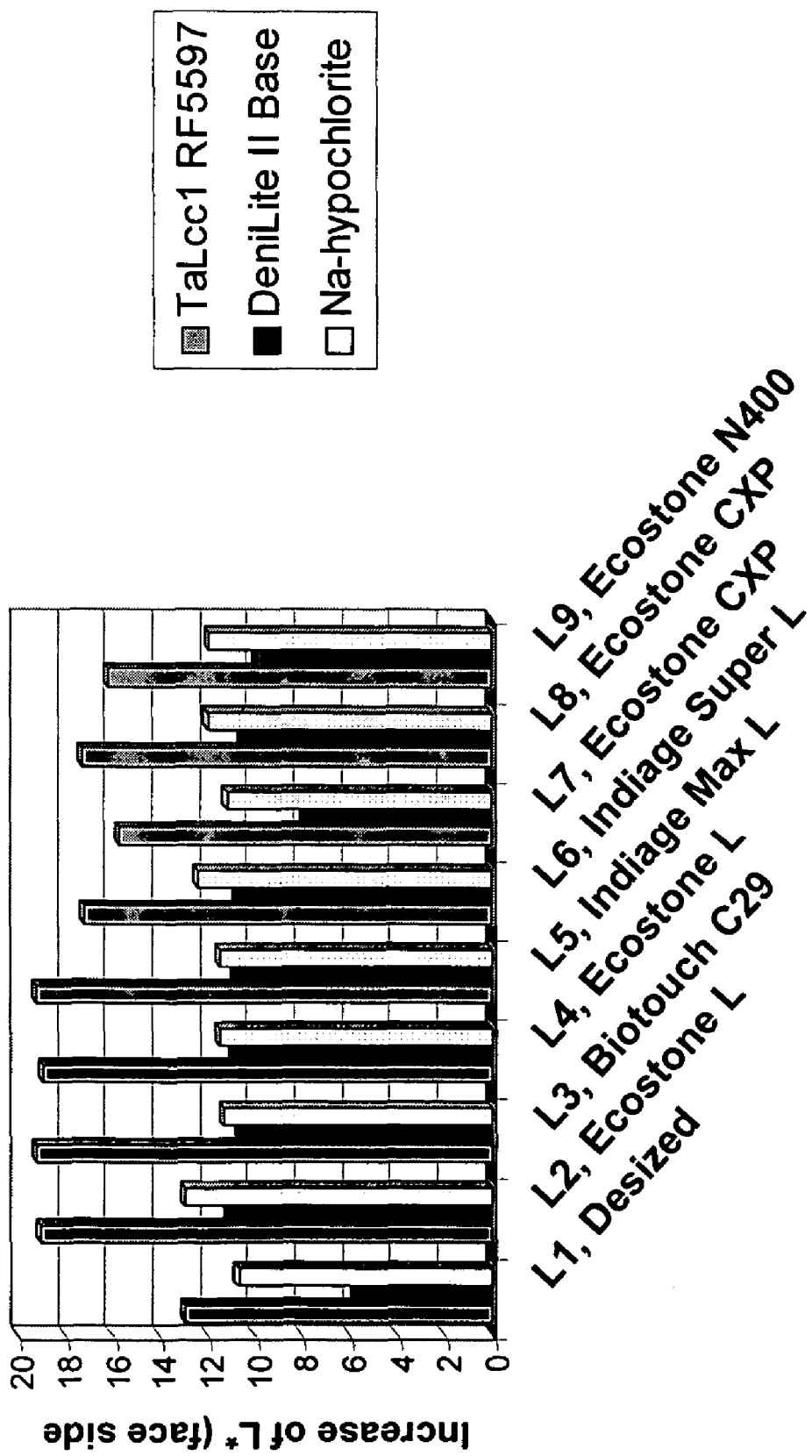
Figure 11C:
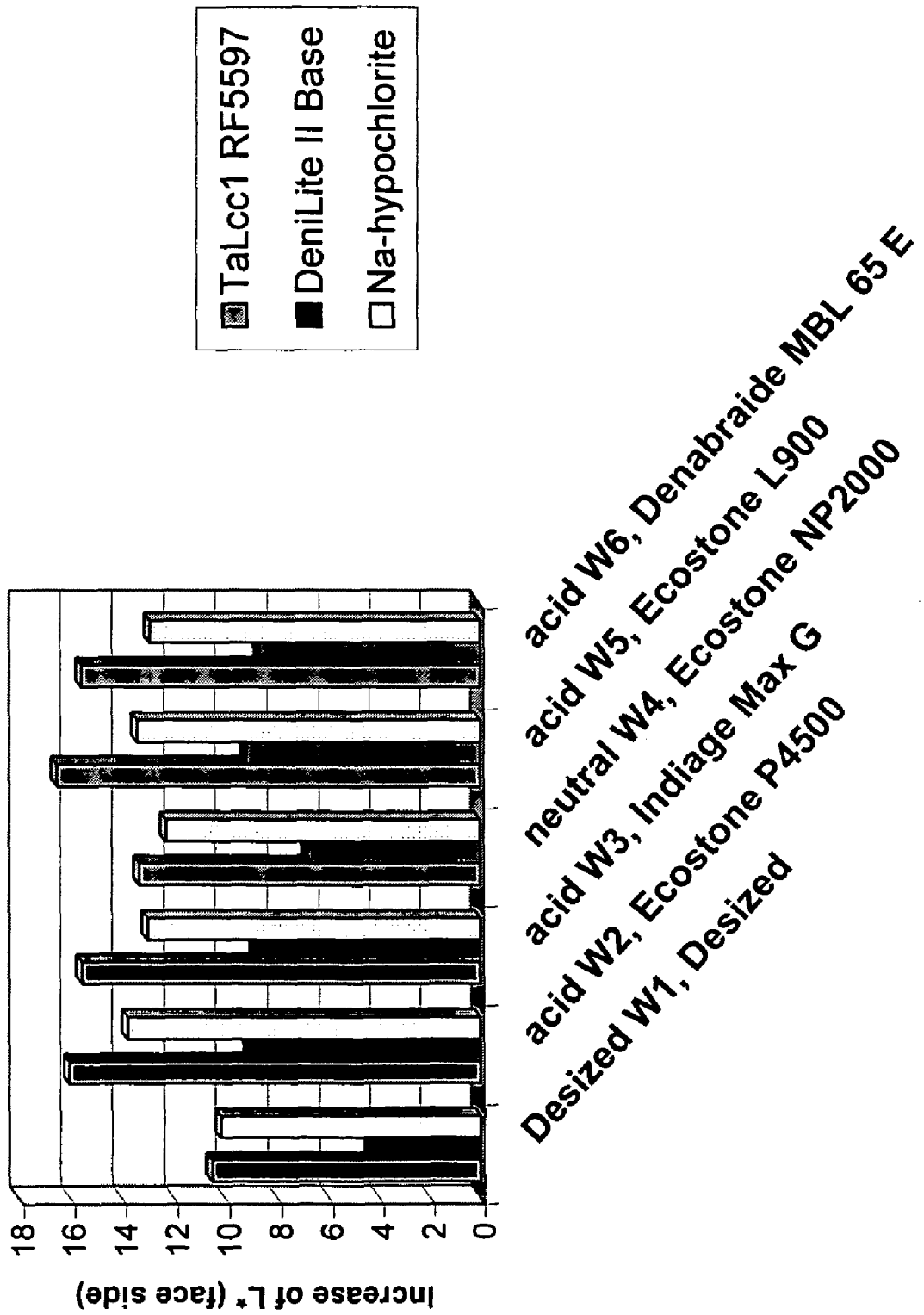
Figure 11D:
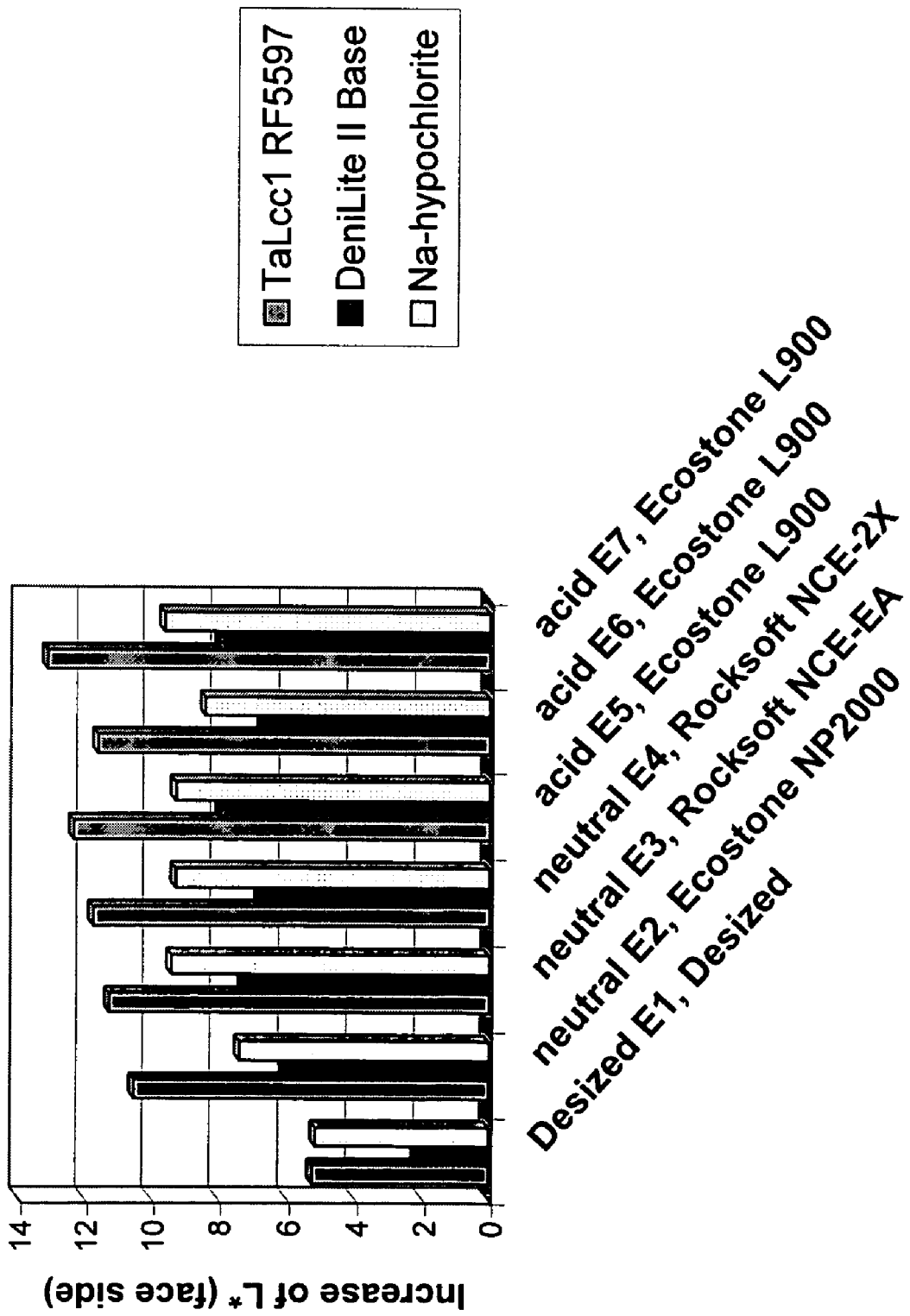

The bleaching effect was evaluated by measuring the colour after laccase treatment as reflectance values (as in Example 7) and comparing the values to previously measured values after cellulase treatment. Results in Table 14 and FIG. 10 show that increase of the dosage greatly improved the bleaching performance of TaLcc1 laccase.

With DeniLite II Base the effect of the dosage was low. Increasing the time from 30 min to 60 min further improved the performance of TaLcc1 laccase. With DeniLite increasing the treatment time longer than 30 minutes provides no additional bleaching performance as discussed in Mueller and Shi (2000). With TaLcc1 laccase it was possible to achieve very strong bleaching effect that is normally obtained only with the use of high amounts of sodium hypochlorite. Also the abraded look was maintained. Up to this date such high increase of lightness of denim obtained with the use of a laccase-mediator system has not been reported.

TABLE 14

Colour measurements of the face side of denim treated with laccase preparations and the mediator in Launder using different dosages.

| Prep. | Enzyme nkat/g | Mediator mg/g | Conditions | Before laccase Treatment L* | Before laccase Treatment b* | After laccase treatment L* | After laccase treatment B* | Increase of L* |
|---|---|---|---|---|---|---|---|---|
| TaLcc1 | 20 | 1 | 30 min, 60° C., pH 6 | 28.37 | −18.56 | 40.61 | −16.16 | 12.24 |
| TaLcc1 | 100 | 5 | 30 min, 60° C., pH 6 | 27.96 | −18.88 | 49.84 | −13.75 | 21.88 |
| TaLcc1 | 20 | 1 | 60 min, 60° C., pH 6 | 27.63 | −18.54 | 42.72 | −15.61 | 15.09 |
| TaLcc1 | 100 | 5 | 60 min, 60° C., pH 6 | 27.78 | −18.91 | 53.46 | −11.64 | 25.68 |
| DeniLite | 20 | 1 | 30 min, 60° C., pH 5.3 | 28.78 | −18.46 | 36.13 | −17.12 | 7.35 |
| DeniLite | 100 | 5 | 30 min, 60° C., pH 5-5.5 | 28.88 | −18.74 | 37.19 | −17.37 | 8.32 |

L* indicates lightness,
−b* is the blue direction,
+b* is the yellow direction.

EXAMPLE 10

Bleaching of Denim with Laccase-Mediator System Compared to Bleaching with Sodium Hypochlorite Different types of demin were treated with a TaLcc1 laccase product from *Trichoderma* strain RF5597 and DeniLite II Base from Novozymes and the results obtained were compared to hypochlorite bleaching. All together 27 pieces of different kinds of denim (whole jeans), which had been previously washed with cellulase after desizing to different abrasion levels or had been only desized with ECOSTONE®A200 (60° C., 10 min), were collected for the test (Table 15). The jeans were made of Indigo dyed denim, except the English jeans contained Indigo dyed denim with sulphur bottom. Jeans were cut in such a way that pieces from the same pair of jeans could be used for all tests.

The jeans were made of Indigo dyed denim (right hand twill), except the English jeans contained Indigo dyed denim with sulphur bottom. The weights of the original (i.e. not desized) denim fabrics were typically higher than 475 g/m² (14 oz/yd²). The weights of three 10 cm×10 cm pieces were measured after 24 hours incubation at room temperature (ca. 22° C. and at relative moisture ca. 64%).

TABLE 15

Denim samples used in the bleaching test.

| Sample | Denim type | Source of denim | Enzyme used in the cellulase treatment |
|---|---|---|---|
| T1 | Tincan jeans | MASI Company Oy, Finland | Desized only, not cellulase treated |
| T2 | Tincan jeans | MASI Company Oy, Finland | Ecostone N400, AB Enzymes |
| T3 | Tincan jeans | MASI Company Oy, Finland | Ecostone L300, AB Enzymes |
| T4 | Tincan jeans | MASI Company Oy, Finland | Denimax 991S, Novozymes |
| L1 | Lee Cooper jeans | MASI Company Oy, Finland | Desized only, not cellulase treated |
| L2 | Lee Cooper jeans | MASI Company Oy, Finland | Ecostone L, AB Enzymes |
| L3 | Lee Cooper jeans | MASI Company Oy, Finland | Biotouch C29, AB Enzymes |
| L4 | Lee Cooper jeans | MASI Company Oy, Finland | Ecostone L, AB Enzymes |
| L5 | Lee Cooper jeans | MASI Company Oy, Finland | Indiage Max L, Genencor International |
| L6 | Lee Cooper jeans | MASI Company Oy, Finland | Indiage Super L, Genencor International |
| L7 | Lee Cooper jeans | MASI Company Oy, Finland | Ecostone CXP500 Exper., AB Enzymes |
| L8 | Lee Cooper jeans | MASI Company Oy, Finland | Ecostone CXP experimental, AB Enzymes |
| L9 | Lee Cooper jeans | MASI Company Oy, Finland | Ecostone N400, AB Enzymes |
| W1 | Warric jeans | Iki-Asu Oy, Finland | Desized only, not cellulase treated |
| W2 | Warric jeans | Iki-Asu Oy, Finland | Ecostone P4500, AB Enzymes |
| W3 | Warric jeans | Iki-Asu Oy, Finland | Indiage Max G, Genencor International |
| W4 | Warric jeans | Iki-Asu Oy, Finland | Ecostone NP2000, AB Enzymes |
| W5 | Warric jeans | Iki-Asu Oy, Finland | Ecostone L900, AB Enzymes |
| W6 | Warric jeans | Iki-Asu Oy, Finland | Denabraide MBL 65 E, Iogen |
| E1 | English jeans | English company | Desized only, not cellulase treated |
| E2 | English jeans | English company | Ecostone NP2000, AB Enzymes |
| E3 | English jeans | English company | Rocksoft NCE-EA, Dyadic |
| E4 | English jeans | English company | Rocksoft NCE-2X, Dyadic |

TABLE 15-continued

Denim samples used in the bleaching test.

| Sample | Denim type | Source of denim | Enzyme used in the cellulase treatment |
|---|---|---|---|
| E5 | English jeans | English company | Ecostone L900, AB Enzymes |
| E6 | English jeans | English company | Ecostone L900, AB Enzymes |
| E7 | English jeans | English company | Ecostone L900, AB Enzymes |
| B1 | Basic Jeans | MASI Company Oy, Finland | Ecostone P1250, AB Enzymes |

The laccase treatments were performed with Electrolux's Wascator FOM 71 CLS washer extractor under optimal conditions for each enzyme, described in Table 16. Methyl syringate (Example 7) was used as a mediator. Laccase was inactivated after draining by raising the pH above 11 by NaOH (10 min, 60° C.) and rinsing for three times. The fabrics were dried in a tumbler.

TABLE 16

The process parameters used in the bleaching test with TaLcc1 and DeniLite II Base laccase preparations.

| Process parameter | TaLcc1 laccase | DeniLite II Base laccase |
|---|---|---|
| Denim load | 1.5 kg | 1.5 kg |
| Water | 15 l | 15 l |
| Buffer | 37.5 g $Na_2HPO_4*2H_2O$ 14.7 g citric acid | 37.5 g $Na_2HPO_4*2H_2O$ 25.5 g citric acid |
| pH | 6 | 5 |
| Time | 30 min | 30 min |
| Temperature | 60° C. | 60° C. |
| Enzyme dosage | 100 nkat/g fabric | 100 nkat/g fabric |
| Mediator Dosage | 5 mg/g fabric | 5 mg/g fabric |

The sodium hypochlorite bleaching was performed with Electrolux's Wascator FOM 71 CLS washer extractor using denim obtained from the same jeans as in laccase treatments under conditions described in Table 17. Sodium hydroxide was added before adding 25 ml/l of 10% sodium hypochlorite solution (Klorite Forte, Farmos Oy) to keep the pH above 10.5 during the treatment. After draining the bleach liquor, there was one 2 minutes rinsing step with the liquor ratio of 1:20 before dechlorinating with sodium thiosulphate. After dechlorinating the denim samples were rinsed 3 times for 2 minutes with the liquor ratio of 1:20. The fabrics were dried in a tumbler.

TABLE 17

The process parameters used in the sodium hypochlorite bleaching and dechlorinating.

| Process parameter | NaOCl Bleaching | Dechlorinating |
|---|---|---|
| Denim load | 1.5 kg | 1.5 kg |
| Water | 22 l | 15 l |
| NaOH | 6.6 g | — |
| Sodium hypochlorite | 550 ml 10% NaOCl | — |
| Sodium thiosulphate | — | 30 g (2 g/l) |
| pH | 11.5-11.9 | |
| Treatment time | 15 min | 5 min |
| Temperature | 40° C. | 30° C. |

The bleaching effect was evaluated by measuring the colour as reflectance values as in Example 7. The results obtained are shown in Tables 18-20 and FIG. 11. The TaLcc1 laccase was superior compared to DeniLite II Base laccase (ca. 55-200% better) and sodium hypochlorite bleaching (even 60-115% better) under above mentioned conditions with all cellulase treated denim samples of each type. With fabrics that had only been desized the bleaching effect (increase of L* on the face side of denim) obtained with TaLcc1 preparation was equal or better than with the sodium hypochlorite and over 100% better than with DeniLite II Base. Different looks were obtained depending on the type of the denim and cellulase treatment used. "Sulphur-bottom type" denim was the most difficult to bleach.

TABLE 18

Colour measurements of the face side of denim treated with TaLcc1 laccase preparation (RF5597).

| | Before laccase Treatment | | After laccase treatment | | Increase |
|---|---|---|---|---|---|
| Sample No. | L* | b* | L* | b* | of L* |
| T1 | 25.02 | −12.75 | 34.82 | −16.36 | 9.80 |
| T2 | 28.20 | −16.20 | 42.70 | −14.60 | 14.50 |
| T3 | 29.08 | −17.04 | 47.09 | −14.04 | 18.01 |
| T4 | 27.16 | −16.26 | 43.53 | −15.18 | 16.37 |
| L1 | 20.21 | −16.14 | 33.13 | −19.41 | 12.92 |
| L2 | 31.81 | −19.08 | 50.89 | −13.17 | 19.08 |
| L3 | 28.45 | −19.38 | 47.66 | −14.82 | 19.21 |
| L4 | 29.42 | −19.31 | 48.39 | −13.83 | 18.97 |
| L5 | 28.49 | −18.82 | 47.73 | −14.28 | 19.24 |
| L6 | 29.54 | −18.64 | 46.71 | −14.68 | 17.17 |
| L7 | 27.20 | −19.02 | 42.95 | −16.23 | 15.75 |
| L8 | 29.46 | −19.04 | 46.73 | −14.86 | 17.27 |
| L9 | 28.80 | −18.73 | 45.02 | −14.91 | 16.22 |
| W1 | 18.03 | −13.04 | 28.54 | −17.55 | 10.51 |
| W2 | 26.12 | −17.08 | 42.16 | −14.48 | 16.04 |
| W3 | 28.55 | −16.63 | 44.08 | −13.66 | 15.53 |
| W4 | 26.22 | −16.13 | 39.54 | −14.72 | 13.32 |
| W5 | 23.97 | −17.54 | 40.49 | −15.38 | 16.52 |
| W6 | 24.01 | −17.01 | 39.58 | −15.62 | 15.57 |
| E1 | 17.47 | −10.05 | 22.71 | −13.97 | 5.24 |
| E2 | 25.48 | −14.75 | 35.99 | −14.08 | 10.51 |
| E3 | 25.26 | −15.91 | 36.52 | −14.46 | 11.26 |
| E4 | 27.04 | −15.91 | 38.79 | −13.94 | 11.75 |
| E5 | 25.19 | −15.32 | 37.53 | −14.03 | 12.34 |
| E6 | 22.54 | −14.90 | 34.17 | −14.79 | 11.63 |
| E7 | 22.84 | −15.72 | 36.00 | −14.95 | 13.16 |
| B1 | 29.48 | −14.67 | 47.19 | −12.75 | 17.71 |

L* indicates lightness,
−b* is the blue direction,
+b* is the yellow direction.

TABLE 19

Colour measurements of the face side of denim treated with DeniLite II Base laccase.

| | Before laccase Treatment | | After laccase Treatment | | Increase |
|---|---|---|---|---|---|
| Sample No. | L* | b* | L* | b* | of L* |
| T1 | 24.66 | −12.76 | 28.84 | −15.02 | 4.18 |
| T2 | 28.54 | −15.97 | 33.34 | −16.19 | 4.80 |
| T3 | 29.78 | −16.94 | 37.86 | −16.80 | 8.08 |
| T4 | 27.68 | −15.70 | 35.00 | −16.79 | 7.32 |
| L1 | 19.99 | −16.35 | 25.75 | −18.94 | 5.76 |
| L2 | 32.70 | −18.39 | 43.80 | −15.74 | 11.10 |

TABLE 19-continued

Colour measurements of the face side of denim treated with DeniLite II Base laccase.

| Sample No. | Before laccase Treatment | | After laccase Treatment | | Increase of L* |
|---|---|---|---|---|---|
| | L* | b* | L* | b* | |
| L3 | 28.67 | −18.94 | 39.27 | −17.47 | 10.60 |
| L4 | 29.40 | −19.40 | 40.28 | −17.19 | 10.88 |
| L5 | 28.29 | −19.10 | 39.14 | −17.26 | 10.85 |
| L6 | 29.74 | −18.84 | 40.48 | −16.45 | 10.74 |
| L7 | 27.70 | −18.73 | 35.54 | −18.26 | 7.84 |
| L8 | 29.86 | −18.71 | 40.39 | −16.80 | 10.53 |
| L9 | 28.95 | −18.71 | 38.85 | −16.89 | 9.90 |
| W1 | 18.67 | −12.81 | 23.04 | −16.09 | 4.37 |
| W2 | 26.62 | −16.80 | 35.70 | −15.85 | 9.08 |
| W3 | 28.06 | −16.83 | 36.90 | −15.48 | 8.84 |
| W4 | 26.42 | −16.27 | 33.25 | −15.53 | 6.83 |
| W5 | 24.28 | −17.43 | 33.47 | −16.62 | 9.19 |
| W6 | 24.32 | −17.14 | 33.00 | −16.66 | 8.68 |
| E1 | 16.94 | −9.80 | 19.11 | −12.36 | 2.17 |
| E2 | 25.49 | −14.17 | 31.54 | −14.34 | 6.05 |
| E3 | 24.97 | −15.82 | 32.23 | −14.90 | 7.26 |
| E4 | 27.47 | −15.23 | 34.26 | −14.76 | 6.79 |
| E5 | 24.42 | −15.68 | 32.37 | −15.02 | 7.95 |
| E6 | 22.58 | −14.91 | 29.30 | −15.11 | 6.72 |
| E7 | 22.76 | −15.56 | 30.73 | −15.26 | 7.97 |
| B1 | 28.65 | −14.84 | 36.29 | −14.95 | 7.64 |

L* indicates lightness,
−b* is the blue direction,
+b* is the yellow direction.

TABLE 20

Colour measurements of the face side of denim treated with sodium hypochlorite.

| Sample No. | Before laccase Treatment | | After laccase Treatment | | Increase of L* |
|---|---|---|---|---|---|
| | L* | b* | L* | b* | |
| T1 | 25.02 | −12.87 | 33.97 | −17.95 | 8.95 |
| T2 | 27.65 | −16.05 | 34.38 | −18.22 | 6.73 |
| T3 | 29.09 | −16.80 | 40.33 | −18.30 | 11.24 |
| T4 | 27.56 | −16.00 | 37.66 | −18.58 | 10.10 |
| L1 | 20.54 | −16.12 | 31.23 | −20.83 | 10.69 |
| L2 | 31.14 | −19.03 | 44.11 | −18.60 | 12.97 |
| L3 | 28.45 | −18.64 | 39.71 | −19.67 | 11.26 |
| L4 | 29.15 | −19.26 | 40.63 | −19.25 | 11.48 |
| L5 | 28.00 | −19.01 | 39.47 | −19.48 | 11.47 |
| L6 | 29.08 | −18.61 | 41.50 | −18.68 | 12.42 |
| L7 | 26.76 | −19.03 | 37.91 | −19.85 | 11.15 |
| L8 | 28.76 | −18.67 | 40.74 | −19.12 | 11.98 |
| L9 | 28.91 | −18.40 | 40.82 | −18.82 | 11.91 |
| W1 | 17.58 | −13.07 | 27.75 | −18.76 | 10.17 |
| W2 | 25.59 | −17.16 | 39.35 | −17.39 | 13.76 |
| W3 | 28.12 | −16.57 | 41.11 | −16.79 | 12.99 |
| W4 | 25.78 | −16.11 | 38.07 | −17.33 | 12.29 |
| W5 | 23.72 | −17.39 | 37.12 | −18.03 | 13.40 |
| W6 | 23.75 | −16.81 | 36.65 | −17.95 | 12.90 |
| E1 | 16.76 | −10.10 | 21.91 | −15.03 | 5.15 |
| E2 | 25.49 | −14.17 | 33.30 | −16.43 | 7.36 |
| E3 | 24.73 | −15.52 | 34.13 | −16.73 | 9.40 |
| E4 | 26.55 | −15.56 | 35.83 | −16.86 | 9.28 |
| E5 | 24.57 | −15.48 | 33.85 | −16.48 | 9.28 |
| E6 | 22.20 | −14.48 | 30.61 | −16.65 | 8.41 |
| E7 | 22.74 | −15.52 | 32.36 | −16.75 | 9.62 |
| B1 | 28.35 | −15.21 | 40.62 | −17.37 | 12.27 |

L* indicates lightness,
−b* is the blue direction,
+b* is the yellow direction.

EXAMPLE 11

Stain Removal with Laccases

The TaLcc1 (RF5598) and Denilite II Base laccase preparations were tested for their ability to remove stains. The following artificially soiled test cloths were used: grass soiling (Art. 164, EMPA Testmaterialen, Germany), tea soiling (Art. 167, EMPA Testmaterialen, Germany). The fabric was cut in 5.8×5.8 cm swatches. Laccase treatments were performed in LP-2 Launder Ometer as follows. About 5 g of soiled fabrics were loaded into 1.2 liter containers containing 150 ml Mc Ilvaine's citrate phosphate buffer pH 6 and the containers were temperated. Enzymes with or without the mediator (methyl syringate, DeniLite II Assist, Novozymes) were dosed as laccase activity units (Example 7). Enzyme dosage was 200 nkat/g and mediator dosage 10 mg/g of the weight of fabric, except at 40° C. also dosages of 20 nkat/g and 2 mg/g were used. The Launder Ometer was run at 40, 50 or 60° C. and pH 6 for 60 min. After that the swatches were carefully rinsed under running water and in shake flasks containing warm water and dried in the air.

The stain removal effect was evaluated by measuring the colour as reflectance values using L*a*b* color space coordinates (Example 7). The colour of the swatches was measured before and after the laccase treatment.

The results of the stain removal tests are shown in Table 21, Table 22 and FIGS. 12-15. The TaLcc1 preparation was more effective in removal of grass soiling with the mediator at 60° C. (highest a*-value=least green, highest lightness L*) than DeniLite II (FIG. 12, Table 21). The result looked the best also by visual estimation. TaLcc1 was slightly better than DenLite at 40° C. too (FIG. 14, Table 22). Without the mediator the efficiency in removal of grass stain was low.

TaLcc1 laccase was also more efficient in removal of tea stain at 60° C. with the mediator than DeniLite, that can be seen in the highest lightness and the lowest redness values in FIG. 13 and Table 21 and also by visual estimation. TaLcc1 was slightly better at 40° C., especially with higher dosage, too (FIG. 15, Table 22). Without the mediator the laccases did not have a notable effect on tea stain. Removal of grass and tea stains was more difficult at 40° C. than at higher temperatures.

TABLE 21

Colour measurements of stain removal test with laccases at 50 and 60° C..

| Sample | Enzyme nkat/g | Mediator mg/g | Conditions | Grass | | | Tea | | |
|---|---|---|---|---|---|---|---|---|---|
| | | | | L* | a* | b* | L* | a* | b* |
| Artificially soiled cloth (untreated) | — | — | — | 78.32 | −10.18 | 25.31 | 69.27 | 8.56 | 25.80 |
| TaLcc1 | 200 | 10 | 60 min, 60° C., pH 6 | 80.6 | 0.02 | 18.71 | 81.69 | 2.91 | 22.29 |
| TaLcc1 | 200 | 0 | 60 min, 60° C., pH 6 | 79.38 | −4.19 | 17.77 | 76.98 | 4.98 | 21.20 |

TABLE 21-continued

Colour measurements of stain removal test with laccases at 50 and 60° C..

| Sample | Enzyme nkat/g | Mediator mg/g | Conditions | Grass L* | a* | b* | Tea L* | a* | b* |
|---|---|---|---|---|---|---|---|---|---|
| DeniLite | 200 | 10 | 60 min, 60° C., pH 6 | 80.26 | −0.91 | 18.46 | 80.42 | 3.29 | 21.92 |
| DeniLite | 200 | 0 | 60 min, 60° C., pH 6 | 79.53 | −4.69 | 18.33 | 75.91 | 5.39 | 22.09 |
| Mediator only | 0 | 10 | 60 min, 60° C., pH 6 | 77.98 | −6.80 | 19.26 | 75.54 | 5.00 | 20.50 |
| Buffer only | 0 | 0 | 60 min, 60° C., pH 6 | 77.93 | −6.70 | 19.31 | 75.55 | 4.94 | 20.58 |
| TaLcc1 | 200 | 10 | 60 min, 50° C., pH 6 | 80.60 | −0.18 | 17.65 | 79.52 | 3.45 | 23.74 |
| Mediator only | 0 | 10 | 60 min, 50° C., pH 6 | 77.95 | −6.45 | 18.56 | 75.97 | 4.84 | 20.47 |

L* indicates lightness,
−b* is the blue direction,
+b* is the yellow direction,
+a* is the red direction,
−a* is the green direction).
Untreated artifially soiled test cloth and mediator and buffer controls were used for comparision.

TABLE 22

Colour measurements of stain removal test with laccases at 40° C..

| Sample | Enz. dosage nkat/g | Mediator mg/g | Conditions | Grass L* | a* | b* | Tea L* | a* | b* |
|---|---|---|---|---|---|---|---|---|---|
| Artificially soiled cloth (untreated) | — | — | — | 78.18 | −8.88 | 25.29 | 69.36 | 8.65 | 25.80 |
| TaLcc1 | 200 | 10 | 60 min, 40° C., pH 6 | 80.34 | 0.47 | 16.51 | 78.77 | 3.93 | 24.97 |
| DeniLite | 200 | 10 | 60 min, 40° C., pH 6 | 80.07 | −0.22 | 16.40 | 77.37 | 4.36 | 24.67 |
| Mediator only | 0 | 10 | 60 min, 40° C., pH 6 | 78.88 | −6.19 | 18.28 | 74.72 | 5.63 | 22.16 |
| TaLcc1 | 200 | 0 | 60 min, 40° C., pH 6 | 80.25 | −4.22 | 17.41 | 75.99 | 5.59 | 23.54 |
| DeniLite | 200 | 0 | 60 min, 40° C., pH 6 | 80.25 | −4.60 | 17.55 | 76.07 | 5.45 | 22.94 |
| Mediator only | 0 | 10 | 60 min, 40° C., pH 6 | 80.1 | −5.67 | 17.68 | 76.25 | 5.11 | 22.15 |
| Buffer only | 0 | 0 | 60 min, 40° C., pH 6 | 79.66 | −5.79 | 18.45 | 76.00 | 5.22 | 22.74 |
| TaLcc1 | 20 | 2 | 60 min, 40° C., pH 6 | 80.16 | −0.73 | 16.20 | 77.17 | 4.65 | 24.40 |
| DeniLite | 20 | 2 | 60 min, 40° C., pH 6 | 79.65 | −1.18 | 16.32 | 77.01 | 4.81 | 24.49 |
| Mediator only | 0 | 2 | 60 min, 40° C., pH 6 | 79.32 | −6.43 | 18.64 | 74.71 | 5.94 | 22.99 |

L* indicates lightness,
−b* is the blue direction,
+b* is the yellow direction,
+a* is the red direction,
−a* is the green direction).
Untreated artifially soiled test cloth and mediator and buffer controls were used for comparision.

EXAMPLE 12

Decolorization of Dyes Using TaLcc1 Laccase Preparation

The TaLcc1 laccase preparation from strain RF5597 was tested for its ability to decolourize different dyes in the presence or absence of the methyl syringate mediator (Example 7). The experiments were carried out in 250 ml shake flasks containing 100 ml of dye dissolved in citrate phosphate buffer pH 6. Dye concentration 12 mg/100 ml was used. Enzyme was dosed 200 nkat (or 20 nkat) per 100 ml and the mediator 10 (or 1) mg per 100 ml. The shake flasks were incubated at 50° C. for 30, 90 and 150 minutes. Samples of 3.5 ml were taken in test tubes for visual evaluation.

The results in Table 23 show that TaLcc1 laccase is able to decolorize Indigocarmine, Remazol Brilliant Blue (Reactive Blue 19) and Cibacron Brilliant Red 3B-P to great extend and Pontamine Bast Orange to some extend in the presence of the mediator. Decolourization of Indigocarmine was very fast, and the blue colour had turned to light yellow earlier than in 30 min. The reaction seemed to be completed in 90 min with all dyes, since no changes in the colours of the samples was detected after a prolonged incubation.

TABLE 23

Decolorization of dyes with TaLcc1 (RF5597) laccase preparation.

| Dye 12 mg/100 ml | Enz. dosage nkat/100 ml | Mediator mg/100 ml | Time 30 min | Time 90 min |
|---|---|---|---|---|
| Remazol Brilliant Blue (Sigma) | 200 | 0 | − | − |
| Remazol Brilliant Blue (Sigma) | 200 | 10 | ++ | ++ |
| Remazol Brilliant Blue (Sigma) | 20 | 0 | − | − |
| Remazol Brilliant Blue (Sigma) | 20 | 1 | − | − |
| Cibacron Brilliant Red 3B-P (Ciba-Geigy) | 200 | 0 | − | − |
| Cibacron Brilliant Red 3B-P (Ciba-Geigy) | 200 | 10 | +++ | +++ |
| Indigocarmine (Merck) | 200 | 0 | − | − |
| Indigocarmine (Merck) | 200 | 10 | +++ | +++ |
| Indigocarmine (Merck) | 20 | 1 | + | +++ |
| Pontamine Bast Orange GRN | 200 | 0 | − | − |
| Pontamine Bast Orange GRN | 200 | 10 | + | + |

Treatment time 30 and 60 min.
− no visually detectable change,
+ visually detectable fading of the colour,
++ considerable fading of the colour,
+++ complete/almost complete decolorization.

REFERENCES

Aho S, V Olkkonen, T Jalava, M Paloheimo, R Bühler, M-L Niku-Paavola, E H Bamford and M Korhola. 1991. Monoclonal antibodies against core and cellulose-binding domains of *Trichoderma reesei* cellobiohydrolases I and II and endoglucanase I. Eur. J. Biochem. 200:643-649.

Altschul S F, W Gish, W Miller, E W Myers and D J Lipman. 1990. Basic local alignment search tool. J. Mol. Biol. 215: 403-410.

Edman P and G Begg. 1967. A protein sequenator. Eur. J. Biochem. 1:80-91.

Gasteiger, E, A Gattiker, C Hoogland, I Ivanyi, R D Appel and A Bairoch. 2003. ExPASy: the proteiomics server for in-depth protein knowledge and analysis. Nucleic Acids Res. 31:3784-3788.

Joutsjoki, V V, T K Torkkeli, and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24:223-228.

Karhunen T, A Mäntylä, K M H Nevalainen, and P L Suominen. 1993. High frequency one-step gene replacement in *Trichoderma reesei*. I. Endoglucanase I overproduction. Mol. Gen. Genet. 241:515-522.

Kiiskinen, L-L, M Rättö and K Kruus. 2004. Screening for novel laccase-producing microbes. J. Appl. Microbiol. 97:640-646.

Laemmli U K. 1970. Cleavage of structural proteins during the assembly of the head of bacteriophage T4. Nature 227: 680-685.

Leonowicz, A and K Grzywnowicz. 1981. Quantitative estimation of laccase forms in some white-rot-fungi using syringaldazine as a substrate. Enzyme Microb. Technol. 3:55-58.

Lowry O H, N J Roseborough, A L Farr and R J Randall. 1951. Protein measurement with the Folin phenol reagent. J. Biol Chem 193: 265-275.

Malardier L, M J Daboussi, J Julien, F Roussel, C Scazzocchio and Y Brygoo. 1989. Gene 15:147-156.

Mueller M and C Shi. 2000. Laccase for decorization of indigo in denim processing, AATCC, 2000 International conference and exhibition.

Nielsen H, J Engelbrecht, S Brunak and G von Heijne. 1997. Identification of prokaryotic and eukaryotic signal peptides and prediction of their cleavage sites. Protein Engineering 10:1-6.

Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.

Niku-Paavola M-L, E Karhunen, P Salola, V Raunio. 1988. Ligninolytic enzymes of the white-rot fungus *Phlebia radiata*. Biochem J 254: 877-884.

Paloheimo M, A Mäntylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Palonen H, M Saloheimo, L Viikari and K Kruus. 2003. Purification, characterization and sequence analysis of a laccase from the ascomycete *Mauginiella* sp. Enzyme Microb. Technol. 31:403-410.

Paszczynski A, V-B Huynh and R Crawford. 1985. Enzymatic activities of an extracellular Mn-dependent peroxidase from *Phanerocahete chrysosporium*. FEMS Microbiol Lett 29: 37-41.

Penttilä M, H Nevalainen, M Rättö, E Salminen, and J Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Rice P, I Longden and A Bleasby. 2000. EMBOSS: The European Molecular Biology Open Software Suite. Trends in Genetics 16:276-277.

Sambrook J, E F Fritsch, and T Maniatis. 1989. Molecular cloning, a laboratory manual. Cold Spring Harbor Laboratory, New York, U.S.

Sambrook J and D W Russell. 2001. Molecular cloning, a laboratory manual. Cold Spring Harbor Laboratory, New York, US.

Schlosser D, R Grey R and W Fritsche. 1997. Patterns of ligninolytic enzymes in *Trametes versicolor*. Distribution of extra- and intracellular enzyme activities during cultivation on glucose, wheat straw and beech wood. Appl Microbiol Biotechnol 47: 412-418.

Sigoillot C, E Record, V Belle, J L Robert, A Levasseur, P Punt, CAM van der Hondel, A Fourner, J C Sigoillot and M Aster. 2004. Natural and recombinant laccases for pulp and paper bleaching, Appl. Microbiol. Biotechnol. 64: 346-352.

Stone K L, M B Lobresti, N D Williams, J M Crawford, R Deangelis and K R Williams. In Techniques in Protein Chemistry, p. 377-391. T. E. Hugli (ed.). Academic Press, New York 1988.

What is claimed is:

1. A recombinant polypeptide having laccase activity, characterized in that it consists of the amino acid sequence SEQ ID NO: 12 or a sequence showing at least 90% identity over the entire length of sequence SEQ ID NO: 12, wherein an enzyme treatment for increasing lightness of desized denim is carried out at temperature 30-80° C.

2. The polypeptide according to claim 1, wherein the polypeptide is obtainable from genus *Thielavia*.

3. The polypeptide according to claim 1, wherein the polypeptide is encoded by the sequence in pALK1342 deposited in *E. coli* RF5473 under the number DSM 15484.

4. The polypeptide according to claim 1, wherein optimum pH for laccase activity is at pH 3.5 to 8.

5. The polypeptide according to claim 4, wherein pH optimum for the laccase activity is about pH 5.5.

6. The polypeptide according to claim 1, wherein the polypeptide is produced in a host of the genus *Trichoderma* or *Aspergillus*.

7. The polypeptide according to claim 1, wherein an enzyme treatment for increasing lightness of desized denim is carried out by a single treatment and the lightness of denim is increased at least as many units as denim treated by sodium hypochlorite.

8. The polypeptide according to claim 7, wherein the sodium hypochlorite treatment is carried out in the presence of 25 ml/l of 10% sodium hypochlorite (NaOCl) solution for 15 minutes, at the temperature 40° C., at pH above 10.5, in liquor ratio about 1:15, by using equipment normally used in wet processes in textile industry.

9. The polypeptide according to claim 7, wherein the laccase treatment is carried out in the presence of one or more mediators.

10. The polypeptide according to claim 7, wherein the enzyme treatment of denim does not cause any essential strength loss.

11. The polypeptide according to claim 7, wherein the enzyme treatment of denim does not cause the loss of abraded look.

12. The polypeptide according to claim 1, wherein the laccase activity is effective in stain removal.

13. The polypeptide according to claim 1, wherein the laccase activity decolorizes dyes.

14. A nucleic acid sequence, characterized in that it encodes the polypeptide as defined in claim 1.

15. A vector, characterized in that it comprises the nucleic acid sequence according to claim 14.

16. The vector according to claim 15, wherein the nucleic acid sequence has been operably linked to expression control sequences allowing expression in prokaryotic or eukaryotic host cells.

17. A host cell, characterized in that or the vector according to claim 15 has been introduced into the host cell.

18. The host cell according to claim 17, wherein the host cell is a microbial host cell.

19. The host cell according to claim 18, wherein the host cell belongs to the genus *Trichoderma* or *Aspergillus*.

20. A process for the production of a polypeptide having laccase activity, comprising the steps of culturing the host cell of claim 17, and recovering the polypeptide.

21. A polypeptide having laccase activity further being obtainable by the process according to claim 20.

22. A process for obtaining an enzyme preparation comprising a polypeptide of claim 21 said process comprising the steps of culturing a host cell and either recovering the polypeptide from the cells or separating the cells from the culture medium and obtaining the supernatant.

* * * * *

SEQUENCE LISTING

```
<160> NUMBER OF SEQ ID NOS: 12

<210> SEQ ID NO 1
<211> LENGTH: 19
<212> TYPE: PRT
<213> ORGANISM: Thielavia arenaria ALKO4197
<220> FEATURE:
<221> NAME/KEY: MISC_FEATURE
<222> LOCATION: (1)..(19)
<223> OTHER INFORMATION: Sequence of Peptide 1, a tryptic peptide from
      Thielavia arenaria ALKO 4197 TaLcc1 protein
<220> FEATURE:
<221> NAME/KEY: MISC_FEATURE
<222> LOCATION: (12)..(12)
<223> OTHER INFORMATION: Xaa may be Gln or Ile
```

<400> SEQUENCE: 1

Tyr Gln Gly Ala Pro Asn Thr Leu Pro Thr Asn Xaa Gly Leu Pro Val
1               5                   10                  15

Pro Asn His

<210> SEQ ID NO 2
<211> LENGTH: 11
<212> TYPE: PRT
<213> ORGANISM: Thielavia arenaria ALKO4197
<220> FEATURE:
<221> NAME/KEY: MISC_FEATURE
<222> LOCATION: (1)..(11)
<223> OTHER INFORMATION: Sequence of Peptide 2, a tryptic peptide from
      Thielavia arenaria ALKO 4197 Ta Lcc1 protein

<400> SEQUENCE: 2

Glu Asn Trp Ile Gly Pro Asp Gly Val Leu Lys
1               5                   10

<210> SEQ ID NO 3
<211> LENGTH: 9
<212> TYPE: PRT
<213> ORGANISM: Thielavia arenaria ALKO 4197
<220> FEATURE:
<221> NAME/KEY: MISC_FEATURE
<222> LOCATION: (1)..(9)
<223> OTHER INFORMATION: Sequence of Peptide 3, a tryptic peptide from
      Thielavia arenaria ALKO4197 Ta Lcc1 protein
<220> FEATURE:
<221> NAME/KEY: MISC_FEATURE
<222> LOCATION: (1)..(1)
<223> OTHER INFORMATION: S is unsure

<400> SEQUENCE: 3

Ser Leu Phe Leu Ala Val Gly Gln Arg
1               5

<210> SEQ ID NO 4
<211> LENGTH: 26
<212> TYPE: DNA
<213> ORGANISM: artificial
<220> FEATURE:
<223> OTHER INFORMATION: Sequence of oligonucleotide primer POX26

<400> SEQUENCE: 4
gagaactgga tcggycccga yggygt                                    26

<210> SEQ ID NO 5
<211> LENGTH: 17
<212> TYPE: DNA
<213> ORGANISM: artificial
<220> FEATURE:
<223> OTHER INFORMATION: Sequence of  oligonucleotide primer POX27
<220> FEATURE:
<221> NAME/KEY: misc_feature
<222> LOCATION: (15)..(15)
<223> OTHER INFORMATION: n can be c or i

<400> SEQUENCE: 5
garaaytgga thggncc                                              17

<210> SEQ ID NO 6
<211> LENGTH: 20
<212> TYPE: DNA
<213> ORGANISM: artificial
<220> FEATURE:
<223> OTHER INFORMATION: Sequence of oligonucleotide primer 28

```
<400> SEQUENCE: 6
ctcttcctcg cygtsggyca                                              20

<210> SEQ ID NO 7
<211> LENGTH: 20
<212> TYPE: DNA
<213> ORGANISM: artificial
<220> FEATURE:
<223> OTHER INFORMATION: Sequence of oligonucleotide primer POX29

<400> SEQUENCE: 7
tgrccsacrg cgaggaagag                                              20

<210> SEQ ID NO 8
<211> LENGTH: 20
<212> TYPE: DNA
<213> ORGANISM: artificial
<220> FEATURE:
<223> OTHER INFORMATION: Sequence of oligonucleotide sequence POX30

<400> SEQUENCE: 8
taccagggyg cyccsaacac                                              20

<210> SEQ ID NO 9
<211> LENGTH: 20
<212> TYPE: DNA
<213> ORGANISM: artificial
<220> FEATURE:
<223> OTHER INFORMATION: Sequence of oligonucleotide primer POX 31

<400> SEQUENCE: 9
gtgttsggrg crccctggta                                              20

<210> SEQ ID NO 10
<211> LENGTH: 1057
<212> TYPE: DNA
<213> ORGANISM: Thielavia arenaria ALKO4197
<220> FEATURE:
<221> NAME/KEY: misc_feature
<222> LOCATION: (1)..(1057)
<223> OTHER INFORMATION: Sequence of the PCR fragment obtained from
      Thielavia arenaria ALKO4197 using the primers POX27 and POX31

<400> SEQUENCE: 10
gagaactgga tcgggcccga tggcgttctc aagaatgtgg tgatgttggt caatggtacg      60
ttgatgtcca attctgtata aagagaagaa acgtgctgat acgctccctt cgtctagaca     120
agattatagg tatgttgtca aacccgctgt aaccccaacc gccaagacct ggaggctcct     180
cgcctggacg tgttgtacaa tatgctgacc tcgccgccag ggccaaccat ccgcgcgaac     240
tggggtgaca atatcgaagt cactgtcatc aacaatctca aaaccaatgg gtacgaccac     300
ttgaatcatc ccgggcctac ccctaacaca aaatctcaac gtgcatccga tctgacgtat     360
tatatccatc tagtacctcg atgcactggc atggccttcg tcagctgggt aacgttttca     420
acgacggtgc caacggcgtg actgagtgcc caatcccgcc caaaggaggg cgcaagacgt     480
acaagttccg tgcgacacag tatggcacca gctggtatca ctcccacttc tcggcccagt     540
acggcaacgg cgtggtcggc accatccaga tcgacggccc tgcctctctg ccatatgaca     600
ttgatctggg cgtgttccct ctcatggact actactacag gtcggccgat gagctggtgc     660
acttcaccca gagcaacggc gcccgccaa gcgacaacgt cctcttcaat ggcaccgccc     720
gtcaccctga cgggggca ggccagtggt acaacgtcac gctgactcca ggcaagcgac     780
accgcctgcg catcatcaac acgtcgaccg acaaccactt tcaggtgtcg cttgtcggcc     840
```

```
acaacatgac cgtcattgcc accgacatgg tccccgtcaa cgcctttact gtcagcagcc    900
tattcctcgc cgtaggccag cgatacgatg tcaccatcga cgccaatagc ccggtgggca    960
actactggtt caacgtgact ttcggcgatg ggttgtgcgg ctccagtaac aacaaattcc   1020
cagccgccat cttccgctac cagggcgccc cgaacac                           1057

<210> SEQ ID NO 11
<211> LENGTH: 2680
<212> TYPE: DNA
<213> ORGANISM: Thielavia arenaria ALKO 4197
<220> FEATURE:
<221> NAME/KEY: misc_feature
<222> LOCATION: (1)..(2680)
<223> OTHER INFORMATION: Nucleotide sequence of of Thielavia arenaria
      ALKO 4197 laccase 1 gene (Ta lcc1).
<220> FEATURE:
<221> NAME/KEY: misc_feature
<222> LOCATION: (178)..(2456)
<223> OTHER INFORMATION: Talcc1
<220> FEATURE:
<221> NAME/KEY: Intron
<222> LOCATION: (406)..(456)
<220> FEATURE:
<221> NAME/KEY: Intron
<222> LOCATION: (536)..(597)
<220> FEATURE:
<221> NAME/KEY: Intron
<222> LOCATION: (610)..(700)
<220> FEATURE:
<221> NAME/KEY: Intron
<222> LOCATION: (771)..(853)
<220> FEATURE:
<221> NAME/KEY: Intron
<222> LOCATION: (1824)..(1902)
<220> FEATURE:
<221> NAME/KEY: Intron
<222> LOCATION: (1975)..(2033)

<400> SEQUENCE: 11
ggatccccgg gtcagtctat ataaggggct gagtgtccag ctcttccatg cctttgattc     60
tcttgaatca ccaggacact cgggcggctt cagtcttgca taactcgggt cttcccttcc    120
tctcactgct tttcttcgct cagatatatt tcaggcgacc tcaaacagct cgccatcatg    180
aagtcttggg ccgccgccgt ggcgctcatg gtgggcattc tcagccctca tgctgccgcc    240
gcacctcctg caaacccggt ccagagagac atgctccagg tccttgaggc gagacagtct    300
ggcccgactt gcaacacccc gtccaatcgt gcgtgctgga ccaatggttt cgacatcaac    360
accgactatg aagtcagcac tcctaatacc ggacgtactg tggccgtaag cttcccctcc    420 cttttaaggag gcagagctag gactaacaag caccagtacc aacttaccct cactgagaaa    480
gagaactgga tcggtcccga tggcgttctc aagaatgtgg tgatgttggt caatggtacg    540
ttgatgtcca attctgtata aagagaagaa acgtgctgat cgctcccctt cgtctagaca    600
agattatagg tatgttgtca aacccgctgt aaccccaacc gccaagacct ggaggctcct    660
cgcctggacg tgttgtacaa tatgctgacc tcgccgccag ggccaaccat ccgcgcgaac    720
tggggtgaca atatcgaagt cactgtcatc aacaatctca aaaccaatgg gtacgaccac    780
ttgaatcatc ccgggcctac ccctaacaca aaatctcaac gtgcatccga tctgacgtat    840
tatatccatc tagtacctcg atgcactggc atggccttcg tcagctgggt aacgttttca    900
acgacggtgc caacggcgtg actgagtgcc caatcccgcc caaggagggc gcaagacgt    960 acaagttccg tgcgacacag tatggcacca gctggtatca ctcccacttc tcggcccagt   1020
acggcaacgg cgtggtcggc accatccaga tcgacggccc tgcctctctg ccatatgaca   1080
```

```
ttgatctggg cgtgttccct ctcatggact actactacag gtcggccgat gagctggtgc    1140
acttcaccca gagcaacggc gccccgccaa gcgacaacgt cctcttcaat ggcaccgccc    1200
gtcaccctga cggggggca ggccagtggt acaacgtcac gctgactcca ggcaagcgac    1260
accgcctgcg catcatcaac acgtcgaccg acaaccactt tcaggtgtcg cttgtcggcc    1320
acaacatgac cgtcattgcc accgacatgg tccccgtcaa cgcctttact gtcagcagcc    1380
tattcctcgc cgtaggccag cgatacgatg tcaccatcga cgccaatagc ccggtgggca    1440
actactggtt caacgtgact tcggcgatg ggttgtgcgg ctccagtaac aacaaattcc    1500
cagccgccat cttccgctac cagggcgccc ccgctacgct cccgacggat cagggtctac    1560
ccgtgcccaa tcacatgtgt ttggacaacc tgaacctaac tcctgtggtg acacggagcg    1620
cgcccgtcaa caactttgtc aagcgtccgt ccaacacgct gggcgtcact ctcgatatcg    1680
gcggcacgcc gctctttgtg tggaaggtca acggcagcgc catcaacgtc gactggggca    1740
agccgatcct tgactatgtc atgagcggca cacgagcta cccggtcagc gataacattg    1800
tgcaggtgga cgctgttgac caggtacgcc cctcttgaag cccctagcag ttcacgctag    1860
tatacaatac aagtacatgc taacacttcc ctccctattc agtggactta ctggctgatc    1920
gagaacgacc cgaccaatcc cattgtcagc ttgccgcacc cgatgcatct gcacgtacgt    1980
tcaaacctcc ccccacccc cacttcatac aaaatatact gacaaatcga cagggccacg    2040
acttcctcgt cctgggccga tcacccgacg agctccccag cgcgggggtc cgtcacatct    2100
ttgacccggc caaggacctg ccccggctta agggcaacaa ccccgtgcgg cgggacgtga    2160
cgatgcttcc ggcgggcggc tggctgctgc tggcgttcaa gacggacaac ccgggcgcat    2220
ggctgttcca ctgccacatt gcgtggcacg tgtcgggcgg cctgtcggtc gacttcctcg    2280
agcggcccaa cgaccttcgc acgcagctca acagcaacgc caagcgcgcc gaccgcgacg    2340
acttcaaccg cgtctgccgc gagtggaacg cctactggcc taccaacccg ttccccaaga    2400
tcgactcggg cttgaggcac cggtttgttg aggagagcga gtggatggtt cgctaaactg    2460
cctggctgtg ccaattgatt tgatgggtac atgtacctgt tggtgttact gttgacgagg    2520
ctgtgtaagt accatggcaa aggggtgttt tcaggggtgc tctgggggtaa ttggcacagt    2580 acatggaggg gtctggggtt gggtatacaa ggcttgctgc tccgttttta tcttttggct    2640
tgattaagac tttcttgtct gatgtacgag tcaggccgcc                          2680
```

<210> SEQ ID NO 12
<211> LENGTH: 617
<212> TYPE: PRT
<213> ORGANISM: Thielavia arenaria ALKO4197
<220> FEATURE:
<221> NAME/KEY: MISC_FEATURE
<222> LOCATION: (1)..(617)
<223> OTHER INFORMATION: Deduced amino acid sequence of Thielavia
      arenaria ALKO4197 laccase 1 (Ta Lcc1)

<400> SEQUENCE: 12

Met Lys Ser Trp Ala Ala Val Ala Leu Met Val Gly Ile Leu Ser
1               5                   10                  15

Pro His Ala Ala Ala Pro Pro Ala Asn Pro Val Gln Arg Asp Met
            20                  25                  30

Leu Gln Val Leu Glu Ala Arg Gln Ser Gly Pro Thr Cys Asn Thr Pro
        35                  40                  45

Ser Asn Arg Ala Cys Trp Thr Asn Gly Phe Asp Ile Asn Thr Asp Tyr
    50                  55                  60

Glu Val Ser Thr Pro Asn Thr Gly Arg Thr Val Ala Tyr Gln Leu Thr

```
            65                  70                  75                  80
Leu Thr Glu Lys Glu Asn Trp Ile Gly Pro Asp Gly Val Leu Lys Asn
                    85                  90                  95

Val Val Met Leu Val Asn Asp Lys Ile Ile Gly Pro Thr Ile Arg Ala
                100                 105                 110

Asn Trp Gly Asp Asn Ile Glu Val Thr Val Ile Asn Asn Leu Lys Thr
                115                 120                 125

Asn Gly Thr Ser Met His Trp His Gly Leu Arg Gln Leu Gly Asn Val
            130                 135                 140

Phe Asn Asp Gly Ala Asn Gly Val Thr Glu Cys Pro Ile Pro Pro Lys
145                 150                 155                 160

Gly Gly Arg Lys Thr Tyr Lys Phe Arg Ala Thr Gln Tyr Gly Thr Ser
                165                 170                 175

Trp Tyr His Ser His Phe Ser Ala Gln Tyr Gly Asn Gly Val Val Gly
                180                 185                 190

Thr Ile Gln Ile Asp Gly Pro Ala Ser Leu Pro Tyr Asp Ile Asp Leu
            195                 200                 205

Gly Val Phe Pro Leu Met Asp Tyr Tyr Tyr Arg Ser Ala Asp Glu Leu
            210                 215                 220

Val His Phe Thr Gln Ser Asn Gly Ala Pro Pro Ser Asp Asn Val Leu
225                 230                 235                 240

Phe Asn Gly Thr Ala Arg His Pro Glu Thr Gly Ala Gly Gln Trp Tyr
                245                 250                 255

Asn Val Thr Leu Thr Pro Gly Lys Arg His Arg Leu Arg Ile Ile Asn
                260                 265                 270

Thr Ser Thr Asp Asn His Phe Gln Val Ser Leu Val Gly His Asn Met
            275                 280                 285

Thr Val Ile Ala Thr Asp Met Val Pro Val Asn Ala Phe Thr Val Ser
            290                 295                 300

Ser Leu Phe Leu Ala Val Gly Gln Arg Tyr Asp Val Thr Ile Asp Ala
305                 310                 315                 320

Asn Ser Pro Val Gly Asn Tyr Trp Phe Asn Val Thr Phe Gly Asp Gly
                325                 330                 335

Leu Cys Gly Ser Ser Asn Asn Lys Phe Pro Ala Ala Ile Phe Arg Tyr
            340                 345                 350

Gln Gly Ala Pro Ala Thr Leu Pro Thr Asp Gln Gly Leu Pro Val Pro
            355                 360                 365

Asn His Met Cys Leu Asp Asn Leu Asn Leu Thr Pro Val Val Thr Arg
        370                 375                 380

Ser Ala Pro Val Asn Asn Phe Val Lys Arg Pro Ser Asn Thr Leu Gly
385                 390                 395                 400

Val Thr Leu Asp Ile Gly Gly Thr Pro Leu Phe Val Trp Lys Val Asn
                405                 410                 415

Gly Ser Ala Ile Asn Val Asp Trp Gly Lys Pro Ile Leu Asp Tyr Val
                420                 425                 430

Met Ser Gly Asn Thr Ser Tyr Pro Val Ser Asp Asn Ile Val Gln Val
            435                 440                 445

Asp Ala Val Asp Gln Trp Thr Tyr Trp Leu Ile Glu Asn Asp Pro Thr
        450                 455                 460

Asn Pro Ile Val Ser Leu Pro His Pro Met His Leu His Gly His Asp
465                 470                 475                 480

Phe Leu Val Leu Gly Arg Ser Pro Asp Glu Leu Pro Ser Ala Gly Val
                485                 490                 495
```

```
-continued

Arg His Ile Phe Asp Pro Ala Lys Asp Leu Pro Arg Leu Lys Gly Asn
            500                 505                 510

Asn Pro Val Arg Arg Asp Val Thr Met Leu Pro Ala Gly Gly Trp Leu
        515                 520                 525

Leu Leu Ala Phe Lys Thr Asp Asn Pro Gly Ala Trp Leu Phe His Cys
    530                 535                 540

His Ile Ala Trp His Val Ser Gly Gly Leu Ser Val Asp Phe Leu Glu
545                 550                 555                 560

Arg Pro Asn Asp Leu Arg Thr Gln Leu Asn Ser Asn Ala Lys Arg Ala
            565                 570                 575

Asp Arg Asp Asp Phe Asn Arg Val Cys Arg Glu Trp Asn Ala Tyr Trp
            580                 585                 590

Pro Thr Asn Pro Phe Pro Lys Ile Asp Ser Gly Leu Arg His Arg Phe
        595                 600                 605

Val Glu Glu Ser Glu Trp Met Val Arg
        610                 615
```